United States Patent
Brito et al.

(10) Patent No.: US 11,905,525 B2
(45) Date of Patent: Feb. 20, 2024

(54) REDUCTION OF ELIMINATION OF IMMUNE RESPONSES TO NON-INTRAVENOUS, E.G., SUBCUTANEOUSLY ADMINISTERED THERAPEUTIC PROTEINS

(71) Applicant: ModernaTX, Inc., Cambridge, MA (US)

(72) Inventors: Luis Brito, Concord, MA (US); Gilles Besin, Brookline, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/603,111

(22) PCT Filed: Apr. 5, 2018

(86) PCT No.: PCT/US2018/026286
§ 371 (c)(1),
(2) Date: Oct. 4, 2019

(87) PCT Pub. No.: WO2018/187590
PCT Pub. Date: Oct. 11, 2018

(65) Prior Publication Data
US 2020/0109420 A1 Apr. 9, 2020

Related U.S. Application Data

(60) Provisional application No. 62/484,774, filed on Apr. 12, 2017, provisional application No. 62/482,169, filed on Apr. 5, 2017.

(51) Int. Cl.
*C12N 15/88* (2006.01)
*A61K 9/00* (2006.01)
(Continued)

(52) U.S. Cl.
CPC .......... *C12N 15/88* (2013.01); *A61K 9/0019* (2013.01); *A61K 9/1271* (2013.01);
(Continued)

(58) Field of Classification Search
CPC .. C12N 15/88; C12N 2310/141; C12N 15/67; A61K 9/0019; A61K 9/1271;
(Continued)

(56) References Cited

U.S. PATENT DOCUMENTS 6,303,113 B1 * 10/2001 Woog ............... A61K 47/10
514/14.6
6,395,253 B2   5/2002 Levy et al.
(Continued)

FOREIGN PATENT DOCUMENTS

AU   2015210364 A1   3/2017
EP   3608308 A       2/2020
(Continued)

OTHER PUBLICATIONS

U.S. Appl. No. 16/048,154, filed Jul. 27, 2018, Ciaramella et al.
(Continued)

*Primary Examiner* — Gollamudi S Kishore
(74) *Attorney, Agent, or Firm* — Wolf, Greenfield & Sacks, P.C.

(57) ABSTRACT

This disclosure provides improved lipid-based compositions, including lipid nanoparticle compositions, and methods of use thereof for delivering nucleic acids in vivo. These compositions have reduced immune activation resulting in accelerated blood clearance and/or anti-drug antibodies and they have an improved toxicity profile and therapeutic index in vivo.

16 Claims, 14 Drawing Sheets

Specification includes a Sequence Listing.

(51) Int. Cl.
*A61K 9/127* (2006.01)
*A61K 31/7105* (2006.01)
*A61K 47/12* (2006.01)
*A61K 47/28* (2006.01)

(52) U.S. Cl.
CPC .......... *A61K 31/7105* (2013.01); *A61K 47/12* (2013.01); *A61K 47/28* (2013.01); *C12N 2310/141* (2013.01)

(58) Field of Classification Search
CPC .... A61K 31/7105; A61K 47/12; A61K 47/28; A61K 31/713; A61K 9/127
See application file for complete search history.

(56) References Cited

U.S. PATENT DOCUMENTS

| | | | |
|---|---|---|---|
| 6,756,053 B2 * | 6/2004 | Zhang | A61P 5/00 424/443 |
| 8,058,069 B2 | 11/2011 | Yaworski et al. | |
| 8,158,601 B2 | 4/2012 | Chen et al. | |
| 8,217,016 B2 | 7/2012 | Hoerr et al. | |
| 8,652,487 B2 | 2/2014 | Maldonado | |
| 8,691,966 B2 | 4/2014 | Kariko et al. | |
| 8,710,200 B2 | 4/2014 | Schrum et al. | |
| 8,754,062 B2 | 6/2014 | De Fougerolles et al. | |
| 8,822,663 B2 | 9/2014 | Schrum et al. | |
| 8,980,864 B2 | 3/2015 | Hoge et al. | |
| 8,999,380 B2 | 4/2015 | Bancel et al. | |
| 9,221,891 B2 | 12/2015 | Bancel et al. | |
| 9,283,287 B2 | 3/2016 | Bancel et al. | |
| 9,303,079 B2 | 4/2016 | Bancel et al. | |
| 9,364,433 B2 * | 6/2016 | Andersson | A61P 31/00 |
| 9,464,124 B2 | 10/2016 | Bancel et al. | |
| 9,512,456 B2 | 12/2016 | Wang et al. | |
| 9,533,047 B2 | 1/2017 | de Fougerolles et al. | |
| 9,572,896 B2 | 2/2017 | Bancel et al. | |
| 9,597,380 B2 | 3/2017 | Chakraborty et al. | |
| 9,675,668 B2 | 6/2017 | Bancel et al. | |
| 9,803,199 B2 | 10/2017 | Koizumi et al. | |
| 9,868,691 B2 | 1/2018 | Benenato et al. | |
| 9,872,900 B2 | 1/2018 | Ciaramella et al. | |
| 10,023,626 B2 | 7/2018 | Bolen et al. | |
| 10,064,934 B2 | 9/2018 | Ciaramella et al. | |
| 10,064,935 B2 | 9/2018 | Ciaramella et al. | |
| 10,124,055 B2 | 11/2018 | Ciaramella et al. | |
| 10,207,010 B2 | 2/2019 | Besin et al. | |
| 10,232,055 B2 | 3/2019 | Kariko et al. | |
| 10,273,269 B2 | 4/2019 | Ciaramella | |
| 10,286,086 B2 | 5/2019 | Roy et al. | |
| 10,323,076 B2 | 6/2019 | Ellsworth et al. | |
| 10,385,088 B2 | 8/2019 | Fraley et al. | |
| 10,449,244 B2 | 10/2019 | Ciaramella et al. | |
| 10,465,190 B1 | 11/2019 | Chen et al. | |
| 10,493,143 B2 | 12/2019 | Ciaramella et al. | |
| 10,526,629 B2 | 1/2020 | Rabideau et al. | |
| 10,653,712 B2 | 5/2020 | Hoge | |
| 10,653,767 B2 | 5/2020 | Ciaramella et al. | |
| 10,695,419 B2 | 6/2020 | Ciaramella et al. | |
| 10,857,105 B2 | 12/2020 | Benenato et al. | |
| 10,925,958 B2 | 2/2021 | Ciaramella | |
| 11,027,025 B2 | 6/2021 | Hoge et al. | |
| 11,045,540 B2 | 6/2021 | Ciaramella | |
| 11,103,578 B2 | 8/2021 | Ciaramella et al. | |
| 11,351,242 B1 | 6/2022 | Lori et al. | |
| 11,384,352 B2 | 7/2022 | Miracco | |
| 11,406,703 B2 | 8/2022 | Kramarczyk et al. | |
| 11,464,848 B2 | 10/2022 | Ciaramella et al. | |
| 11,485,960 B2 | 11/2022 | Dousis et al. | |
| 11,497,807 B2 | 11/2022 | Ciaramella et al. | |
| 11,564,893 B2 | 1/2023 | Smith | |
| 11,576,961 B2 | 2/2023 | Ciaramella et al. | |
| 11,643,441 B1 | 5/2023 | Ciaramella et al. | |
| 11,696,946 B2 | 7/2023 | Ciaramella | |
| 11,752,206 B2 | 9/2023 | Ciaramella et al. | |
| 2003/0073619 A1 | 4/2003 | Mahato et al. | |
| 2006/0008910 A1 | 1/2006 | Maclachlan et al. | |
| 2006/0204566 A1 | 9/2006 | Smyth-Templeton et al. | |
| 2008/0025944 A1 | 1/2008 | Hoerr et al. | |
| 2010/0068226 A1 | 3/2010 | Taylor et al. | |
| 2010/0130588 A1 | 5/2010 | Yaworski et al. | |
| 2010/0239608 A1 | 9/2010 | Von Der Mulbe et al. | |
| 2010/0310562 A1 * | 12/2010 | Kroczek | C07K 16/2866 424/134.1 |
| 2012/0101148 A1 | 4/2012 | Aking et al. | |
| 2012/0172411 A1 | 7/2012 | Heyes et al. | |
| 2013/0064894 A1 | 3/2013 | Martin et al. | |
| 2013/0102034 A1 | 4/2013 | Schrum et al. | |
| 2013/0115274 A1 | 5/2013 | Knopov et al. | |
| 2013/0116307 A1 | 5/2013 | Heyes et al. | |
| 2013/0129785 A1 | 5/2013 | Manoharan et al. | |
| 2013/0142818 A1 | 6/2013 | Baumhof et al. | |
| 2013/0143869 A1 * | 6/2013 | Kiehm | A61K 31/138 514/217 |
| 2013/0158021 A1 | 6/2013 | Dong et al. | |
| 2013/0165901 A1 * | 6/2013 | Ruchti | G16H 50/20 604/504 |
| 2013/0171241 A1 | 7/2013 | Geall | |
| 2013/0202684 A1 | 8/2013 | Geall et al. | |
| 2013/0236500 A1 | 9/2013 | Zale et al. | |
| 2013/0236533 A1 | 9/2013 | Von Andrian et al. | |
| 2013/0236974 A1 | 9/2013 | De Fougerolles | |
| 2013/0243827 A1 | 9/2013 | Troiano et al. | |
| 2013/0245103 A1 | 9/2013 | de Fougerolles et al. | |
| 2013/0259923 A1 | 10/2013 | Bancel et al. | |
| 2013/0266640 A1 | 10/2013 | De Fougerolles et al. | |
| 2013/0330401 A1 | 12/2013 | Payne et al. | |
| 2014/0017327 A1 | 1/2014 | Cheng et al. | |
| 2014/0037660 A1 | 2/2014 | Folin-Mleczek et al. | |
| 2014/0039032 A1 | 2/2014 | Kumboyama et al. | |
| 2014/0044791 A1 | 2/2014 | Basilion et al. | |
| 2014/0079774 A1 | 3/2014 | Brinker et al. | |
| 2014/0147432 A1 | 5/2014 | Bancel et al. | |
| 2014/0147454 A1 | 5/2014 | Chakraborty et al. | |
| 2014/0148502 A1 | 5/2014 | Bancel et al. | |
| 2014/0193482 A1 | 7/2014 | Bancel et al. | |
| 2014/0206752 A1 | 7/2014 | Afeyan et al. | |
| 2014/0255472 A1 | 9/2014 | Geall et al. | |
| 2014/0308304 A1 | 10/2014 | Manoharan et al. | |
| 2014/0378538 A1 | 12/2014 | Bancel | |
| 2015/0051268 A1 | 2/2015 | Bancel et al. | |
| 2015/0056253 A1 | 2/2015 | Bancel et al. | |
| 2015/0141499 A1 | 5/2015 | Bancel et al. | |
| 2015/0307542 A1 | 10/2015 | Roy et al. | |
| 2015/0315541 A1 | 11/2015 | Bancel et al. | |
| 2015/0376115 A1 | 12/2015 | Ansell et al. | |
| 2016/0022580 A1 | 1/2016 | Ramsay et al. | |
| 2016/0024140 A1 | 1/2016 | Issa et al. | |
| 2016/0024141 A1 | 1/2016 | Issa et al. | |
| 2016/0032273 A1 | 2/2016 | Shahrokh et al. | |
| 2016/0038612 A1 | 2/2016 | Hoge et al. | |
| 2016/0194368 A1 | 7/2016 | Hoge et al. | |
| 2016/0243221 A1 | 8/2016 | Hoge et al. | |
| 2016/0317647 A1 | 11/2016 | Ciaramella et al. | |
| 2016/0367638 A1 * | 12/2016 | Byers | A61K 9/0019 |
| 2016/0367651 A1 | 12/2016 | Shiku et al. | |
| 2016/0376224 A1 | 12/2016 | Du et al. | |
| 2017/0043037 A1 | 2/2017 | Kariko et al. | |
| 2017/0202979 A1 | 7/2017 | Chakraborty et al. | |
| 2017/0204152 A1 | 7/2017 | Nelson et al. | |
| 2017/0239371 A1 | 8/2017 | Guild et al. | |
| 2017/0130255 A1 | 10/2017 | Wang et al. | |
| 2018/0000953 A1 | 1/2018 | Almarsson et al. | |
| 2018/0002393 A1 | 1/2018 | Bancel et al. | |
| 2018/0237849 A1 | 8/2018 | Thompson | |
| 2018/0243225 A1 | 8/2018 | Ciaramella | |
| 2018/0243230 A1 | 8/2018 | Smith | |
| 2018/0256628 A1 | 9/2018 | Hoge et al. | |
| 2018/0271795 A1 | 9/2018 | Martini et al. | |
| 2018/0271970 A1 | 9/2018 | Ciaramella et al. | |
| 2018/0273977 A1 | 9/2018 | Mousavi et al. | |
| 2018/0274009 A1 | 9/2018 | Marquardt et al. | |
| 2018/0303929 A1 | 10/2018 | Ciaramella et al. | |
| 2018/0311336 A1 | 11/2018 | Ciaramella et al. | |

(56) References Cited

U.S. PATENT DOCUMENTS

| | | |
|---|---|---|
| 2018/0311343 A1 | 11/2018 | Huang et al. |
| 2018/0318409 A1 | 11/2018 | Valiante et al. |
| 2018/0326039 A1 | 11/2018 | Haruta |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0274968 A1 | 9/2019 | Weissman et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0338004 A1 | 10/2020 | Hansson et al. |
| 2020/0368162 A1 | 11/2020 | Martini |
| 2021/0023199 A1 | 1/2021 | Kallen et al. |
| 2021/0030866 A1 | 2/2021 | Kallen et al. |
| 2021/0046173 A1 | 2/2021 | Ciaramella et al. |
| 2021/0060175 A1 | 3/2021 | Baumhof et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0062408 A1 | 3/2022 | Kramarczyk et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |
| 2023/0181481 A1 | 6/2023 | White et al. |
| 2023/0190761 A1 | 6/2023 | Brader et al. |
| 2023/0212645 A1 | 7/2023 | Marquardt et al. |
| 2023/0287437 A1 | 9/2023 | Smith et al. |

FOREIGN PATENT DOCUMENTS

| | | |
|---|---|---|
| JP | 2015-518472 A | 7/2015 |
| JP | 2015-519346 A | 7/2015 |
| WO | WO 1995/026204 | 10/1995 |
| WO | WO 2005/120152 A2 | 12/2005 |
| WO | WO 2005/121348 A1 | 12/2005 |
| WO | WO 2007/094854 A2 | 8/2007 |
| WO | WO 2009/127230 A1 | 10/2009 |
| WO | WO 2010/037408 A1 | 4/2010 |
| WO | WO 2010/054406 A1 | 5/2010 |
| WO | WO 2011/068810 A1 | 6/2011 |
| WO | WO 2011/140627 A1 | 11/2011 |
| WO | WO 2012/030901 A1 | 3/2012 |
| WO | WO 2012/149252 A2 | 11/2012 |
| WO | WO 2012/159643 A1 | 11/2012 |
| WO | WO 2012/159754 A1 | 11/2012 |
| WO | WO 2013/006838 A1 | 1/2013 |
| WO | WO 2013/086354 A1 | 6/2013 |
| WO | WO 2013/087083 A1 | 6/2013 |
| WO | WO 2013/149141 A1 | 10/2013 |
| WO | WO 2014/089239 A1 | 6/2014 |
| WO | WO 2014/152211 A1 | 9/2014 |
| WO | WO 2014/159813 A1 | 10/2014 |
| WO | WO 2014/160243 A1 | 10/2014 |
| WO | WO 2015/005253 A1 | 1/2015 |
| WO | WO 2015/050158 A1 | 4/2015 |
| WO | WO 2015/095346 A1 | 6/2015 |
| WO | WO 2016/128376 A1 | 8/2016 |
| WO | WO 2016/164762 A1 | 10/2016 |
| WO | WO 2016/201377 A1 | 12/2016 |
| WO | WO 2017/011773 A2 | 1/2017 |
| WO | WO 2017/015457 A1 | 1/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/049245 A3 | 5/2017 |
| WO | WO 2017/075531 A1 | 5/2017 |
| WO | WO 2017/099823 A2 | 6/2017 |
| WO | WO 2017/112865 A1 | 6/2017 |
| WO | WO 2017/127750 A1 | 7/2017 |
| WO | WO 2017/201333 A1 | 11/2017 |
| WO | WO 2017/201340 A1 | 11/2017 |
| WO | WO 2016/091391 A1 | 2/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/187590 A2 | 10/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/146814 A1 | 7/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/211343 A1 | 10/2021 |
| WO | WO 2021/222304 A1 | 11/2021 |

(56) References Cited

FOREIGN PATENT DOCUMENTS

| | | |
|---|---|---|
| WO | WO 2021/231929 A1 | 11/2021 |
| WO | WO 2021/231963 A1 | 11/2021 |
| WO | WO 2021/237084 A1 | 11/2021 |
| WO | WO 2021/237174 A1 | 11/2021 |
| WO | WO 2021/239880 A1 | 12/2021 |
| WO | WO 2021/247817 A1 | 12/2021 |
| WO | WO 2022/032154 A2 | 2/2022 |
| WO | WO 2022/067010 A1 | 3/2022 |
| WO | WO 2022/076562 A1 | 4/2022 |
| WO | WO 2022/101469 A1 | 5/2022 |
| WO | WO 2022/155524 A1 | 7/2022 |
| WO | WO 2022/155530 A1 | 7/2022 |
| WO | WO 2022/187698 A1 | 9/2022 |
| WO | WO 2022/197624 A1 | 9/2022 |
| WO | WO 2022/204491 A1 | 9/2022 |
| WO | WO 2022/212191 A1 | 10/2022 |
| WO | WO 2022/212442 A1 | 10/2022 |
| WO | WO 2022/212711 A2 | 10/2022 |
| WO | WO 2022/221335 A1 | 10/2022 |
| WO | WO 2022/221336 A1 | 10/2022 |
| WO | WO 2022/221359 A1 | 10/2022 |
| WO | WO 2022/221440 A1 | 10/2022 |
| WO | WO 2022/226277 A1 | 10/2022 |
| WO | WO 2022/226318 A1 | 10/2022 |
| WO | WO 2022/232585 A1 | 11/2022 |
| WO | WO 2022/241103 A1 | 11/2022 |
| WO | WO 2022/245888 A1 | 11/2022 |
| WO | WO 2022/266010 A1 | 12/2022 |
| WO | WO 2022/266012 A1 | 12/2022 |
| WO | WO 2022/266389 A1 | 12/2022 |
| WO | WO 2023/283642 A2 | 1/2023 |
| WO | WO 2023/283645 A1 | 1/2023 |
| WO | WO 2023/283651 A1 | 1/2023 |
| WO | WO 2023/014649 A1 | 2/2023 |
| WO | WO 2023/018773 A1 | 2/2023 |
| WO | WO 2023/018923 A1 | 2/2023 |
| WO | WO 2023/019181 A1 | 2/2023 |
| WO | WO 2023/056401 A1 | 4/2023 |
| WO | WO 2023/069625 A1 | 4/2023 |
| WO | WO 2023/069895 A1 | 4/2023 |
| WO | WO 2023/069900 A1 | 4/2023 |
| WO | WO 2023/076658 A1 | 5/2023 |
| WO | WO 2023/081311 A1 | 5/2023 |
| WO | WO 2023/092069 A1 | 5/2023 |
| WO | WO 2023/107999 A2 | 6/2023 |
| WO | WO 2023/114307 A1 | 6/2023 |
| WO | WO 2023/132885 A1 | 7/2023 |
| WO | WO 2023/137149 A1 | 7/2023 |
| WO | WO 2023/150256 A1 | 8/2023 |
| WO | WO 2023/154818 A1 | 8/2023 |

OTHER PUBLICATIONS

U.S. Appl. No. 90/014,395, filed Oct. 24, 2019, Ciaramella et al.
U.S. Appl. No. 15/753,297, filed Feb. 17, 2018, Thompson.
U.S. Appl. No. 15/748,782, filed Jan. 30, 2018, Mousavi et al.
U.S. Appl. No. 16/450,882, filed Jun. 24, 2019, Ciaramella.
U.S. Appl. No. 16/136,503, filed Sep. 20, 2018, Ciaramella et al.
U.S. Appl. No. 15/746,286, filed Jan. 19, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 16/582,621, filed Sep. 25, 2019, Chen et al.
U.S. Appl. No. 16/001,786, filed Jun. 6, 2018, Hoge et al.
U.S. Appl. No. 16/333,330, filed Mar. 14, 2019, Hoge et al.
U.S. Appl. No. 16/389,545, filed Apr. 19, 2019, Ciaramella et al.
U.S. Appl. No. 16/368,278, filed Mar. 28, 2019, Ciaramella et al.
U.S. Appl. No. 16/805,587, filed Feb. 28, 2020, Ciaramella et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/657,122, filed Oct. 18, 2019, Rabideau et al.
U.S. Appl. No. 16/494,162, filed Sep. 13, 2019, Ciaramella.
U.S. Appl. No. 16/131,793, filed Sep. 14, 2018, Ciaramella et al.
U.S. Appl. No. 16/608,451, filed Oct. 25, 2019, Ciaramella et al.
PCT/US2018/026286, Jul. 26, 2018, International Search Report and Written Opinion.
Abu Lila et al., Application of polyglycerol coating to plasmid DNA lipoplex for the evasion of the accelerated blood clearance phenomenon in nucleic acid delivery. J Pharm Sci. Feb. 2014;103(2):557-66. doi: 10.1002/jps.23823. Epub Dec. 17, 2013.
Abu Lila et al., The accelerated blood clearance (ABC) phenomenon: clinical challenge and approaches to manage. J Control Release. Nov. 28, 2013;172(1):38-47. doi: 10.1016/j.jconrel.2013.07.026. Epub Aug. 7, 2013.
Abu Lila et al., Use of polyglycerol (PG), instead of polyethylene glycol (PEG), prevents induction of the accelerated blood clearance phenomenon against long-circulating liposomes upon repeated administration. Int J Pharm. Nov. 1, 2013;456(1):235-42. doi:10.1016/j.ijpharm.2013.07.059. Epub Aug. 5, 2013.
Betker et al., Nonadditive Effects of Repetitive Administration of Lipoplexes in Immunocompetent Mice. J Pharm Sci. Mar. 2017;106(3):872-881. doi:10.1016/j.xphs.2016.11.013. Epub Nov. 2, 20162.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Delehanty et al., Peptides for specific intracellular delivery and targeting of nanoparticles: implications for developing nanoparticle-mediated drug delivery. Ther Deliv. Sep. 2010;1(3):411-33.
Ewert et al., Cationic liposome-nucleic acid complexes for gene delivery and silencing: pathways and mechanisms for plasmid DNA and siRNA. Top Curr Chem. 2010;296:191-226.
Felgner, PL Cationic lipid/polynucleotide condensates for in vitro and in vivo polynucleotide delivery—the cytofectins. J. of Liposome Research. 1993; 3(1): 3-16.
Felgner, PL Particulate systems and polymers for in vitro and in vivo delivery of polynucleotides. Adv. Drug Delivery Rev. 1990; 5(3): 163-187.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Hajj et al., Tools for translation: non-viral materials for therapeutic mRNA delivery. Nat Rev Mat. Sep. 2017;2:17056.
Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull. 2015;38(3):417-24. doi: 10.1248/bpb.b14-00653.
Hecker, Nonviral, cationic lipid-mediated delivery of mRNA. Methods Mol Biol. 2013;969:73-88. doi: 10.1007/978-1-62703-260-5_5.
Heyes et al., Cationic lipid saturation influences intracellular delivery of encapsulated nucleic acids. J Control Release. Oct. 3, 2005;107(2):276-87.
Hsu et al., Cationic lipid nanoparticles for therapeutic delivery of siRNA and miRNA to murine liver tumor. Nanomedicine. Nov. 2013;9(8):1169-80. doi: 10.1016/j.nano.2013.05.007. Epub May 30, 2013.
Janeway et al., Immunobiology: the immune system in health and disease. Garland Publishing, Inc, London. 1997; Chapter 13:12-13:21.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kariko et al., Incorporation of pseudouridine into mRNA yields superior nonimmunogenic vector with increased translational capacity and biological stability, Molecular Therapy, Nature Publishing Group, GB, vol. 16, No. 11, Nov. 1, 2008 (Nov. 1, 2008), pp. 1833-1840.
Kariko, K. et al., Phosphate-enhanced transfection of cationic lipid-complexed mRNA and plasmid DNA. Biochim Biophys Acta. Mar. 2, 1998;1369(2):320-34.

(56) References Cited

OTHER PUBLICATIONS

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kozielski et al., Bioreducible cationic polymer-based nanoparticles for efficient and environmentally triggered cytoplasmic siRNA delivery to primary human brain cancer cells. ACS Nano. Apr. 22, 2014;8(4):3232-41. doi: 10.1021/nn500704t. Epub Apr. 3, 2014.
Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.
Li, L. et al., Overcoming obstacles to develop effective and safe siRNA therapeutics. Expert Opin Biol Ther. May 2009; 9(5): 609-19.
Luo, D. et al., Synthetic DNA delivery systems. Nat Biotechnol. Jan. 2000; 18(1):33-7.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Marć et al., Nucleic acid vaccination strategies against infectious diseases. Expert Opin Drug Deliv. 2015;12(12):1851-65. doi:10.1517/17425247.2015.1077559. Epub Sep. 12, 2015.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Oja et al., Doxorubicin entrapped within liposome-associated antigens results in a selective inhibition of the antibody response to the linked antigen. Biochim Biophys Acta. Sep. 29, 2000;1468(1-2):31-40.
Pollard, C., et al., Type I IFN counteracts the induction of antigen-specific immune responses by lipid-based delivery of mRNA vaccines. Mol Ther. Jan. 2013; 21 (1): 251-259.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Semple, S.C., et al., Rational design of cationic lipids for siRNA delivery. Nat Biotechnol. Feb. 2010; 28(2): 172-176.
Shimizu et al., Transport of PEGylated liposomes from the splenic marginal zone to the follicle in the induction phase of the accelerated blood clearance phenomenon. Immunobiology. May 2013;218(5):725-32. doi: 10.1016/j.imbio.2012.08.274. Epub Aug. 23, 2012.
Taguchi et al., Effect of Repeated Injections of Adenosine Diphosphate-Encapsulated Liposomes Coated with a Fibrinogen γ-Chain Dodecapeptide Developed as a Synthetic Platelet Substitute on Accelerated Blood Clearance in a Healthy and an Anticancer Drug-Induced Thrombocytopenia Rat Model. J Pharm Sci. Sep. 2015;104(9):3084-91. doi: 10.1002/jps.24418. Epub Mar. 9, 2015.
Taguchi et al., Hemoglobin vesicles, polyethylene glycol (PEG)ylated liposomes developed as a red blood cell substitute, do not induce the accelerated blood clearance phenomenon in mice. Drug Metab Dispos. Nov. 2009;37(11):2197-203. doi: 10.1124/dmd.109.028852. Epub Aug. 13, 2009.
Torchilin, Multifunctional and stimuli-sensitive pharmaceutical nanocarriers. Eur J Pharm Biopharm. Mar. 2009;71(3):431-44. doi: 10.1016/j.ejpb.2008.09.026. Epub Oct. 17, 2008.
Uzgun, S., et al., PEGylation improves nanoparticle formation and transfection efficiency of messenger RNA. Pharm Res. Sep. 2011; 28(9); 2223-2232.
Wan et al., Lipid nanoparticle delivery systems for siRNA-based therapeutics. Drug Deliv Transl Res. Feb. 2014;4(1):74-83. doi:10.1007/s13346-013-0161-z.
Zhao et al., A frustrating problem: accelerated blood clearance of PEGylated solid lipid nanoparticles following subcutaneous injection in rats. Eur J Pharm Biopharm. Aug. 2012;81(3):506-13. doi: 10.1016/j.ejpb.2012.04.023. Epub May 11, 2012.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Kowalski et al., Delivering the Messenger: Advances in Technologies for Therapeutic mRNA Delivery. Molecular Therapy vol. 27 No. 4 Apr. 2019.
Michel T. et al.: "Cationic Nanoliposomes Meet mRNA: Efficient Delivery of Modified mRNA Using Hemocompatible and Stable Vectors for Therapeutic Applications" Molecular Therapy Nucleic Acids, 2017, vol. 8, pp. 459-468, http://dx.doi.org/10.1016/j.omtn.2017.07.013.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Reichmuth et al., mRNA Vaccine Delivery Using Lipid Nanoparticles. Ther Deliv. 2016;7(5):319-34. doi: 10.4155/tde-2016-0006.
Schlake et al., Developing mRNA-vaccine technologies. RNA Biol. Nov. 2012;9(11):1319-30. doi: 10.4161/rna.22269. Epub Oct. 12, 2012.
Zeng et al., Formulation and Delivery Technologies for mRNA Vaccines. Curr Top Microbiol Immunol. Jun. 2, 2020;10.1007/82_2020_217. doi: 10.1007/82_2020_217.
Zhao et al., Nanoparticle vaccines. Vaccine. Jan. 9, 2014;32(3):327-37. doi: 10.1016/j.vaccine.2013.11.069. Epub Dec. 2, 2013.
Austin et al., Split-Dose Administration Enhances Immune Responses Elicited by a mRNA/Lipid Nanoparticle Vaccine Expressing Respiratory Syncytial Virus F Protein. Mol Pharm. Jan. 2, 2023;20(1):279-289. doi: 10.1021/acs.molpharmaceut.2c00635. Epub Oct. 17, 2022.
Chaudhary et al., mRNA vaccines for infectious diseases: principles, delivery and clinical translation. Nature Reviews Drug Discovery vol. 20, pP. 817-838 (2021).
Geall et al., RNA: the new revolution in nucleic acid vaccines. Semin Immunol. Apr. 2013;25(2):152-9. doi: 10.1016/j.smim.2013.05.001. Epub Jun. 2, 2013.
Hashiba et al., The use of design of experiments with multiple responses to determine optimal formulations for in vivo hepatic mRNA delivery. J Control Release. Nov. 10, 2020;327:467-476. doi: 10.1016/j.jconrel.2020.08.031. Epub Aug. 25, 2020.
Hou et al., Lipid nanoparticles for mRNA delivery. Nature Reviews Materials vol. 6, pp. 1078-1094 (2021).
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Ulmer et al., RNA-based vaccines. Vaccine. Jun. 22, 2012;30(30):4414-8. doi: 10.1016/j.vaccine.2012.04.060. Epub Apr. 28, 2012.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/468,838, filed Jun. 12, 2019, Miracco.
U.S. Appl. No. 16/788,182, filed Feb. 11, 2020, Panther et al.

(56) References Cited

OTHER PUBLICATIONS

U.S. Appl. No. 17/000,215, filed Aug. 21, 2020, Metkar et al.
Barbier et al., The clinical progress of mRNA vaccines and immunotherapies. Nat Biotechnol. Jun. 2022;40(6):840-854. doi: 10.1038/s41587-022-01294-2. Epub May 9, 2022.
Peek et al., Nanotechnology in vaccine delivery. Adv Drug Deliv Rev. May 22, 2008;60(8):915-28. doi: 10.1016/j.addr.2007.05.017. Epub Feb. 7, 2008.
Tenchov et al., Lipid Nanoparticles—From Liposomes to mRNA Vaccine Delivery, a Landscape of Research Diversity and Advancement. ACS Nano. Nov. 23, 2021;15(11):16982-17015. doi: 10.1021/acsnano.1c04996. Epub Jun. 28, 2021.
Shidhadye et al., Solid lipid nanoparticles and nanostructured lipid carriers—innovative generations of solid lipid carriers. Curr Drug Deliv. Oct. 2008;5(4):324-31. doi: 10.2174/156720108785915087.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/548,172, filed Dec. 10, 2021, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 17/830,742, filed Jun. 2, 2022, Miracco.
U.S. Appl. No. 16/001,765, filed Jun. 6, 2018, Marquardt et al.
U.S. Appl. No. 17/852,974, filed Jun. 29, 2022, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 17/737,581, filed May 5, 2022, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/411,896, filed Aug. 25, 2021, Kramarczyk et al.
U.S. Appl. No. 17/840,478, filed Jun. 14, 2022, Kramarczyk et al.
U.S. Appl. No. 17/000,201, filed Aug. 21, 2020, Stewart-Jones et al.
U.S. Appl. No. 17/518,542, filed Nov. 3, 2021, Metkar et al.
U.S. Appl. No. 17/572,465, filed Jan. 10, 2022, Nachbagauer et al.
U.S. Appl. No. 17/726,971, filed Apr. 22, 2022, Hennessy.
U.S. Appl. No. 17/204,801, filed Mar. 17, 2021, Ciaramella et al.
U.S. Appl. No. 18/161,857, filed Jan. 30, 2023, Smith.
U.S. Appl. No. 17/819,414, filed Aug. 12, 2022, Ciaramella.
U.S. Appl. No. 18/093,119, filed Jan. 4, 2023, Mauger et al.
U.S. Appl. No. 18/055,193, filed Nov. 14, 2022, Ciaramella et al.
U.S. Appl. No. 17/823,255, filed Aug. 30, 2022, Ciaramella et al.
U.S. Appl. No. 17/938,823, filed Oct. 7, 2022, Ciaramella et al.
U.S. Appl. No. 17/816,696, filed Aug. 1, 2022, Dousis et al.
U.S. Appl. No. 18/008,139, filed Dec. 2, 2022, Smith et al.
U.S. Appl. No. 17/796,401, filed Jul. 29, 2022, Shaw et al.
U.S. Appl. No. 17/926,353, filed Nov. 18, 2022, Brader et al.
U.S. Appl. No. 17/925,114, filed Nov. 14, 2022, White et al.
U.S. Appl. No. 17/797,784, filed Aug. 5, 2022, Stewart-Jones et al.
U.S. Appl. No. 17/925,125, filed Nov. 14, 2022, White et al.
U.S. Appl. No. 18/085,457, filed Dec. 20, 2022, Joyal et al.
U.S. Appl. No. 18/448,856, filed Aug. 11, 2023, Rabideau et al.
U.S. Appl. No. 18/343,344, filed Jun. 28, 2023, Hoge et al.
U.S. Appl. No. 18/318,689, filed May 16, 2023, Hoge et al.
U.S. Appl. No. 18/356,335, filed Jul. 21, 2023, Mauger et al.
U.S. Appl. No. 18/280,362, filed Sep. 5, 2023, Bollman et al.

* cited by examiner

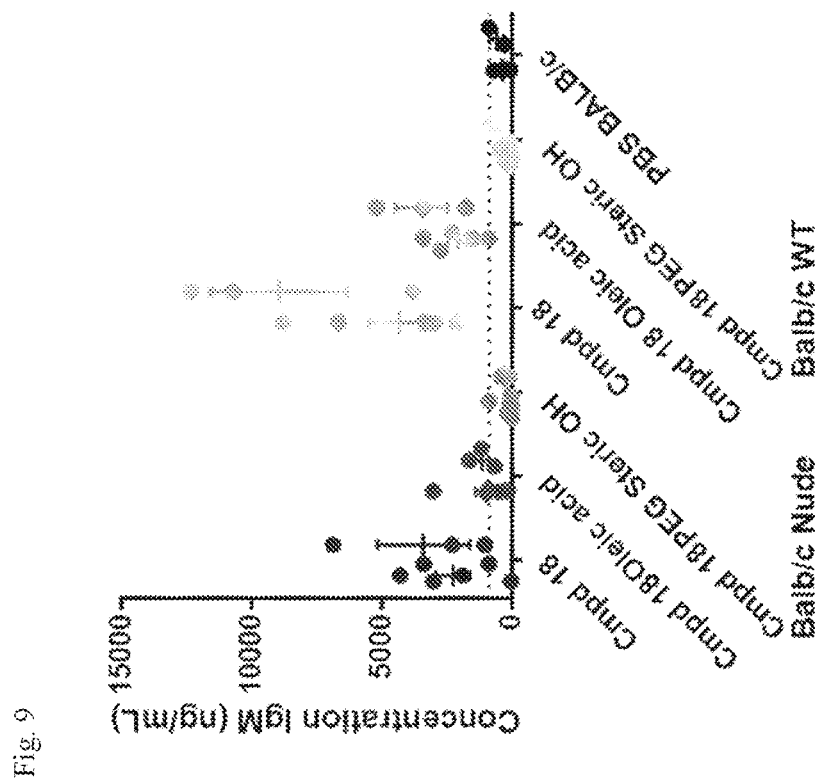
Fig. 9
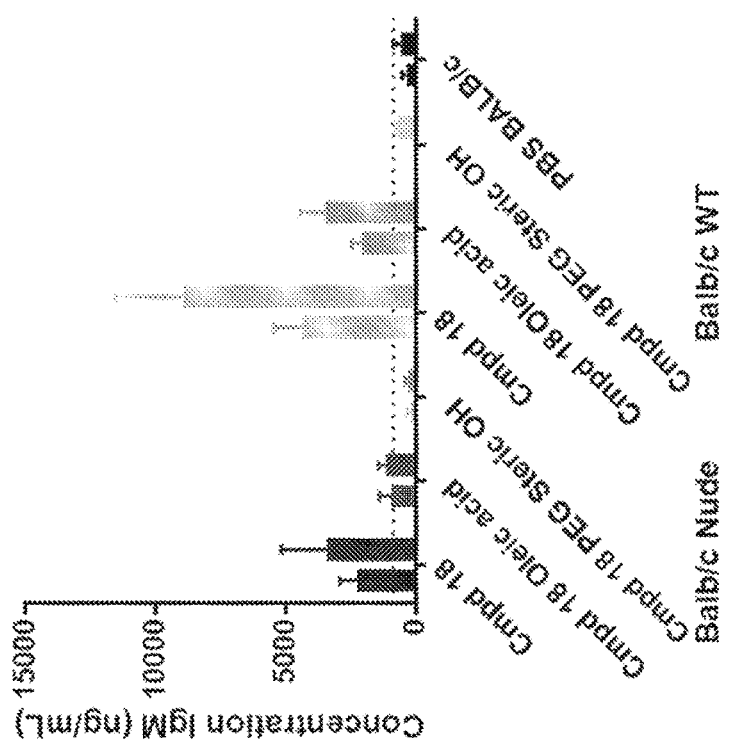

REDUCTION OF ELIMINATION OF IMMUNE RESPONSES TO NON-INTRAVENOUS, E.G., SUBCUTANEOUSLY ADMINISTERED THERAPEUTIC PROTEINS

RELATED APPLICATIONS

This application is a national stage filing under 35 U.S.C. § 371 of international application number PCT/US2018/026286, filed Apr. 5, 2018, which was published under PCT Article 21(2) in English and claims the benefit under 35 U.S.C. § 119(e) of U.S. provisional application No. 62/482,169, filed Apr. 5, 2017 and U.S. provisional application No. 62/484,774, filed Apr. 12, 2017, each of which is herein incorporated by reference in its entirety.

BACKGROUND

Effective in vivo delivery of active agents such as small molecule drugs, proteins, peptides, and nucleic acids represents a continuing medical challenge. Some active agents are recognized by the immune system, resulting in decreased efficacy and, in addition, some delivery vehicles (e.g., lipid nanoparticles (LNPs) can also promote immune responses). To address this issue, certain active agent formulations have incorporated polymers such as polyethylene glycol which was thought to cloak or mask the agent, thereby reducing its antigenicity and immunogenicity. However, even these "stealth" formulations have their limitations, including an inability to be repeatedly and frequently dosed, for example, over a period of days without loss of activity.

In addition, some agents or formulations when administered in vivo may interact with one or more cells or factors, potentially interfering with their functions, and ultimately resulting in adverse effects. Such adverse effects may limit the administration frequency and/or administered dose of the agent, or may preclude in vivo use altogether.

SUMMARY

The present disclosure is based, at least in part, on the discoveries that components of lipid nanoparticles (LNPs) and/or their active agent, i.e., nucleic acid cargo, when administered by non-intravenous routes, e.g., subcutaneously, intradermally or intramuscularly, may induce an innate immune response that interferes with robust sustained expression of protein from the nucleic acid. The diverse immune response which occurs after a first administration of LNPs and is enhanced on subsequent administrations can cause a dramatic loss in protein expression, significantly reducing the potential therapeutic effect in a subject. The LNPs and nucleic acids have an effect on a variety of immune cells and factors that effectively act together to reduce levels of expressed protein on subsequent administrations. The invention involves, in some aspects, the discovery that structural aspects of the LNPs and cargo can be modified to dampen this immune response, particularly after subcutaneous administration, avoiding the loss of protein expression associated with the use of traditional LNPs and nucleic acids.

In addition, the invention is based, at least in part, on the finding that one or more initial administrations of LNPs comprising a polynucleotide encoding a therapeutic protein via the intravenous route can induce tolerance to one or more subsequent administrations of the same therapeutic protein. The subsequently administered therapeutic protein may be in the form of, for example, a polynucleotide encoding the therapeutic protein present in an LNP or can be in the form of the protein itself. The subsequent administration may be by a subcutaneous, intramuscular, intradermal, or any non-intravenous route.

In some embodiments components of the LNPs, such as phosphatidylcholine, and of the nucleic acids may induce the production of natural IgM and/or IgG molecules, which may be mediated by activation of B1 cells, such as B1a and/or B1b cells. It has also been discovered according to the invention that T cells play a role in the unwanted immune response associated with subsequent administration of nucleic acid containing LNPs. These biological mechanisms may contribute to drug responses caused by LNPs, including accelerated blood clearance (ABC) and anti-drug antibodies (ADA). In some embodiments, LNPs lacking or comprising reduced amounts of these immunostimulatory components can be employed. Such LNPs may be particularly useful to maintain expression of intracellular protein upon repeat dosing of LNPs. In one embodiment, expression levels of intracellular protein may be maintained upon repeat dosing even without an initial IV dose of LNP comprising polynucleotide.

In further embodiments the initial administration of an intracellular protein in an LNP may be used to avoid an immune response against subsequent doses of other types of therapeutics. For instance the initial administration of the intracellular protein may be used to avoid ABC or ADA responses to subsequent administration of a therapeutic protein or a polynucleotide encoding a therapeutic protein.

This disclosure provides, in part, novel lipid nanoparticles (LNP) and LNP formulations with cargo, e.g., modified cargo, for subcutaneous administration that are less susceptible to recognition and thus clearance, by the immune system. The LNP provided herein have surprisingly improved clearance and in some instances, therapeutic index profiles. While not intending to be bound by any particular mechanism or theory, the improved clearance profiles are believed to have reduced recognition by and/or binding to certain immune cells including B and/or T cells and less overall effect on those and other immune cells and factors. Ideal LNPs include components which minimize immune cell activation and nucleic acids may include microRNA binding sites and/or chemical modifications that minimize immune cell activation. The combination of several factors leads to maximal immune suppression or tolerance to the administered drug, allowing the protein to be effectively expressed from the delivered nucleic acid.

In another embodiment, the present disclosure, in some aspects, includes a method for sequentially delivering lipid nanoparticles (LNPs) incorporating a nucleic acid encoding a protein (or administering therapeutic proteins themselves) to a subject by non-intravenous administration, e.g., subcutaneous administration, in order to produce therapeutically effective amounts of the protein after administering one or more initial doses of LNP comprising a nucleic acid molecule encoding that protein intravenously to induce tolerance. For example, in one embodiment the method comprises: administering at least one dose of LNPs comprising a polynucleotide encoding a therapeutic protein to the subject intravenously to induce tolerance, and subsequently administering at least one dose of LNPs comprising a polynucleotide encoding the same therapeutic protein to the subject by a non-intravenous route, wherein the subject has a reduce immune response or does not have an immune response that promotes accelerated blood clearance (ABC) and/or anti-drug antibody (ADA) to the non-intravenously administered therapeutic protein and wherein the subject maintains an effective amount of the protein for treating a disease. In one embodiment, sequential doses are administered within three weeks of one another.

In another embodiment, the method comprises: administering at least one dose of LNPs comprising a polynucleotide encoding a therapeutic protein to the subject intravenously to induce tolerance, and subsequently administering at least one dose of the same therapeutic protein (in the form of the protein itself) to the subject by a non-intravenous route, wherein the subject has a reduce immune response or does not have an immune response that promotes accelerated blood clearance (ABC) and/or anti-drug antibody (ADA) to the non-intravenously administered therapeutic protein and wherein the subject maintains an effective amount of the protein for treating a disease. In one embodiment, sequential doses are administered within three weeks of one another.

In a preferred embodiment, the LNPs of the invention are administered without coadministration of a tolerogenic agent, i.e., the LNPs of the invention lead to expression of one or more proteins of interest to be expressed in a subject, but do not contain mRNA encoding for an additional tolerogenic agent designed to modify the immune response. In one embodiment, the LNPs of the instant invention and/or the administration protocol provided herein results in tolerance to a therapeutic protein in the absence of an mRNA encoding an additional tolerogenic agent. In another preferred embodiment, the LNPs of the invention are administered without coadministration of a tolerogenic agent, i.e., the LNPs of the invention lead to expression of one or more proteins of interest to be expressed in a subject, but an additional tolerogenic agent is not administered as a protein molecule or small molecule. In one embodiment, the LNPs of the instant invention and/or the administration protocol provided herein results in tolerance to a therapeutic protein in the absence of an mRNA encoding an additional tolerogenic agent.

In some embodiments, the first dose is administered intravenously. In other embodiments, e.g., when the LNP is modified to reduce immunogenicity and/or when the polynucleotide encodes an intracellular protein, the first dose is administered subcutaneously. In some embodiments, a second dose is administered intravenously before the two or more subsequent doses of LNPs are administered subcutaneously. In further embodiments, a third dose is administered intravenously before the two or more subsequent doses of LNPs are administered subcutaneously. In other embodiments, a fourth, fifth, sixth, or additional dose is administered intravenously before the two or more subsequent doses of LNPs are administered subcutaneously.

In other embodiments, after one or more intravenous doses of LNP to induce tolerance to the cargo present therein, i.e., the protein expressed by the mRNA, and one or more subsequent administrations of LNP encoding the therapeutic protein (or subsequent administrations of therapeutic protein) via a non-intravenous route, additional intravenous doses of LNP can be administered to tolerize the subject again. For example, if, over time, the immune response to the therapeutic protein begins to increase (e.g., as measured by ADA and/or ABC or as measured by reduced levels of protein expression), one or more additional doses of LNP can be administered intravenously to further promote tolerance prior to returning to non-IV dosing.

In some embodiments, three subsequent doses of LNPs comprising a polynucleotide encoding a therapeutic protein (or therapeutic protein itself) are administered subcutaneously. In other embodiments, 4-6 subsequent doses of LNPs comprising a polynucleotide encoding a therapeutic protein (or therapeutic protein itself) are administered subcutaneously. In one embodiment, the LNPs encoding the therapeutic protein (or therapeutic protein itself) are administered chronically to the subject.

In an embodiment, the sequential doses are administered within one month of each other. In some embodiments, sequential doses are administered within two weeks of one another. In further embodiments, sequential doses are administered within one week of one another. In other embodiments, sequential doses are administered within one day of each other In some embodiments, the therapeutic protein (e.g., as encoded by a polynucleotide such as an mRNA or employed in the form of the protein itself) is a secreted protein. In other embodiments, the protein is an intracellular protein. In a further embodiment, the protein is a membrane-bound protein.

In some embodiments, the immune response that promotes ADA involves activation of T cells, and the T cells are not activated in the subject to a level which promotes ADA. In further embodiments, intravenous administration of the LNP induces Treg cells. In another embodiment, the T cells participate in the maintenance of tolerance to the protein.

In other embodiments, the LNPs comprise a helper lipid, which comprises a polar moiety and a lipidic moiety, linked by a core moiety. In further embodiments, the LNPs are substantially free of phosphatidylcholine (PC). In additional embodiments, the LNPs are substantially free of phosphatidylserine (PS). In some embodiments, the helper lipid is a phosphatidyl choline analog. In other embodiments, the phosphatidyl choline analog comprises a modified PC head group, a modified PC core group, and/or a modified PC lipid tail. In some embodiments, the LNPs comprise oleic acid or an oleic acid analog. In other embodiments, the LNPs are substantially free of PEG or a PEGylated lipid.

In another embodiment, the LNPs further comprise a PEGylated lipid. In some embodiments, the PEGylated lipid is an alkyl-PEGylated lipid. In another embodiment, the PEGylated lipid is a methoxy-PEGylated lipid. In a further embodiment, the PEGylated lipid is DMG-PEG. In an additional embodiment, the PEGylated lipid is a hydroxy-PEGylated lipid. In some embodiments, the PEGlyated lipid is less than 0.5% (w/w). In other embodiments, the PEGylated lipid is less than 0.25% (w/w).

In some embodiments, the LNPs further comprise a cationic lipid. In other embodiments, the cationic lipid is MC3 or DLin-MC3-DMA. In other embodiments, the cationic lipid is Cmpd18.

In some embodiments, the LNPs further comprise a sterol. In other embodiments, the sterol is cholesterol.

In some embodiments, the LNPs are administered to the subject at multiple doses.

In some embodiments, the nucleic acid is an mRNA encoding the protein and the mRNA comprises at least one microRNA binding site for a microRNA expressed in immune cells. In further embodiments, the mRNA having at least one microRNA binding site causes unwanted immune cell activation to be reduced or inhibited in the subject.

In some embodiments, the mRNA is chemically modified mRNA.

In some embodiments, immune cell activation is decreased by at least 25%. In other embodiments, immune cell activation is decreased by at least 50%, e.g., as compared to exposure to LNP with a different composition or as compared to exposure to LNP via a different route, e.g., without one or more first IV administration(s). In another embodiment, immune cell activation is decreased without a corresponding decrease in expression of the protein encoded by the mRNA.

In one embodiment, the mRNA is unmodified. In some embodiments, the mRNA comprises a 5' UTR, a codon optimized open reading frame encoding the polypeptide of interest, a 3' UTR comprising the at least one microRNA binding site, and a 3' tailing region of linked nucleosides. In other embodiments, the mRNA comprises a 5' UTR and 3'UTR which are heterologous to the open reading frame.

In some embodiments, the mRNA is fully modified. In further embodiments, the mRNA comprises pseudouridine (ψ), pseudouridine (ψ) and 5-methyl-cytidine (m5C), 1-methyl-pseudouridine (m1ψ), 1-methyl-pseudouridine (m1ψ) and 5-methyl-cytidine (m5C), 2-thiouridine (s2U), 2-thiouridine and 5-methyl-cytidine (m5C), 5-methoxy-uridine (mo5U), 5-methoxy-uridine (mo5U) and 5-methyl-cytidine (m5C), 2'-O-methyl uridine, 2'-O-methyl uridine and 5-methyl-cytidine (m5C), N6-methyl-adenosine (m6A), N6-methyl-adenosine (m6A) and 5-methyl-cytidine (m5C), pseudouridine (ψ), N1-methylpseudouridine (m1ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof. In other embodiments, the mRNA comprises 1-methyl-pseudouridine (m1ψ), 5-methoxy-uridine (mo5U), 5-methyl-cytidine (m5C), pseudouridine (ψ), α-thio-guanosine, or α-thio-adenosine, or combinations thereof.

In some embodiments, the microRNA binding site binds a microRNA expressed in myeloid cells. In other embodiments, the microRNA binding site binds a microRNA expressed in plasmacytoid dendritic cells. In some embodiments, the microRNA binding site binds a microRNA expressed in macrophages. In other embodiments, the microRNA binding site is a miR-126 microRNA binding site. In another embodiment, the microRNA binding site is a miR-142 microRNA binding site. In further embodiments, the microRNA binding site is a miR-155 microRNA binding site.

In some embodiments, the protein is a therapeutic protein, e.g., a cytokine, growth factor, antibody, receptor or fusion protein.

In some embodiments, the mRNA comprises at least two microRNA binding sites. In other embodiments, at least one of the microRNA binding sites is a miR-126 microRNA binding site. In another embodiment, the mRNA comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27. In another embodiment, the mRNA comprises a miR-126 binding site and a miR-142 binding site.

In some embodiments, the mRNA comprises at least three microRNA binding sites. In further embodiments, at least one of the microRNA binding sites is a miR-126 microRNA binding site.

In some embodiments, the chemically modified mRNA comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27.

In some embodiments, the mRNA comprises at least four microRNA binding sites. In further embodiments, the mRNA comprises a miR-126 binding site, a miR-142-3p binding site, a miR-142-5p binding site, and a miR-155 binding site.

In some embodiments, a first dose of LNP comprises a polynucleotide encoding a therapeutic protein having at least one, two, three or four microRNA binding sites. In some embodiments, a second dose of LNP comprises a polynucleotide encoding a therapeutic protein having at least one, two, three or four microRNA binding sites. In some embodiments, a first and second or subsequent dose of LNP comprises a polynucleotide encoding a therapeutic protein having at least one, two, three or four microRNA binding sites.

In some embodiments, the codon optimized open reading frame encoding the protein comprises a stop codon and wherein the at least one microRNA binding site is located within the 3' UTR 1-100 nucleotides after the stop codon. In other embodiments, the codon optimized open reading frame encoding the polypeptide of interest comprises a stop codon and wherein the at least one microRNA binding site is located within the 3' UTR at least 50 nucleotides after the stop codon.

The present disclosure, in some aspects, includes a method in a subject of increasing a therapeutic index of a therapeutic regimen involving lipid nanoparticle (LNP)-mediated nucleic acid drug delivery, by non-intravenously (e.g., subcutaneously) administering LNPs comprising a nucleic acid encoding a therapeutic protein to the subject in multiple doses or a therapeutic regimen involving non-intravenously administering a therapeutic protein itself, each dose sequentially administered (e.g., within three weeks of another dose), wherein the LNPs or the therapeutic protein do not induce an immune response associated with reduced protein expression (or induce a lower immune response), such that an increased therapeutic index of the therapeutic regimen is achieved relative to administration of an LNP comprising a nucleic acid encoding a therapeutic protein (or administration of a therapeutic protein itself) that induces an immune response associated with reduced protein expression. As set forth above, the increased therapeutic index is achieved by using LNPs that result in reduced immune responses owing to their composition and/or by use of an intravenous tolerizing regime prior to administration of a therapeutic composition (e.g., an LNP comprising a polynucleotide or a therapeutic protein) via a non-intravenous route.

Another aspect of the present disclosure includes a pharmaceutical composition of a subcutaneous formulation comprising a lipid nanoparticle (LNP) comprising a cationic lipid, a PEG-lipid, a sterol, and a helper lipid and an mRNA encoding a protein incorporated therein, wherein the mRNA comprises at least one microRNA binding site for a microRNA expressed in immune cells, wherein the LNP and/or microRNA binding site increases a therapeutic index greater than 10% relative to a chemically modified mRNA encoding a protein alone.

In some embodiments, the LNP and/or microRNA binding site reduce or inhibit unwanted immune cell activation, thereby reducing accelerated blood clearance (ABC) and/or anti-drug antibody (ADA) and increasing the therapeutic index.

In some embodiments, the microRNA is abundant in the same or different cell type of interest. In another embodiment, the microRNA is abundant in multiple cell types of interest.

In some embodiments, the mRNA comprises at least one first microRNA binding site of a microRNA abundant in an immune cell of hematopoietic lineage and at least one second microRNA binding site is of a microRNA abundant in endothelial cells.

In some embodiments, the mRNA comprises at least one first microRNA binding site of a microRNA abundant in B cells and at least one second microRNA binding site of a microRNA abundant in endothelial cells. In other embodiments, the mRNA comprises at least one first microRNA binding site of a microRNA abundant in plasmacytoid dendritic cells and at least one second microRNA binding site of a microRNA abundant in endothelial cells. In further embodiments, the mRNA comprises multiple copies of a first microRNA binding site and at least one copy of a second microRNA binding site.

In some embodiments, the mRNA comprises 2 copies of the first microRNA binding site. In other embodiments, the mRNA comprises first and second microRNA binding sites of the same microRNA. In another embodiment, the microRNA binding sites are of the 3p and 5p arms of the same microRNA.

In some embodiments, the microRNA is selected from the group consisting of miR-126, miR-142, miR-144, miR-146, miR-150, miR-155, miR-16, miR-21, miR-223, miR-24, miR-27 and miR-26a. In other embodiments, the microRNA is selected from the group consisting of miR126-3p, miR-142-3p, miR-142-5p, and miR-155. In one embodiment, at least one microRNA binding site is a miR-126 binding site. In another embodiment, at least one microRNA binding site is a miR-142 binding site. In some embodiments, one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27. In other embodiments, the composition comprises at least one miR-126-3p binding site and at least one miR-142-3p binding site. In another embodiment, the composition comprises at least one miR-142-3p binding site and at least one 142-5p binding site.

In some embodiments, the composition comprises at least three different microRNA binding sites, wherein at least one of the microRNA binding sites is a miR-126 binding site. In other embodiments, the composition comprises at least three different microRNA binding sites, and at least one of the microRNA binding sites is a miR-142 binding site. In further embodiments, the composition comprises at least one miR-126-3p binding site, at least one miR-142-3p, and a third microRNA binding site for a microRNA selected from the group consisting of miR-146-3p, miR-146-5p, miR-155, miR-16, miR-21, miR-223, miR-24 and miR-27. In another embodiment, the composition comprises at least one miR-126-3p binding site, at least one miR-142-3p binding site, and at least one miR-155 binding site. In a further embodiment, the composition comprises at least one miR-126-3p binding site, at least one miR-142-3p binding site, at least one miR-142-5p binding site, and at least one miR-155 binding site.

Certain of the LNPs provided herein comprise a cationic lipid, a helper lipid, a structural lipid, and a stabilizer which may or may not be provided conjugated to another lipid.

The cationic lipid may be but is not limited to DLin-DMA, DLin-D-DMA, DLin-MC3-DMA, DLin-KC2-DMA and DODMA. The cationic lipid may be an ionizable lipid.

The structural lipid may be but is not limited to a sterol such as for example cholesterol.

The helper lipid in the LNP is an amphiphilic surface active lipid, or surfactant. In some embodiments it is a non-cationic lipid. The helper lipid may comprise at least one non-polar chain and at least one polar headgroup moiety. A helper lipid may also be referred to as a complementary lipid i.e. the lipid functions to "complement" the amino lipid and increase the fusogenicity of the bilayer to help endosomal escape. In some embodiments the non-polar chain is a lipid. In other embodiments it is a fatty acid of at least 8C. In exemplary embodiments, the helper lipid is non-naturally occurring (e.g., not naturally occurring in human subjects) or is exogenous.

Certain of the LNPs lack any phosphatidyl choline (PC) lipids (i.e., are free of phosphatidyl choline (PC)). Certain of the LNPs provided herein lack specific phosphatidyl choline lipids such as but not limiting to DSPC. Certain of the LNPs comprise a phosphatidyl choline analog, such analogs comprising modified head groups (e.g., a modified quaternary amine head group), modified core group, and/or modified lipid tail group. Such analogs may comprise a zwitterionic group that is a non-PC zwitterionic group.

Certain LNPs comprise other helper non-cationic lipids including for example oleic acid or oleic acid analogs. The helper lipid may be a lipid of Formula IV as provided herein.

The stabilizer may be polyethylene glycol (PEG). PEG may be conjugated to a lipid and thus may be provided as PEG-c-DOMG or PEG-DMG, for example. The stabilizer, whether provided in a conjugated or an unconjugated form, may comprise 1.5 mol % of the LNP, or it may comprise less than 0.5 mol % of the LNP. For example, it may comprise less than 0.4 mol %, less than 0.3 mol %, less than 0.2 mol %, or less than 0.1 mol %. Each possibility represents a separate embodiment of the present invention.

Certain of the LNPs provided herein comprise no or low levels of PEGylated lipids, including no or low levels of alkyl-PEGylated lipids, and may be referred to herein as being free of PEG or PEGylated lipid. Thus, some LNPs comprise less than 0.5 mol % PEGylated lipid. In some instances, PEG may be an alkyl-PEG such as methoxy-PEG. Still other LNPs comprise non-alkyl-PEG such as hydroxy-PEG, and/or non-alkyl-PEGylated lipids such as hydroxy-PEGylated lipids. Each possibility represents a separate embodiment of the present invention.

The PEGylated lipid may be a Cmpd396, Cmpd394, Cmpd397, or Cmpd395. Each possibility represents a separate embodiment of the present invention.

In some instances, the LNP may comprise about 50 mol % cationic lipid, 10 mol % helper lipid, 1.5 mol % PEGylated lipid, and 38.5 mol % structural lipid.

In some instances, the LNP may comprise about 50 mol % cationic lipid, 10 mol % helper lipid, less than 0.5 mol % PEGylated lipid, and 39.5 mol % structural lipid. Each possibility represents a separate embodiment of the present invention.

These and other embodiments and aspects will be discussed in greater detail herein. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

FIG. 9 shows IgM concentrations in serum two weeks (left) and four weeks (right) after SC hEPO administration in nude and wild-type mice.

DETAILED DESCRIPTION

Figure 1:
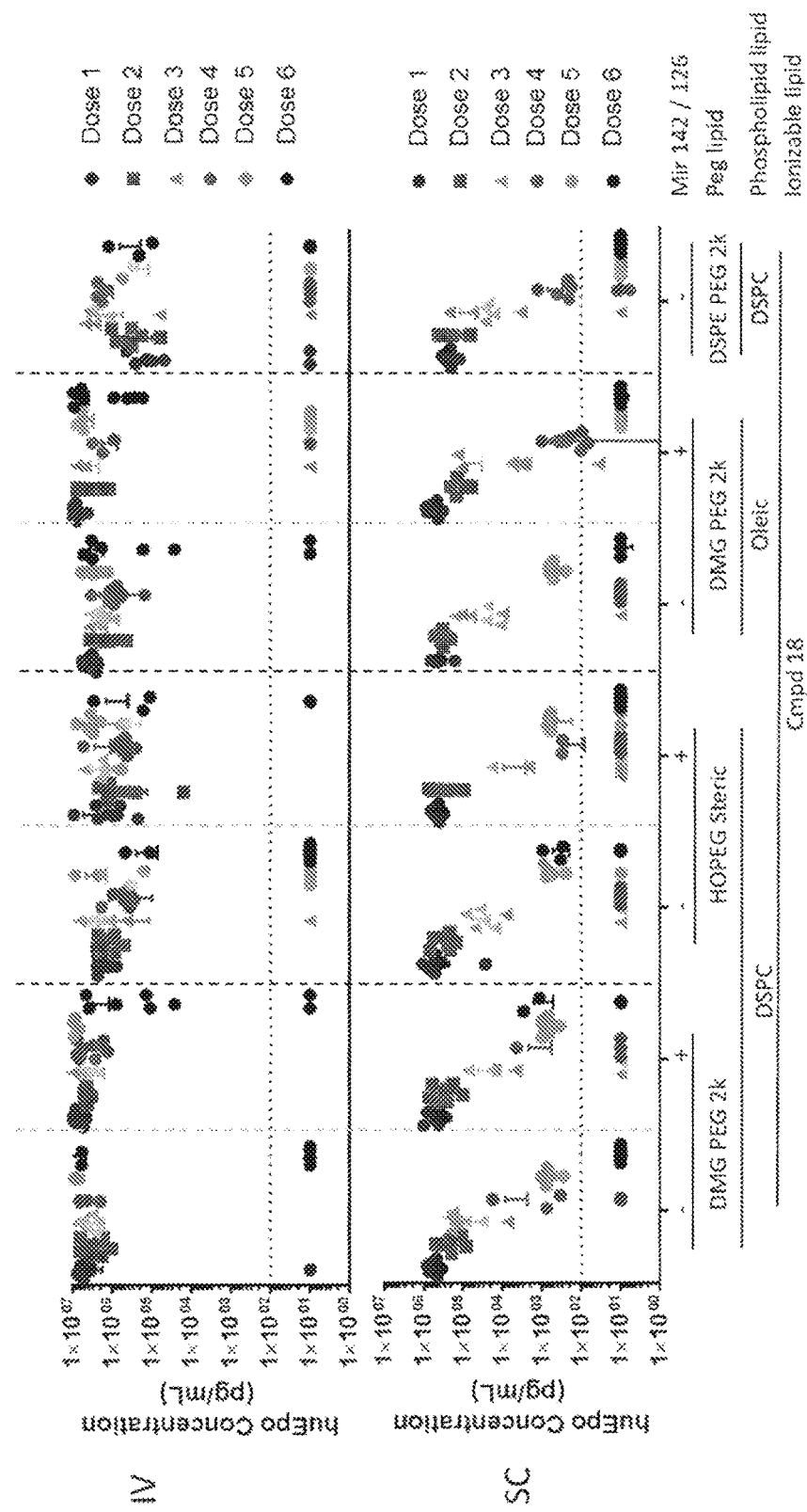
FIG. 1 consists of two graphs showing the effects of intravenous (IV) and subcutaneous (SC) administration of repeat doses of miR 142 and 126.

In one embodiment, this disclosure provides lipid-comprising compounds and compositions that have improved properties as well as methods of delivering these LNPs to reduce or eliminate immune responses to therapeutic proteins that are repetitively administered. While ordinarily nucleic acids such as mRNA formulated in LNPs are associated with delivery issues such as the development of an immune response (including ABC, ADA, toxicity, and lack of tolerance) that results in loss of functional protein expression from the RNA, the methods and products described herein are associated with enhanced properties leading to drug formulations with improved therapeutic index. The improved formulations may affect any one or more or all of ABC, ADA, toxicity, and lack of tolerance in a manner that results in more efficient delivery of drug to a subject with minimal toxic effect.

Lipid-comprising compounds and compositions are compositions that comprise or are conjugated to one or more lipids. These agents may be referred to herein as lipid-conjugated agents or lipidated agents or lipid nanoparticles (LNPs).

In another embodiment, this disclosure provides improved compounds and compositions for reducing or eliminating unwanted immune responses, ABC, ADA, lack of tolerance and toxicity upon in vivo administration and, in particular, upon subcutaneous administration. Subcutaneous administration of LNPs has been associated with expression problems in a multi dose therapeutic regimen. The data presented in the examples evaluated the effect of delivering a therapeutic nucleic acid by a subcutaneous (SC) route to a subject after delivering at least one IV dose to the subject. In particular the studies examined the effect of this dosing regimen (i.e., initial IV dosing followed by non-IV, e.g., SC dosing) on the development of tolerance. It was established that SC administration of LNP mRNA encoding a secreted protein resulted in an observed loss in protein expression at 4 weeks, and by 6 weeks all groups were at baseline. Additionally, the IV data was consistent with previous findings with little to no change in exposure over the 6 week time course, although there did seem to be a slight increase in 'non-responders' as the number of doses increased. However, quite surprisingly, when the animals were dosed SC after receiving at least one dose of LNP IV, protein expression levels were maintained over multiple doses, with the miR formulations showing less non-responders than non-miR formulations, although slightly below the first dose.

Also, surprisingly it was found that while subcutaneous administration of mRNA encoding secreted proteins resulted in protein loss after several rounds of administration, mRNA encoding intracellular proteins did not experience the same loss of protein expression. After 4 doses there was a slight loss in protein expression (activity), but significantly lower than that observed with secreted proteins.

Additionally the breadth of the immune response involved in the process of decreasing protein expression was demonstrated. Not only does the immune response contributing to protein loss involve B cells and cytokines, but T cells appear to play an important role. The data presented in the examples tests the effect of T-cells on the loss in protein expression by using nude mice (which lack T cells) as compared to wild type (WT) mice. After 4 doses the typical loss of protein expression and immune readouts in WT mice were observed. In contrast the nude mice all maintained protein expression regardless of formulation or dosing, anti-PEG IgM, or anti-drug antibodies. The data indicates that loss of protein expression is due at least in part to T cells. Further, in a separate experiment, anti-PEG IgM was found to be significantly increased in the group that did not receive intravenous predosing, indicating that the IV predosing regimen, even at different concentrations, influences the immune response to subsequent subcutaneous doses and decreases accelerate blood clearance (ABC) as discussed herein. The data presented in the examples also demonstrate that IV pre-dosed animals have higher levels of expression and lower levels of anti-drug antibodies (ADA) than those which receive SC dosing without IV predosing.

Accelerated Blood Clearance

One aspect of the invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus, a reduction in ABC refers to a reduction in observed clearance of circulating agent upon a second or subsequent dose of agent, relative to a standard LNP. The reduction may be, for instance, at least 10%, 15%, 20%, 25%, 300/%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively, the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

In one embodiment, the disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

In another embodiment, this disclosure provides a dosing administration protocol that results in reduced ABC which protocol involves first administering LNPs comprising a polynucleotide encoding a therapeutic protein intravenously one or more times. The protocol then involves subsequent administration of the same therapeutic protein or LNPs comprising a polynucleotide encoding the same therapeutic protein by a non-IV route one or more times.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively, one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophages are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 week time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects. In some embodiments the LNP has a typical PC, such as DSPC, and/or PEG.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, in one embodiment, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for Use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

Methods of Use for Reducing ABC

Also provided herein are methods for delivering LNPs, which may encapsulate an agent such as a nucleic acid encoding a therapeutic protein, to a subject without promoting ABC. In addition, methods of promoting tolerance to therapeutic proteins by initially administering LNPs comprising polynucleotides encoding the therapeutic protein via an intravenous route are provided.

In some embodiments, the method comprises administering any of the LNPs described herein, which do not promote ABC, for example, do not induce production of natural IgM binding to the LNPs, and do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production, and are a relative reduction to a reference value or condition. In some embodiments the reference value or condition is the amount of activation or induction of production of a molecule such as IgM by a standard LNP comprising a polynucleotide encoding a therapeutic protein (e.g., a standard LNP such as an MC3 LNP). In another embodiment, the reference value or condition is the amount of activation or induction of production of a molecule such as IgM by an LNP comprising a polynucleotide encoding a therapeutic protein when not initially administered by an IV route. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

In some instances, the LNPs described herein may be free of an epitope that activates B1a cells, for example, free of an epitope that activates or interacts with CD36 or CD6. Such LNPs contain either no epitopes capable of activating B1a cells or CD36 or contain such epitopes at a substantially low amount, which is not sufficient to activate B1a or CD36 to a level high enough for inducing substantial ABC. In other embodiments, the LNPs described herein may be free of an epitope that activates B1b cells. By substantially free of, it is meant that a LNP includes less than 99o/o of the recited agent. In some embodiments the LNP may include none of the recited agent. In some instances, the LNPs described herein may contain one or more helper lipid as described herein, which may comprise at least one fatty acid chain of at least 8C and at least one polar moiety. In some examples, the helper lipid does not activate B1a and/or B1b cells. In other examples, the helper lipid does not bind or has low binding affinity to CD36. Alternatively, the helper lipid may competitively inhibit phosphatidylcholine from binding to CD36.

Alternatively the LNP may be coadministered (administered with, before or after) or coformulated with an agent that removes or targets B or B1a cells. An agent that removes or targets B or B1a cells may be Rituximab. Rituximab (RITUXAN®, Genentech/Biogen) is a monoclonal antibody against the protein CD20, which is primarily found on the surface of immune system B cells. Rituximab interacts with CD20 on the surface of B cells and destroys B cells. As shown in the Examples, the combination of Rituximab and the LNP had significantly reduced ABC upon subsequent administration of LNP.

In other embodiments the agent may bind and/or inhibit CD6 on B1a cells. An exemplary agent that binds and/or inhibits CD6 on B1a cells is an anti-CD6 antibody, such as Alzumab. Alzumab (itolizumab, Biocon) is a humanized IgG1 monoclonal antibody that selectively targets CD6, a pan T cell marker involved in co-stimulation, adhesion and maturation of T cells. Alzumab also binds to CD6 on the surface of B1a cells.

In some instances the methods of the invention may comprise
(i) administering a first dose of an LNP comprising a polynucleotide encoding a therapeutic protein to a subject intravenously,
(ii) administering a second or subsequent dose of the therapeutic protein (or an LNP comprising a polynucleotide encoding the therapeutic protein) to the subject via a non-IV route, (optionally, the second or subsequent dose is administered within 2 weeks of the first or prior dose), and
(iii) repeating step (ii) one or more times,
wherein the agent is optionally formulated with an LNP that does not promote ABC.

In another embodiment, a method comprises:
(i) administering a first dose of an LNP comprising a polynucleotide encoding an intracellular protein to a subject,
(ii) administering a second or subsequent dose of the intracellular protein (or an LNP comprising a polynucleotide encoding the intracellular protein) to the subject via a non-IV route, (optionally, the second or subsequent dose is administered within two to three weeks of the first or prior dose), and
(iii) repeating step (ii) one or more times,
wherein the agent is optionally formulated with an LNP that does not promote ABC.

Another method for delivering an agent to a subject involves
(i) administering a first dose of an agent comprising an LNP formulated polynucleotide encoding a therapeutic protein to a subject intravenously,
(ii) administering a second or subsequent dose of the agent to the subject, wherein the second or subsequent dose is administered within 2 to 3 weeks of the first or prior dose, and
(iii) repeating step (ii) one or more times,
wherein the half-life of the agent after the second and subsequent dose is at least 50%, 60%, 70%, 80%, 85%, 90%, 95% or more of the half-life of the agent after the first dose.

In other aspects, a method for delivering an agent to a subject involves
(i) administering a first dose of an agent comprising an LNP formulated polynucleotide encoding an intracellular protein to a subject,
(ii) administering a second or subsequent dose of a therapeutic protein or polynucleotide encoding the therapeutic protein to the subject, wherein the second or subsequent dose is administered within 2 to 3 weeks of the first or prior dose, and
(iii) repeating step (ii) one or more times,
wherein the half-life of the agent after the second and subsequent dose is at least 500, 60%, 70%, 80%, 85%, 90%, 95% or more of the half-life of the agent after the first dose.

Still another method for delivering an agent to a subject involves
(i) administering a first dose of an agent comprising an LNP formulated polynucleotide encoding a therapeutic protein to a subject intravenously,
(ii) administering a second or subsequent dose of the agent to the subject, wherein the second or subsequent dose is administered within 2 to 3 weeks of the first or prior dose, and
(iii) repeating step (ii) one or more times,
wherein the activity or blood concentration of the agent after the second and subsequent dose is at least 50%, 60/o, 70%, 80%, 85%, 90%, 95% or more of the activity or blood concentration of the agent after the first dose.

Another method for delivering an agent to a subject involves
(i) administering a first dose of an agent comprising an LNP formulated polynucleotide encoding an intracellular protein to a subject to a subject,
(ii) administering a second or subsequent dose of a therapeutic protein or polynucleotide encoding the therapeutic protein to the subject, wherein the second or subsequent dose is administered within 2 weeks of the first or prior dose, and (iii) repeating step (ii) one or more times,
wherein the activity or blood concentration of the agent after the second and subsequent dose is at least 50%, 60%, 70%, 80%, 85%, 90/o, 95% or more of the activity or blood concentration of the agent after the first dose.

Second or subsequent doses of the agent may be the same agent or a different agent. Thus in some embodiments the first dose of agent may be a polynucleotide encoding an intracellular protein. In some embodiments the second dose of agent may be a polynucleotide encoding the intracellular protein. In other embodiments the second dose of agent may be a therapeutic protein. In some embodiments the intracellular protein is the therapeutic protein. In other embodiments the second dose of agent may be a polynucleotide encoding a therapeutic protein.

Second or subsequent doses may be administered within 6 months, 5 months, 4 months, 3 months, 2 months, 1 month, 4 weeks, 3 weeks, 2.5 weeks, 2 weeks, 1 week, or within 6 days, or within 5 days, or within 4 days, or within 3 days, or within 2 days, or within 1 day of the first or prior dose.

"Therapeutic protein" refers to a protein that, when administered to a subject has a therapeutic, diagnostic, and/or prophylactic effect and/or elicits a desired biological and/or pharmacological effect. Thus, the therapeutic protein may be any biologically active protein, such as a diagnostic agent or a therapeutic agent.

LNPs comprising polynucleotides encoding therapeutic proteins may be administered intravenously two or more times, three or more times, four or more times, etc. Agent administration may therefore be repeated once, twice, 3, 4, 5, 6, 7, 8, 9, 10, or more times. After the IV administration, therapeutic proteins or LNPs comprising polynucleotides encoding therapeutic proteins may be administered chronically or acutely, depending on its intended purpose.

The method may be a method of treating a subject having or at risk of having a condition that benefits from the biologically active agent, particularly if the biologically active agent is a therapeutic agent. Alternatively, the method may be a method of diagnosing a subject, in which case the biologically active agent is a diagnostic agent.

After the IV dosing, the second or subsequent doses of therapeutic protein via the non-IV route may maintain an activity of at least 50% of the activity of the first dose, or at least 60% of the first dose, or at least 70% of the first dose, or at least 75% of the first dose, or at least 80/o of the first dose, or at least 85% of the first dose, or at least 90% of the first dose, or at least 95% of the first dose, or more, for at least 1 day, 2 days, 3 days, 4 days, 5 days, 6 days, or 7 days post-administration of the second or subsequent dose.

When the biologically active agent is an mRNA (a therapeutic mRNA), a method for reducing ABC of LNPs encapsulating the mRNA can be performed using a low amount of the LNPs for the first dose, and/or the second dose (as well as the subsequent doses). The low doses can be equal to or less than 0.3 mg/kg, e.g., 0.2 mg/kg, or 0.1 mg/kg. In some instances, the first dose, the second dose, or both range from 0.1 to 0.3 mg/kg.

The interval between the first dose and the second dose in any of the methods described herein may be equal to or less than two weeks, for example, less than 21, 20, 19, 18, 17, 16, 15, 14, 13, 12, 11, 10, 9, 8, 7, 6, 5, 4, 3, 2 or 1 days. In some instances, the subject can be administered a dose once daily, every 2, 3, 4, 5, 6, 7, 8, 9, 10, 11, 12, 13, 14, 15, 16, 17, 18, 19, 20 or 21 days in any of the methods described herein. Each possibility represents a separate embodiment of the present invention.

Further, in one embodiment, inhibiting ABC of LNPs in a subject can be achieved by the use of one or more secondary agents that inhibit immune responses induced by LNPs, e.g., inhibit the binding to or activity of sensors e.g., natural IgM production, natural IgG production, activation of B1a cells, activation of B1b cells, and/or activation of platelets and or dendritic cells or the activity or production of any effectors. The secondary agents are to referred to alternatively as agents that inhibit immune responses induced by LNPs. In some instances, the secondary agent may inhibit the production of natural IgM that binds the LNPs, or neutralize such natural IgMs. In other instances, the secondary agent may inhibit activation of B1a cells or remove B1a cells. For example, such a secondary agent may inhibit a surface receptor of B1a cells, including, but not limited to CD36. Alternatively or in addition, the secondary agent may interfere with the binding of IgM to its target. In other embodiments, the secondary agent may inhibit the production of natural IgG that binds the LNPs, or neutralize such natural IgGs or may interfere with the binding of IgG to its target. In other instances, the secondary agent may inhibit activation of B1b cells or remove B1b cells.

Anti-Drug Antibody

It has been discovered according to the invention that IV dosing of an mRNA agent in an LNP (such mRNA optionally comprising a miR binding site) will inhibit an immune response associated with loss of protein expression associated with subsequent subcutaneous administration and can be used to provide repeated dosing of a subject with an LNP or the therapeutic protein itself during the window of susceptibility to ABC or ADA. Moreover, if the tolerance induced by IV administration wanes after repeated SC dosing, one or more additional IV doses can be administered in order to promote tolerance to further SC dosing. In this manner, repeated SC doses may be given while optimizing expression of the mRNA delivered.

Another challenge associated with LNP-nucleic acid delivery is the development of an unwanted anti-drug antibody (ADA) response, wherein an immune response generates antibodies against the therapeutic protein. Like ABC, the ADA response can interfere with or neutralize the effect of the therapeutic protein, thereby impacting drug pharmacokinetics and efficacy. Neutralizing antibodies (NAB) are generally of more concern than binding antibodies (BAB) that are not neutralizing, but both may have clinical consequences.

Furthermore, allergic reactions, complement activation and other adverse events are often associated with the development of ADA, thereby impacting drug safety. Thus, ADA is a significant factor in the ability to use biologics for long-term treatment.

Accordingly, the disclosure also provides methods for reducing or inhibiting an anti-drug antibody (ADA) response to a protein of interest by means of the administration of one or more IV doses of mRNA encoding the protein of interest in an LNP. This protocol results in induction of tolerance to the protein of interest (e.g., by post-transcriptional regulation, in particular in immune system tissue) and subsequent SC doses do not promote the same level of immune response as in a subject not given the initial IV dose(s) of the mRNA encoding the protein of interest in an LNP. The disclosure also provides methods of reducing drug-related toxicity in a subject by incorporation of at least one microRNA (miRNA) binding site for a miR expressed in immune cells into a mRNA (e.g., mmRNA) encoding a protein of interest. Preferred microRNA binding sites used in the methods of the disclosure are those that bind miRs expressed abundantly or preferentially in immune cells (e.g., in immune cells of peripheral lymphoid organs and/or splenocytes). A particularly preferred microRNA binding site is for miR-142-3p. Another particularly preferred microRNA binding site is for miR-126.

Another challenge associated with the clinical use of protein-based therapeutics in the art (whether delivered as proteins or as polynucleotides encoding proteins) is the development of unwanted immune cell activation (e.g., B cell activation) against the therapeutic protein, leading to immune-mediated side effects. It has now been discovered, however, that administration of mRNA, e.g., encoding a protein of interest, particularly in instances where the mRNA administration leads directly or indirectly to expression of the encoded protein in immune cells, e.g., splenocytes, also can lead to the development unwanted immune cell activation (e.g., B cell activation, including cytokine production). It has surprisingly been demonstrated, however, that administration of LNPs comprising polynucleotides that encode a therapeutic protein by the IV route, can reduce immune cell activation to the same protein (whether administered as a protein or as a polynucleotide encoding that protein in an LNP) when subsequently administered by a non-IV route. Incorporation of at least one binding site for a microRNA (miRNA) that is expressed in peripheral lymphoid tissue and/or endothelial cells, in particular at least one miR-126 and/or miR-142 binding site, into the mRNA (mRNA) can further reduce or inhibit unwanted immune cell activation when the mRNA is administered to the subject. Accordingly, the disclosure provides compositions and methods for reducing or inhibiting unwanted immune cell activation when using mRNA-based therapeutic proteins by means of post-transcriptional regulation, in particular in immune system tissue such as peripheral lymphoid organs or the spleen.

In one embodiment, the disclosure provides isolated RNAs, in particular mRNAs, e.g., chemically modified mRNAs, that encode a protein of interest and that include at least one microRNA binding site (e.g., miR-126 and/or miR-142 binding sites). In other embodiments, the disclosure provides RNAs, e.g., chemically modified RNAs, that include at least one microRNA binding site (e.g., miR-126 and/or miR-142 binding sites), but that do not necessarily encode a protein. The latter RNAs also may lack other typical features of mRNAs (such as the mRNA features described below), yet include the miR-126 and/or miR-142 binding site(s).

An RNA may be a naturally or non-naturally occurring RNA, e.g., mRNA. An mRNA may include one or more modified nucleobases, nucleosides, or nucleotides, as described below, in which case it may be referred to as a "chemically modified mRNA", also referred to herein as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'UTR), a 3' untranslated region (3'UTR), and/or a coding region (e.g., an open reading frame). An mRNA may include any suitable number of base pairs, including hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleotide or nucleobase type may be modified.

In one embodiment, the mRNA comprises a first flanking region located at the 5' terminus of an open reading frame (coding region) and a second flanking region located at the 3' terminus of the open reading frame (coding region), wherein the first flanking region comprises a 5' untranslated region (5' UTR) and the second flanking region comprises a 3' untranslated region (3'UTR). In one embodiment, the 5'UTR and the 3'UTR of the mRNA are not derived from the same species. In one embodiment, the 5'UTR and/or the 3'UTR of the mRNA are not derived from beta-globin. In one embodiment, the 5' untranslated region is heterologous to the coding region of the mRNA. In another embodiment, the 3' untranslated region is heterologous to the coding region of the mRNA. In yet another embodiment, the 5' untranslated region and the 3' untranslated region are heterologous to the coding region of the mRNA. In yet another embodiment, the mRNA comprises at least two stop codons.

The sequence of a non-limiting example of a 5' UTR suitable for use in the mRNA constructs is shown in SEQ ID NO: 53. The sequence of a non-limiting example of a 3' UTR suitable for use in the mRNA constructs is shown in SEQ ID NO: 30. Other suitable 5' and 3' UTRs suitable for use in the mRNA constructs are well known in the art.

For example, suitable 5' UTRs include those from the β-globin gene (see e.g., Kariko et al. (2008) *Mol. Therap.* 16:1833-40; U.S. Pat. Nos. 8,278,063, 9,012,219), the α-globin gene (see e.g., U.S. Pat. No. 9,012,219), the human cytochrome b-245 α polypeptide gene (CYBA) (see e.g., Ferizi et al. (2015) *Lab. Chip.* 23:1456-1464), the hydroxysteroid (17-β) dehydrogenase gene (HSD17B4) (see e.g., Thess et al. (2015) *Mol. Therap.* 23:1456-1464; WO 2015/024667), the TOP gene (see e.g., WO2015/101414, WO2015/101415, WO2015/062738, WO2015/024667, WO2015/024667), the ribosomal protein Large 32 (L32) gene (see e.g., WO2015/101414, WO2015/101415, WO2015/062738) and the ATP51 gene (see e.g., WO2015/024667), as well as viral 5' UTRs, including those from Tobacco etch virus (TEV) (see e.g., Katalin et al. (2012) *Mol. Therap.* 20:948-953; U.S. Pat. Nos. 8,278,063, 9,012, 219), Venezuelan equine encephalitis virus (VEEV), (see e.g., Andries et al. (2015) *J. Control Release* 217:337-344) and the CMV immediate-early 1 (IE1) gene (see e.g., US2014/0206753, WO2014/089486, WO2013/185069, WO2014/144196, WO2014/152659, WO2014/152940, WO2014/152774, WO2014/153052). Synthetic 5' UTRs have been described and are also suitable for use (see e.g., Mandal and Rossi (2013) *Nat. Protocol* 5:68-82).

Figure 4:
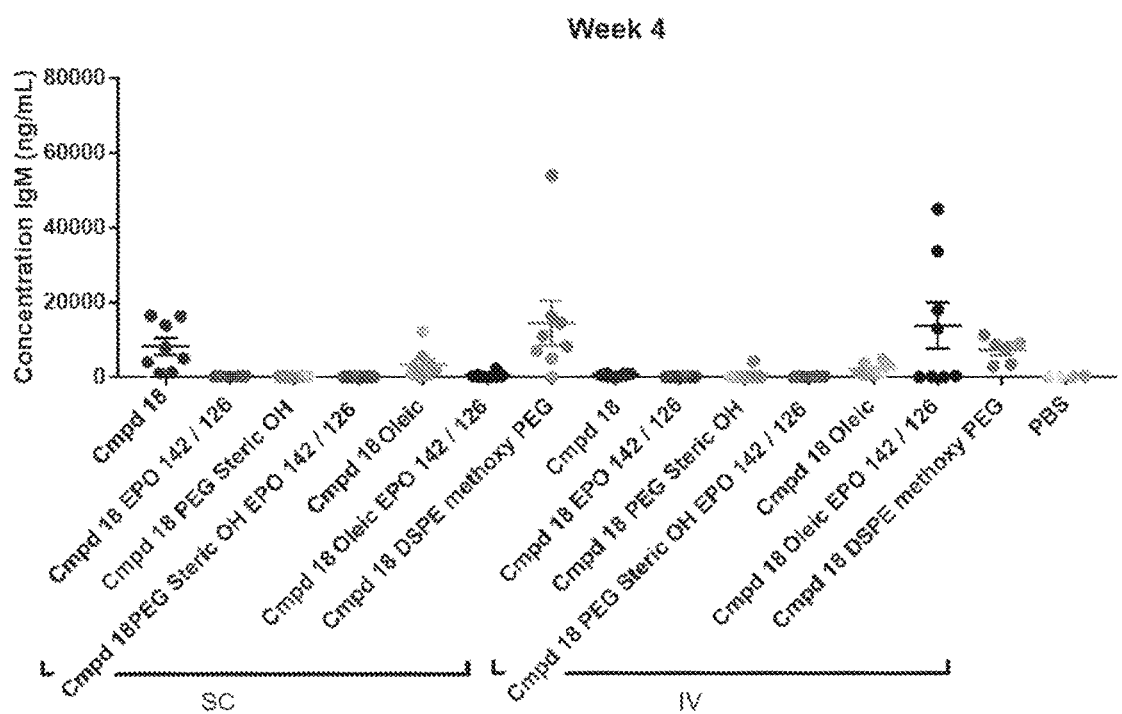
FIG. 4 shows the concentration of IgM in mice four weeks after SC or IV administration with the indicated formulations.

Additionally, for example, suitable 3' UTRs include those from the β-globin gene (see e.g., Kariko et al. (2008) *Mol. Therap.* 16:1833-40; U.S. Pat. Nos. 8,278,063; 9,012,219; WO2007/036366, US 2011/0065103, WO2011/015347, WO2012/072096, WO2013/143555, WO2014/071963), the α-globin gene (see e.g., U.S. Pat. No. 9,012,219; WO2015/101414, WO2015/101415, WO2015/024667), the human cytochrome b-245 α polypeptide gene (CYBA) (see e.g., Ferizi et al. (2015) *Lab. Chip.* 23:1456-1464), the albumin gene (see e.g., Thess et al. (2015) *Mol. Therap.* 23:1456-1464), the human growth hormone (hGH) gene (see e.g., US2014/0206753, WO2013/185069, WO2014/089486, WO2014/144196, WO2014/152659, WO2014/152940, WO2014/152774, WO2014/153052), the ribosomal rps9 protein gene (see e.g., WO2015/101414), the FIG. 4 gene (see e.g., WO2015/101415), the human albumin7 gene (see e.g., WO2015/101415, WO2015/101414, WO2015/006273, WO2015/024667, WO2105/062737), as well as viral 3' UTRs, including those from Venezuelan equine encephalitis virus (VEEV), (see e.g., Andries et al. (2015) *J. Control Release* 217:337-344).

In some embodiments, an mRNA as described herein may include a 5' cap structure, a chain terminating nucleotide, a Kozak sequence (also known as a Kozak consensus sequence), a stem loop, a polyA sequence, and/or a polyadenylation signal. In other embodiments, the mRNA lacks a polyA sequence and/or a polyadenylation signal but rather contains an alternative structure for stabilizing the mRNA.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m$^7$G(5')ppp (5')G, commonly written as m$^7$GpppG. A cap species may also be an anti-reverse cap analog. A non-limiting list of possible cap species includes m$^7$GpppG, m$^7$Gpppm$^7$G, m$^7$3'dGpppG, m$_2$$^{7,O3'}$GpppG, m$_2$$^{7,O3'}$GppppG, m$_2$$^{7,O2'}$GppppG, m$^7$Gpppm$^7$G, m$^7$3'dGpppG, m$_2$$^{7,O3'}$GpppG, m$_2$$^{7,O3'}$GppppG, and m$_2$$^{7,O2'}$GppppG. In various embodiments, the mRNA can comprise a 5' terminal cap selected from the group consisting of Cap0, Cap1, ARCA, inosine, N1-methyl-guanosine, 2'fluoro-guanosine, 7-deaza-guanosine, 8-oxo-guanosine, 2-amino-guanosine, LNA-guanosine, and 2-azido-guanosine. In one embodiment, the 5' terminal cap is Cap1.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

In one embodiment, the polynucleotides of the present disclosure may include a sequence encoding a self-cleaving peptide. The self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the *Thosea asigna* virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. As a non-limiting example, the 2A peptide may have the protein sequence: GSGATNFSLLKQAGDVEENPGP (SEQ ID NO: 4), fragments or variants thereof. In one embodiment, the 2A peptide cleaves between the last glycine and last proline. As another non-limiting example, the polynucleotides of the present disclosure may include a polynucleotide sequence encoding the 2A peptide having the protein sequence GSGATNFSL LKQAGDVEENPGP (SEQ ID NO: 4) fragments or variants thereof. One example of a polynucleotide sequence encoding the 2A peptide is: GGAAGCGGAGC-TACTAACTTCAG CCTGCTGAAGCAGGCTGGA-GACGTGGAGGAGAACCCTGGACCT (SEQ ID NO: 5). In one illustrative embodiment, a 2A peptide is encoded by the following sequence: 5'-TCCG GACTCAGATCCGGG-GATCTCAAAATTGTCGCTCCTGTCAAACAAACTCT-TAACTT TGATTTACTCAAACTGGCTGGG-GATGTAGAAAGCAATCCAGGTCCACTC-3' (SEQ ID NO: 6). The polynucleotide sequence of the 2A peptide may be modified or codon optimized by the methods described herein and/or are known in the art.

In one embodiment, this sequence may be used to separate the coding regions of two or more proteins. As a non-limiting example, the sequence encoding the 2A peptide may be between a first coding region A and a second coding region B (A-2Apep-B). The presence of the 2A peptide results in the cleavage of one long protein into protein A, protein B and the 2A peptide. Protein A and protein B may be the same or different peptides or proteins.

microRNAs (or miRNA) are 19-25 nucleotide long (commonly 19-23 nucleotides long, most typically 22 nucleotides long) noncoding RNAs that bind to the 3'UTR of nucleic acid molecules and post-translationally down-regulate gene expression either by reducing nucleic acid molecule stability or by inhibiting translation. The mRNAs of the disclosure may comprise one or more microRNA target sequences or sites, microRNA binding sequences or sites, sequence complementary to a microRNA sequences, or sequence complementary to a microRNA seed region or sequence. Such sequences may correspond to any known microRNA such as those taught in US Publication US2005/0261218 and US Publication US2005/0059005, the contents of which are incorporated herein by reference in their entirety. A microRNA sequence comprises a "seed" region or sequence, i.e., a sequence in the region of positions 2-8 of the mature microRNA, which sequence has perfect Watson-Crick complementarity to the miRNA target sequence. The bases of the microRNA seed region or sequence have complete complementarity with the target sequence. microRNAs derive enzymatically from regions of RNA transcripts that fold back on themselves to form short hairpin structures often termed a pre-miRNA (precursor-miRNA). The pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (an RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives, "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

In some embodiments, an mRNA of the disclosure may include one or more microRNA (miRNA) binding sites. As used herein, the term "microRNA (miRNA) binding site" refers to a sequence within a polynucleotide, e.g., within a DNA or within an RNA transcript, that has sufficient complementarity to all or a region of a miRNA to interact with, associate with or bind to the miRNA. In exemplary embodiments, miRNA binding sites are included in mRNAs, for example, in the 5' UTR and/or 3' UTR of an mRNA. A miR binding site sequence having sufficient complementarity to the miR refers to a degree of complementarity sufficient to facilitate miR-mediated regulation of the mRNA, e.g., miR-mediated translational repression or degradation of the mRNA. In exemplary aspects of the disclosure, a miR binding site sequence having sufficient complementarity to the miR refers to a degree of complementarity sufficient to facilitate miR-mediated degradation of the mRNA, e.g., miR-guided RISC-mediated cleavage of mRNA. The miR binding site can have complementarity to, for example, a 19-25 nucleotide long miR sequence, to a 19-23 nucleotide long miR, most typically to a 22 nucleotide long miR sequence. A miR binding site may be complementary to only a portion of a miR, e.g., to a portion 1, 2, 3 or 4 nucleotides shorter that a naturally-occurring miR. Full or complete complementarity (e.g., fully complementary or completely complementary over all or a significant portion of a naturally-occurring miR) is preferred when the desired regulation is mRNA degradation. In some embodiments, a miRNA binding site includes a sequence that has complementarity (e.g., partial or complete complementarity) with an miRNA seed sequence. In particular embodiments, the miRNA binding site includes a sequence that has complete complementarity with a miRNA seed sequence. In some embodiments, a miRNA binding site includes a sequence that has complementarity (e.g., partial or complete complementarity) with a miRNA sequence. In particular embodiments, the miRNA binding site includes a sequence that has complete complementarity with a miRNA sequence. In some embodiments, a miRNA binding site has complete complementarity with a miRNA sequence but for 1, 2 or 3 nucleotide substitutions, terminal additions, and/or truncations.

One or more miR binding sequences can be incorporated in an mRNA of the disclosure for one or more of a variety of different purposes. For example, incorporation of one or more miRNA binding sites into an mRNA of the disclosure may target the molecule for degradation or reduced translation, provided the miRNA in question is available (e.g., expressed in a target cell or tissue.) In some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Representative miRNAs were selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. The miRNA set thus included miRs that may be responsible in part for the immunogenicity of these cells, and such that a corresponding miR-site incorporation in the mRNA could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) *PLoS One* 9:e102259; Landgraf, P. et al. (2007) *Cell* 129; 1401-1414; Bissels. U. et al. (2009) *RNA* 15:2375-2384. As is evidenced, any one miR-site incorporation in the 3'UTR and/or 5' UTR may mediate such effects in multiple cell types of interest (e.g., miR-142 is abundant in both B cells and dendritic cells).

It is beneficial to target the same cell type with multiple miRs and to incorporate binding sites to each of the 3p and 5p arm if both are abundant (e.g., both miR-142-3p and miR142-5p are abundant in hematopoietic stein cells). Thus, for example, in certain embodiments, an mRNA construct contains two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

It is also beneficial to combine various miRs such that multiple cell types of interest are targeted at the same time (e.g., miR-142 and miR-126 to target many cells of the hematopoietic lineage and endothelial cells). Thus, for example, in certain embodiments, an mRNA construct contains two or more (e.g., two, three, four or more) miR bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plasmacytoid dendritic cells/platelets/endothelial cells).

Accordingly, in one embodiment, to modulate immune responses, an mRNA can comprise one or more miR binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of an mRNA delivered in a lipid-comprising compound or composition, the mRNA can comprise one or more miR binding sequences that bind to one or more miRs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g., reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

Such miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, the mRNA comprises at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the mRNA comprises 1-4, one, two, three or four miR binding sites for microRNAs expressed in immune cells. In another embodiment, the mRNA comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the mRNA comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

For example, in one embodiment, the mRNA comprises three copies of the same miR binding site. As described in Example 8, in certain embodiments, use of three copies of the same miR binding site can exhibit beneficial properties as compared to use of a single miR binding site. Non-limiting examples of sequences for 3' UTRs containing three miR bindings sites are shown in SEQ ID NO: 38 (three miR-142-3p binding sites), SEQ ID NO: 40 (three miR-142-5p binding sites) and SEQ ID NO: 54 (three miR-122 binding sites).

In another embodiment, the mRNA comprises two or more (e.g., two, three, four) copies of at least two different miR binding sites expressed in immune cells. Non-limiting examples of sequences of 3' UTRs containing two or more different miR binding sites are shown in SEQ ID NO: 33 (one miR-142-3p binding site and one miR-126-3p binding site), SEQ ID NO: 47 (one miR-142-3p binding site and one miR-122-5p binding site), SEQ ID NO: 41 (two miR-142-5p binding sites and one miR-142-3p binding sites) and SEQ ID NO: 44 (two miR-155-5p binding sites and one miR-142-3p binding sites).

In another embodiment, the mRNA comprises at least two miR binding sites for microRNAs expressed in immune cells, wherein one of the miR binding sites is for miR-142-3p. In various embodiments, the mRNA comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the mRNA comprises at least two miR binding sites for microRNAs expressed in immune cells, wherein one of the miR binding sites is for miR-126-3p. In various embodiments, the mRNA comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the mRNA comprises at least two miR binding sites for microRNAs expressed in immune cells, wherein one of the miR binding sites is for miR-142-5p. In various embodiments, the mRNA comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the mRNA comprises at least two miR binding sites for microRNAs expressed in immune cells, wherein one of the miR binding sites is for miR-155-5p. In various embodiments, the mRNA comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

In exemplary embodiments, the one or more miR binding sites are positioned within the 3'UTR, the 5' UTR, or both the 3' and 5' UTRs, such that the mRNA has the desired properties. The miR binding site can be positioned within the 3' UTR immediately following the stop codon of the coding region within the mRNA construct (or, if there are multiple copies of a stop codon in the construct, immediately following the final stop codon) or the miR binding site(s) can be positioned further downstream of the stop codon, in which case there are 3' UTR bases between the stop codon and the miR binding site(s). For example, three non-limiting examples of possible insertion sites for a miR in a 3' UTR are shown in SEQ ID NOs: 48, 49 and 50, which show a 3' UTR sequence with a miR-142-3p site inserted in one of three different possible insertion sites, respectively, within the 3' UTR. Furthermore, one or more miR binding sites can be positioned within the 5' UTR at one or more possible insertion sites. For example, three non-limiting examples of possible insertion sites for a miR in a 5' UTR are described further in Example 9 and shown in SEQ ID NOs: 55, 56 and 57, which show a 5' UTR sequence with a miR-142-3p site inserted into one of three different possible insertion sites, respectively, within the 5' UTR. Additionally, SEQ ID NOs: 58, 59 and 60 show a 5' UTR sequence with a miR-122 site inserted into one of three different possible insertion sites, respectively, within the 5' UTR.

In one embodiment, a codon optimized open reading frame encoding a protein comprises a stop codon and the at least one microRNA binding site is located within the 3' UTR 1-100 nucleotides after the stop codon. In one embodiment, the codon optimized open reading frame encoding the protein comprises a stop codon and the at least one microRNA binding site for a miR expressed in immune cells is located within the 3' UTR 30-50 nucleotides after the stop codon. In another embodiment, the codon optimized open reading frame encoding the protein comprises a stop codon and the at least one microRNA binding site for a miR expressed in immune cells is located within the 3' UTR at least 50 nucleotides after the stop codon. In other embodiments, the codon optimized open reading frame encoding the protein comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3'UTR comprises more than one miR binding site (e.g., 2-4 miR binding sites), wherein there can be a spacer region (e.g., of 10-100, 20-70 or 30-50 nucleotides in length) between each miR binding site. In another embodiment, the 3' UTR comprises a spacer region between the end of the miR binding site(s) and the poly A tail nucleotides. For example, a spacer region of 10-100, 20-70 or 30-50 nucleotides in length can be situated between the end of the miR binding site(s) and the beginning of the poly A tail.

In one embodiment, a codon optimized open reading frame encoding a protein comprises a start codon and the at least one microRNA binding site is located within the 5' UTR 1-100 nucleotides before (upstream of) the start codon. In one embodiment, the codon optimized open reading frame encoding the protein comprises a start codon and the at least one microRNA binding site for a miR expressed in immune cells is located within the 5' UTR 10-50 nucleotides before (upstream of) the start codon. In another embodiment, the codon optimized open reading frame encoding the protein comprises a start codon and the at least one microRNA binding site for a miR expressed in immune cells is located within the 5' UTR at least 25 nucleotides before (upstream of) the start codon. In other embodiments, the codon optimized open reading frame encoding the protein comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5'UTR comprises more than one miR binding site (e.g., 2-4 miR binding sites), wherein there can be a spacer region (e.g., of 10-100, 20-70 or 30-50 nucleotides in length) between each miR binding site.

In one embodiment, the 3' UTR comprises more than one stop codon, wherein at least one miR binding site is positioned downstream of the stop codons. For example, a 3' UTR can comprise 1, 2 or 3 stop codons. Non-limiting examples of triple stop codons that can be used include: UGAUAAUAG, UGAUAGUAA, UAAUGAUAG, UGAUAAUAA, UGAUAGUAG, UAAUGAUGA, UAAUAGUAG, UGAUGAUGA, UAAUAAUAA and UAGUAGUAG. Within a 3' UTR, for example, 1, 2, 3 or 4 miR binding sites, e.g., miR-142-3p binding sites, can be positioned immediately adjacent to the stop codon(s) or at any number of nucleotides downstream of the final stop codon. When the 3' UTR comprises multiple miR binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID Nos: 31 and 48-50.

In one embodiment, the mmRNA comprises a 5' UTR, a codon optimized open reading frame encoding a protein, a 3' UTR comprising the at least one microRNA binding site for a miR expressed in immune cells, and a 3' tailing region of linked nucleosides. In various embodiments, the 3' UTR comprises 1-4, at least two, one, two, three or four microRNA binding sites for miRs expressed in immune cells, preferably abundantly or preferentially expressed in immune cells.

In one embodiment, the at least one miR expressed in immune cells is a miR-142-3p microRNA binding site. In one embodiment, the miR-142-3p microRNA binding site comprises the sequence shown in SEQ ID NO: 3. In one embodiment, the 3' UTR of the mRNA comprising the miR-142-3p microRNA binding site comprises the sequence shown in SEQ ID NO: 2.

In one embodiment, the at least one miR expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 26. In one embodiment, the 3' UTR of the mmRNA comprising the miR-126-3p microRNA binding site comprises the sequence shown in SEQ ID NO: 27.

Non-limiting exemplary sequences for miRs to which a microRNA binding site(s) of the disclosure can bind include the following: miR-142-3p (SEQ ID NO: 8), miR-142-5p (SEQ ID NO: 9), miR-146-3p (SEQ ID NO: 10), miR-146-5p (SEQ ID NO: 11), miR-155-3p (SEQ ID NO: 12), miR-155-5p (SEQ ID NO: 13), miR-126-3p (SEQ ID NO: 14), miR-126-5p (SEQ ID NO: 15), miR-16-3p (SEQ ID NO: 16), miR-16-5p (SEQ ID NO: 17), miR-21-3p (SEQ ID NO: 18), miR-21-5p (SEQ ID NO: 19), miR-223-3p (SEQ ID NO: 20), miR-223-5p (SEQ ID NO: 21), miR-24-3p (SEQ ID NO: 22), miR-24-5p (SEQ ID NO: 23), miR-27-3p (SEQ ID NO: 24) and miR-27-5p (SEQ ID NO: 25). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In yet other embodiments, the therapeutic window and/or differential expression (e.g., tissue-specific expression) of a polypeptide of the disclosure may be altered by incorporation of a miRNA binding site into an mRNA encoding the polypeptide. Examples of tissues where microRNA are known to regulate mRNA, and thereby protein expression, include, but are not limited to, liver (e.g., miR-122), muscle (e.g., miR-133, miR-206, and miR-208), endothelial cells (e.g., miR-17-92, and miR-126), myeloid cells (e.g., miR-142-3p, miR-142-5p, miR-16, miR-21, miR-223, miR-24, and miR-27), adipose tissue (e.g., let-7, and miR-30c), heart (e.g., miR-1d and miR-149), kidney (e.g., miR-192, miR-194, and miR-204), and lung epithelial cells (e.g., let-7, miR-133, and miR-126). Thus, in various embodiments, an mRNA can comprise one or more binding site for any of the afore-mentioned miRs, alone or in combination, to regulate thereby regulate tissue expression of an encoded protein of interest.

For example, an mRNA may include one or more miRNA binding sites that are bound by miRNAs that have higher expression in one tissue type as compared to another. In another example, an mRNA may include one or more miRNA binding sites that are bound by miRNAs that have lower expression in a cancer cell as compared to a non-cancerous cell of the same tissue of origin. When present in a cancer cell that expresses low levels of such an miRNA, the polypeptide encoded by the mRNA typically will show increased expression. If the polypeptide is able to induce apoptosis, this may result in preferential cell killing of cancer cells as compared to normal cells.

For example, liver cancer cells (e.g., hepatocellular carcinoma cells) typically express low levels of miR-122 as compared to normal liver cells. Therefore, an mRNA encoding a polypeptide that includes at least one miR-122 binding site (e.g., in the 3'-UTR of the mRNA) will typically express comparatively low levels of the polypeptide in normal liver cells and comparatively high levels of the polypeptide in liver cancer cells. If the polypeptide is able to induce apoptosis, this can cause preferential cell killing of liver cancer cells (e.g., hepatocellular carcinoma cells) as compared to normal liver cells.

Accordingly, as a non-limiting example of incorporation a miR binding site(s) into a mRNA to modulate tissue expression of an encoded protein of interest, mRNAs of the disclosure may include at least one miR-122 binding site. For example, a mRNA of the disclosure may include a miR-122 binding site that includes a sequence with partial or complete complementarity with a miR-122 seed sequence. In some embodiments, a miR-122 seed sequence may correspond to nucleotides 2-7 of a miR-122. In some embodiments, a miR-122 seed sequence may be 5'-GGAGUG-3'. In some embodiments, a miR-122 seed sequence may be nucleotides 2-8 of a miR-122. In some embodiments, a miR-122 seed sequence may be 5'-GGAGUGU-3'. In some embodiments, the miR-122 binding site includes a nucleotide sequence of 5'-UAUUUAGUGUGAUAAUGGCGUU-3' (SEQ ID NO: 45) or 5'-CAAACACCAUUGUCACA-CUCCA-3' (SEQ ID NO: 46) or a complement thereof. In some embodiments, inclusion of at least one miR-122 binding site in an mRNA may dampen expression of a polypeptide encoded by the mRNA in a normal liver cell as compared to other cell types that express low levels of miR-122. In other embodiments, inclusion of at least one miR-122 binding site in an mRNA may allow increased expression of a polypeptide encoded by the mRNA in a liver cancer cell (e.g., a hepatocellular carcinoma cell) as compared to a normal liver cell.

In yet another embodiment, the mRNA (e.g., the 3' UTR thereof) can comprise at least one miR binding site for a miR expressed in immune cells, to thereby reduce or inhibit immune activation (e.g., B cell activation, cytokine production, ADA responses) upon nucleic acid delivery in vivo, and can comprise at least one miR binding site for modulating tissue expression of an encoded protein of interest. For example, in one embodiment, the mRNA comprises a miR-122 binding site, to thereby allow increased expression of a polypeptide encoded by the mRNA in a liver cancer cell (e.g., a hepatocellular carcinoma cell) as compared to a normal liver cell, and also comprises one or more miR binding sites for a miR expressed in immune cells, e.g., selected from the group consisting of miR-142, miR-146, miR-155, miR-126, miR-16, miR-21, miR-223, miR-24, miR-27.

In another embodiment, the mRNA (e.g., the 3' UTR thereof) can comprise at least one miR binding site to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miR binding site for modulating tissue expression of an encoded protein of interest. For example, in one embodiment, the mRNA comprises a miR-122 binding site, to thereby allow increased expression of a polypeptide encoded by the mRNA in a liver cancer cell (e.g., a hepatocellular carcinoma cell) as compared to a normal liver cell, and also comprises one or more miR binding sites, e.g., selected from the group consisting of miR-142, miR-146, miR-155, miR-126, miR-16, miR-21, miR-223, miR-24, miR-27.

In one embodiment, the mRNA comprises a miR-122 binding site and a miR-142-3p binding site. In another embodiment, the mRNA comprises a miR-122 binding site and a miR-142-5p binding site. In another embodiment, the mRNA comprises a miR-122 binding site and a miR-126-3p binding site. In another embodiment, the mRNA comprises a miR-122 binding site and a miR-155-5p binding site. In another embodiment, the mRNA comprises a miR-122 binding site and a miR-126-3p binding site. In another embodiment, the mRNA comprises a miR-122 binding site, a miR-142 (miR-142-3p or 142-5p) binding site and a miR-126 (miR-126-3p or miR-126-5p) binding site. In another embodiment, the mRNA comprises a miR-122 binding site, a miR-142 (miR-142-3p or 142-5p) binding site and a miR-155 (miR-155-3p or miR-155-5p) binding site. In another embodiment, the mRNA comprises a miR-122 binding site, a miR-126 (miR-126-3p or 126-5p) binding site and a miR-155 (miR-155-3p or miR-155-5p) binding site. In yet another embodiment, the mRNA comprises a miR-122 binding site, a miR-142 (miR-142-3p or miR-142-5p) binding site, a miR-126 (miR-126-3p or 126-5p) binding site and a miR-155 (miR-155-3p or miR-155-5p) binding site. In any of these embodiments, the miR-122 binding site can be a miR-122-5p binding site.

A non-limiting example of a 3' UTR sequence that comprises both a miR-142-3p binding site and a miR-122-5p binding site is shown in SEQ ID NO: 47. The structure of the 3' UTR of SEQ ID NO: 47 includes three stop codons at its 5' end, followed immediately by a single miR-142-3p binding site, followed downstream by spacer nucleotides and then a single miR-122-5p binding site. The distance between the miR binding sites (e.g., miR-142-3p and miR-122-5p) can vary considerably; a number of different constructs have been tested with differing placement of the two miR binding sites and all have been functional. In certain embodiments, a nucleotide spacer is positioned between the two miR binding sites of a sufficient length to allow binding of RISC to each one. In one embodiment, the two miR binding sites are positioned about 40 bases apart from each other and the overall length of the 3' UTR is approximately 100-110 bases.

ADA Assays

ADA assays (bioassays) can be used to assay for both neutralizing antibodies (NABs) and non-neutralizing, binding antibodies (BABs). NAB assays can include both cell based assays, for example, cell proliferation assays, biomarker assays, gene expression assays, gene reporter assays, antibody-dependent cell-mediated cytotoxicity (ADCC) assays, complement-dependent cytotoxicity (CDC) assays, and the like, as well as non-cell based assays, for example, competitive ligand-binding (CLBA) assays, surface plasmon resonance (SPR), enzyme-linked immunosorbent assay (ELISA), electro-chemiluminescence (ECL), e.g., electro-chemiluminescence immunoassay (ECLIA), dissociation-enhanced lanthanide fluorescent immunoassay (DELFIA®), Gyros® anti-drug antibody (ADA) immunoassays, fluorescent-enzyme immunoassay (FEIA), ristocetin-induced platelet aggregation (RIPA), and the like.

In exemplary aspects, the therapeutic regimen can include conducting one or more ADA assays before or during a therapeutic regimen. In exemplary embodiments, the ADA assay is a NAB assay. In such instances, the bioassay should be related to product mechanism of action, otherwise the assay will not be informative as to the effect of NAB on clinical pharmacology. In preferred embodiments, cell-based NABs are featured in the therapeutic regimen of the disclosure. If neutralizing cell-based assays are not feasible/ available competitive ligand binding assays or alternatives may be suitable. However, when these are used, it is preferably demonstrated that the assays reflect neutralizing capacity/potential in an appropriate manner.

In addition to directly measuring the ADA response, the level of immune cell activation also can be evaluated as a measure of a developing antibody response. The level of immune cell activation can be evaluated by essentially any method established in the art for assessing immune cell activation, such as the frequency of an activated immune cell population, typically assessed by detection of cells expressing cell-surface activation markers, or levels of production of one or more cytokines indicative of immune cell activation. In one embodiment, the immune cell activation is B cell activation, wherein the level of B cell activation is determined by measuring the frequency of activated B cells, such as the frequency of activated B cells among the splenic B cell population. B cell surface markers indicative of B cell activation are well known in the art (see e.g., Maddalay, R. et al. (2010) *FEBS Letters* 584:4883-4894). In one embodiment, B cell activation is determined by frequency of $CD19^+$ $CD86^+$ $CD69^+$ B cells. In another embodiment, the immune cell activation is B cell activation, wherein the level of B cell activation is determined by cytokine secretion, such as by secretion of interleukin-6 (IL-6), tumor necrosis factor α (TNF-α) or interferon-γ (IFN-γ), e.g., in the serum of treated subjects. In one embodiment, B cell activation is determined by secretion of IL-6, e.g., in the serum of treated subjects. In other embodiments, the unwanted cytokine production that is reduced or inhibited is production of interleukin-6 (IL-6), tumor necrosis factor α (TNF-α) or interferon-γ (IFN-γ), e.g., in the serum of treated subjects. In another embodiment, the unwanted cytokine production that is reduced or inhibited is production of interleukin-6 (IL-6).

Summary of Some MIR Sequences

| SEQ ID NO: | Sequence |
|---|---|
| 1 | GGGAAAUAAGAGAGAAAAGAAGAGUAAGAAGAAAUAUAAGAGCCACCAUGGGAGUGCACGAGU GUCCCGCGUGGUUGUGGUUGCUGCUGUCGCUCUUGAGCCUCCCACUGGGACUGCCUGUGCUGG GGGCACCACCCAGAUUGAUCUGCGACUCACGGGUACUUGAGAGGUACCUUCUUGAAGCCAAAG AAGCCGAAAACAUCACAACCGGAUGCGCCGAGCACUGCUCCCUCAAUGAGAACAUUACUGUAC CGGAUACAAAGGUCAAUUUCUAUGCAUGGAAGAGAAUGGAAGUAGGACAGCAGGCCGUCGAAG UGUGGCAGGGGCUCGCGCUUUUGUCGGAGGCGGUGUUGCGGGGUCAGGCCCUCCUCGUCAACU CAUCACAGCCGUGGGAGCCCCUCCAACUUCAUGUCGAUAAAGCGGUGUCGGGGCUCCGCAGCU UGACGAUGUUGCUUCGGGCUCUGGGCGCACAAAAGGAGGCUAUUUCGCCGCCUGACGCGGCCU CCGCGGCACCCCUCCGAACGAUCACCGCGGACACGUUUAGGAAGCUUUUUAGAGUGUACAGCA AUUUCCUCCGCGGAAAGCUGAAAUUGUAUACUGGUGAAGCGUGUAGGACAGGGGAUCGCUGAU AAUAGGCUGGAGCCUCGGUGGCCAUGCUUCUUGCCCCUUGGGCUCCCCCCCAGCCCCUCCUCC |

| SEQ ID NO: | Sequence |
|---|---|
| | CCUUCCUGCACCCGUACCCCCUCCAUAAAGUAGGAAACACUACAGUGGUCUUUGAAUAAAGUC<br>UGAGUGGGCGGC<br>(EPO with miR 142-3p binding site) |
| 2 | GCUGGAGCCUCGGUGGCCAUGCUUCUUGCCCCUUGGGCCUCCCCCCAGCCCCUCCUCCCCUUC<br>CUGCACCCGUACCCCCUCCAUAAAGUAGGAAACACUACAGUGGUCUUUGAAUAAAGUCUGAGU<br>GGGCGGC<br>(3'UTR with miR 142-3p binding site) |
| 3 | UCCAUAAAGUAGGAAACACUACA<br>(miR 142-3p binding site) |
| 4 | GSGATNFSLLKQAGDVEENPGP<br>(2A peptide) |
| 5 | GGAAGCGGAGCTACTAACTTCAGCCTGCTGAAGCAGGCTGGAGACGTGGAGGAGAACCCTGGA<br>CCT<br>(polynucleotide encoding 2A peptide) |
| 6 | TCCGGACTCAGATCCGGGGATCTCAAAATTGTCGCTCCTGTCAAACAAACTCTTAACTTTGAT<br>TTACTCAAACTGGCTGGGGATGTAGAAAGCAATCCAGGTCCACTC<br>(polynucleotide encoding 2A peptide) |
| 7 | GGGAAAUAAGAGAGAAAAGAAGAGUAAGAAGAAAUAUAAGAGCCACCAUGGGAGUGCACGAGU<br>GUCCCGCGUGGUUGUGGUUGCUGCUGUCGCUCUUGAGCCUCCCACUGGGACUGCCUGUGCUGG<br>GGCACCACCCAGAUUGAUCUGCGACUCACGGGUACUUGAGAGGUACCUUCUUGAAGCCAAAG<br>AAGCCGAAAACAUCACAACCGGAUGCGCCGAGCACUGCUCCCUCAAUGAACAUUACUGUAC<br>CGGAUACAAAGGUCAAUUUCUAUGCAUGGAAGAGAAUGGAAGUAGGACAGGCCGUCGAAG<br>UGUGGCAGGGGCUCGCGCUUUUGUCGGAGGCGGUGUUGCGGGGUCAGGCCCUCCUCGUCAACU<br>CAUCACAGCCGUGGGAGCCCCUCCAACUUCAUGUCGAUAAAGCGGUGUCGGGGCUCCGCAGCU<br>UGACGACGUUGCUUCGGGCUCUGGGCGCACAAAAGGAGGCUAUUUCGCCGCCUGACGCGGCCU<br>CCGCGGCACCCCUCCGAACGAUCACCGCGGACACGUUUAGGAAGCUUUUUAGAGUGUACAGCA<br>AUUUCCUCCGCGGAAAGCUGAAAUUGUAUACUGGUGAAGCGUGUAGGACAGGGGAUCGCUGAU<br>AAUAGGCUGGAGCCUCGGUGGCCAUGCUUCUUGCCCCUUGGGCCUCCCCCCAGCCCCUCCUCC<br>CCUUCCUGCACCCGUACCCCCGUGGUCUUUGAAUAAAGUCUGAGUGGGCGGC<br>(human EPO no miR binding sites) |
| 8 | UGUAGUGUUUCCUACUUUAUGGA<br>(miR 142-3p sequence) |
| 9 | CAUAAAGUAGAAAGCACUACU<br>(miR 142-5p sequence) |
| 10 | CCUCUGAAAUUCAGUUCUUCAG<br>(miR 146-3p sequence) |
| 11 | UGAGAACUGAAUUCCAUGGGUU<br>(miR 146-5p sequence) |
| 12 | CUCCUACAUAUUAGCAUUAACA<br>(miR 155-32 sequence) |
| 13 | UUAAUGCUAAUCGUGAUAGGGGU<br>(miR 155-5p sequence) |
| 14 | UCGUACCGUGAGUAAUAAUGCG<br>(miR 126-3p sequence) |
| 15 | CAUUAUUACUUUUGGUACGCG<br>(miR 126-5p sequence) |
| 16 | CCAGUAUUAACUGUGCUGCUGA<br>(miR 16-3p sequence) |
| 17 | UAGCAGCACGUAAAUAUUGGCG<br>(miR 16-5p sequence) |
| 18 | CAACACCAGUCGAUGGGCUGU<br>(miR 21-3p sequence) |
| 19 | UAGCUUAUCAGACUGAUGUUGA<br>(miR 21-5p sequence) |
| 20 | UGUCAGUUUGUCAAAUACCCCA<br>(miR 223-3p sequence) |

| SEQ ID NO: | Sequence |
|---|---|
| 21 | CGUGUAUUUGACAAGCUGAGUU<br>(miR 223-5p sequence) |
| 22 | UGGCUCAGUUCAGCAGGAACAG<br>(miR 24-3p sequence) |
| 23 | UGCCUACUGAGCUGAUAUCAGU<br>(miR 24-5p sequence) |
| 24 | UUCACAGUGGCUAAGUUCCGC<br>(miR 27-3p sequence) |
| 25 | AGGGCUUAGCUGCUUGUGAGCA<br>(miR 27-5p sequence) |
| 26 | CGCAUUAUUACUCACGGUACGA<br>(miR 126-3p binding site) |
| 27 | UGAUAAUAGGCUGGAGCCUCGGUGGCCAUGCUUCUUGCCCCUUGGGCCUCCCCCCAGCCCCUC<br>CUCCCCUUCCUGCACCCGUACCCCC<u>CGCAUUAUUACUCACGGUACGA</u>GUGGUCUUUGAAUAAA<br><br>GUCUGAGUGGGCGGC<br>(3'UTR with miR 126-3p binding site) |
| 28 | GGGAAAUAAGAGAGAAAAGAAGAGUAAGAAGAAAUAUAAGAGCCACCAUGGGAGUGCACGAGU<br>GUCCCGCGUGGUUGUGGUUGCUGCUGUCGCUCUUGAGCCUCCCACUGGGACUGCCUGUGCUGG<br>GGGCACCACCCAGAUUGAUCUGCGACUCACGGGUACUUGAGAGGUACCUUCUUGAAGCCAAAG<br>AAGCCGAAAACAUCACAACCGGAUGCGCCGAGCACUGCUCCCUCAAUGAGAACAUUACUGUAC<br>CGGAUACAAAGGUCAAUUUCUAUGCAUGGAAGAGAAUGGAAGUAGGACAGCAGGCCGUCGAAG<br>UGUGGCAGGGGCUCGCGCUUUUGUCGGAGGCGGUGUUGCGGGGUCAGGCCCUCCUCGUCAACU<br>CAUCACAGCCGUGGGAGCCCCUCCAACUUCAUGUCGAUAAAGCGGUGUCGGGGCUCCGCAGCU<br>UGACGACGUUGCUUCGGGCUCUGGGCGCACAAAAGGAGGCUAUUUCGCCGCCUGACGCGGCCU<br>CCGCGGCACCCCUCCGAACGAUCACCGCGGACACGUUUAGGAAGCUUUUUAGAGUGUACAGCA<br>AUUUCCUCCGCGGAAAGCUGAAAUUGUAUACUGGUGAAGCGUGUAGGACAGGGGAUCGCUGAU<br>AAUAGGCUGGAGCCUCGGUGGCCAUGCUUCUUGCCCCUUGGGCCUCCCCCCAGCCCCUCCUCC<br>CCUUCCUGCACCCGUACCCCC<u>CGCAUUAUUACUCACGGUACGA</u>GUGGUCUUUGAAUAAAGUCU<br><br>GAGUGGGCGGC<br>(hEPO with miR 126-3p binding site) |
| 29 | GGGAAAUAAGAGAGAAAAGAAGAGUAAGAAGAAAUAUAAGAGCCACCAUGGGAGUGCACGAGU<br>GUCCCGCGUGGUUGUGGUUGCUGCUGUCGCUCUUGAGCCUCCCACUGGGACUGCCUGUGCUGG<br>GGGCACCACCCAGAUUGAUCUGCGACUCACGGGUACUUGAGAGGUACCUUCUUGAAGCCAAAG<br>AAGCCGAAAACAUCACAACCGGAUGCGCCGAGCACUGCUCCCUCAAUGAGAACAUUACUGUAC<br>CGGAUACAAAGGUCAAUUUCUAUGCAUGGAAGAGAAUGGAAGUAGGACAGCAGGCCGUCGAAG<br>UGUGGCAGGGGCUCGCGCUUUUGUCGGAGGCGGUGUUGCGGGGUCAGGCCCUCCUCGUCAACU<br>CAUCACAGCCGUGGGAGCCCCUCCAACUUCAUGUCGAUAAAGCGGUGUCGGGGCUCCGCAGCU<br>UGACGACGUUGCUUCGGGCUCUGGGCGCACAAAAGGAGGCUAUUUCGCCGCCUGACGCGGCCU<br>CCGCGGCACCCCUCCGAACGAUCACCGCGGACACGUUUAGGAAGCUUUUUAGAGUGUACAGCA<br>AUUUCCUCCGCGGAAAGCUGAAAUUGUAUACUGGUGAAGCGUGUAGGACAGGGGAUCGCUGAU<br>AAUAG<u>UCCAUAAAGUAGGAAACACUACAG</u>CUGGAGCCUCGGUGGCCAUGCUUCUUGCCCCUUG<br>GGCCUCCCCCCAGCCCCUCCCCUUCCUGCACCCGUACCCCC<u>CGCAUUAUUACUCACGGUA</u><br><br><u>CGAGUGGUCUUUGAAUAAAGUCUGAGUGGGCGGC</u><br>(hEPO with miR 142-3p and miR 126-3p binding sites) |
| 30 | TGATAATAGGCTGGAGCCTCGGTGGCCATGCTTCTTGCCCCTTGGGCCTCCCCCCAGCCCCTC<br>CTCCCCTTCCTGCACCCGTACCCCCGTGGTCTTTGAATAAAGTCTGAGTGGGCGGC<br>(3'UTR, no miR binding sites) |
| 31 | TGATAATAGGCTGGAGCCTCGGTGGCCATGCTTCTTGCCCCTTGGGCCTCCCCCCAGCCCCTC<br>CTCCCCTTCCTGCACCCGTACCCCC<u>TCCATAAAGTAGGAAACACTACAG</u>TGGTCTTTGAATAA<br>ACTCTGAGTGGGCGGC<br>(3' UTR with miR 142-3p binding site) |
| 32 | TGATAATAGGCTGGAGCCTCGGTGGCCATGCTTCTTGCCCCTTGGGCCTCCCCCCAGCCCCTC<br>CTCCCCTTCCTGCACCCGTACCCCC<u>GCATTATTACTCACGGTACGA</u>GTGGTCTTTGAATAAA<br><br>GTCTGAGTGGGCGGC<br>(3' UTR with miR 126-3p binding site) |
| 33 | TGATAATAG<u>TCCATAAAGTAGGAAACACTACAG</u>CTGGAGCCTCGGTGGCCATGCTTCTTGCCC<br>CTTGGGCCTCCCCCCAGCCCCTCCTCCCCTTCCTGCACCCGTACCCCC<u>CGCATTATTACTCAC</u> |

| SEQ ID NO: | Sequence |
|---|---|
| | <u>GGTACG</u>AGTGGTCTTTGAATAAAGTCTGAGTGGGCGGC<br>(3' UTR with miR 142-3p and miR 126-3p binding sites) |
| 34 | UUAAUGCUAAUUGUGAUAGGGGU<br>(miR 155-5p sequence) |
| 35 | ACCCCTATCACAATTAGCATTAA<br>(miR 155-5p binding site) |
| 36 | TGATAATAGGCTGGAGCCTCGGTGGCCATGCTTCTTGCCCCTTGGGCCTCCCCCAGCCCCTC<br>CTCCCCTTCCTGCACCCGTACCCCCGTGGTCTTTGAATAAAGTCTGAGTGGGCGGC<br>(3'UTR with no miR binding site) |
| 37 | UGAUAAUAGGCUGGAGCCUCGGUGGCCAUGCUUCUUGCCCCUUGGGCCUCCCCCAGCCCCUC<br>CUCCCCUUCCUGCACCCGUACCCCC<u>UCCAUAAAGUAGGAAACACUACAG</u>UGGUCUUUGAAUAA<br>AGUCUGAGUGGGCGGC<br>(3'UTR with miR 142-3p binding site) |
| 38 | TGATAATAGT<u>CCATAAAGTAGGAAACACTACAG</u>CTGGAGCCTCGGTGGCCATGCTTCTTGCCC<br>CTTGGGCCT<u>CCATAAAGTAGGAAACACTACAT</u>CCCCCCAGCCCCTCCTCCCCTTCCTGCACCC<br>GTACCCCC<u>TCCATAAAGTAGGAAACACTACAG</u>TGGTCTTTGAATAAAGTCTGAGTGGGCGGC<br>(3' UTR with 3 miR 142-3p binding sites) |
| 39 | TGATAATAGGCTGGAGCCTCGGTGGCCATGCTTCTTGCCCCTTGGGCCTCCCCCAGCCCCTC<br>CTCCCCTTCCTGCACCCGTACCCCC<u>AGTAGTGCTTTCTACTTTATG</u>GTGGTCTTTGAATAAAG<br><br>TCTGAGTGGGCGGC<br>(3'UTR with miR 142-5p binding site) |
| 40 | TGATAATAG*AGTAGTGCTTTCTACTTTATG*GCTGGAGCCTCGGTGGCCATGCTTCTTGCCCCT<br><br>TGGGCC*AGTAGTGCTTTCTACTTTATG*TCCCCCCAGCCCCTCCTCCCCTTCCTGCACCCGTAC<br><br>CCCC*AGTAGTGCTTTCTACTTTATG*GTGGTCTTTGAATAAAGTCTGAGTGGGCGGC<br>(3'UTR with 3 miR 142-5p binding sites) |
| 41 | TGATAATAG*AGTAGTGCTTTCTACTTTATG*GCTGGAGCCTCGGTGGCCATGCTTCTTGCCCCT<br><br>TGGGCCT<u>CCATAAAGTAGGAAACACTACAT</u>CCCCCCAGCCCCTCCTCCCCTTCCTGCACCCGT<br>ACCCCC*AGTAGTGCTTTCTACTTTATG*GTGGTCTTTGAATAAAGTCTGAGTGGGCGGC<br><br>(3'UTR with 2 miR 142-5p binding sites and 1 miR 142-3p binding site) |
| 42 | TGATAATAGGCTGGAGCCTCGGTGGCCATGCTTCTTGCCCCTTGGGCCTCCCCCAGCCCCTC<br>CTCCCCTTCCTGCACCCGTACCCCC*ACCCCTATCACAATTAGCATTAAG*TGGTCTTTGAATAA<br>AGTCTGAGTGGGCGGC<br>(3'UTR with miR 155-5p binding site) |
| 43 | TGATAATAG*ACCCCTATCACAATTAGCATTAAG*CTGGAGCCTCGGTGGCCATGCTTCTTGCCC<br>CTTGGGCC*ACCCCTATCACAATTAGCATTAAT*CCCCCCAGCCCCTCCTCCCCTTCCTGCACCC<br>GTACCCCC*ACCCCTATCACAATTAGCATTAAG*TGGTCTTTGAATAAAGTCTGAGTGGGCGGC<br>(3' UTR with 3 miR 155-5p binding sites) |
| 44 | TGATAATAG*ACCCCTATCACAATTAGCATTAAG*CTGGAGCCTCGGTGGCCATGCTTCTTGCCC<br>CTTGGGCCT<u>CCATAAAGTAGGAAACACTACAT</u>CCCCCCAGCCCCTCCTCCCCTTCCTGCACCC<br>GTACCCCC*ACCCCTATCACAATTAGCATTAAG*TGGTCTTTGAATAAAGTCTGAGTGGGCGGC<br>(3'UTR with 2 miR 155-5p binding sites and 1 miR 142-3p binding site) |
| 45 | UAUUUAGUGUGAUAAUGGCGUU<br>(miR 122 binding site) |
| 46 | CAAACACCAUUGUCACACUCCA<br>(miR 122 binding site) |
| 47 | TGATAATAGT<u>CCATAAAGTAGGAAACACTACAG</u>CTGGAGCCTCGGTGGCCATGCTTCTTGCCC<br>CTTGGGCC<u>CAAACACCATTGTCACACTCCAT</u>CCCCCCAGCCCCTCCTCCCCTTCCTGCACCCG<br>TACCCCCGTGGTCTTTGAATAAAGTCTGAGTGGGCGGC<br>(3'UTR with miR 142-3p and miR 122-5p binding sites) |
| 48 | TGATAATAGT<u>CCATAAAGTAGGAAACACTACAG</u>CTGGAGCCTCGGTGGCCATGCTTCTTGCCC<br>CTTGGGCCTCCCCCAGCCCCTCCTCCCCTTCCTGCACCCGTACCCCCGTGGTCTTTGAATAA<br>AGTCTGAGTGGGCGGC |

| SEQ ID NO: | Sequence |
|---|---|
| | (3'UTR with miR 142-3p binding site, P1 insertion) |
| 49 | TGATAATAGGCTGGAGCCTCGGTGGCTCCATAAAGTAGGAAACACTACACATGCTTCTTGCCC<br>CTTGGGCCTCCCCCCAGCCCCTCCTCCCCTTCCTGCACCCGTACCCCCGTGGTCTTTGAATAA<br>AGTCTGAGTGGGCGGC<br>(3'UTR with miR 142-3p binding site, P2 insertion) |
| 50 | TGATAATAGGCTGGAGCCTCGGTGGCCATGCTTCTTGCCCCTTGGGCCTCCATAAAGTAGGAA<br>ACACTACATCCCCCAGCCCCTCCTCCCCTTCCTGCACCCGTACCCCCGTGGTCTTTGAATAA<br>AGTCTGAGTGGGCGGC<br>(3'UTR with miR 142-3p binding site, P3 insertion) |
| 51 | AGUAGUGCUUUCUACUUUAUG<br>(miR-142-5p binding site) |
| 52 | GACAGUGCAGUCACCCAUAAAGUAGAAAGCACUACUAACAGCACUGGAGGGUGUAGUGUUUCC<br>UACUUUAUGGAUGAGUGUACUGUG<br>(miR-142) |
| 53 | GGGAAATAAGAGAGAAAAGAAGAGTAAGAAGAAATATAAGAGCCACC<br>(5' UTR) |
| 54 | TGATAATAGCAAACACCATTGTCACACTCCAGCTGGAGCCTCGGTGGCCATGCTTCTTGCCCC<br>TTGGGCCCAAACACCATTGTCACACTCCATCCCCCAGCCCCTCCTCCCCTTCCTGCACCCGT<br>ACCCCCAAACACCATTGTCACACTCCAGTGGTCTTTGAATAAAGTCTGAGTGGGCGGC<br>(3'UTR with 3X miR122 binding sites) |
| 55 | GGGAAATAAGAGAGTCCATAAAGTAGGAAACACTACAAGAAAAGAAGAGTAAGAAGAAATATAAG<br>AGCCACC<br>(5' UTR with miR142-3p binding site at position p1) |
| 56 | GGGAAATAAGAGAGAAAAGAAGAGTAATCCATAAAGTAGGAAACACTACAGAAGAAATATAAG<br>AGCCACC<br>(5' UTR with miR142-3p binding site at position p2) |
| 57 | GGGAAATAAGAGAGAAAAGAAGAGTAAGAAGAAATATAATCCATAAAGTAGGAAACACTACAG<br>AGCCACC<br>(5' UTR with miR142-3p binding site at position p3) |
| 58 | GGGAAATAAGAGCAAACACCATTGTCACACTCCAAGAAAAGAAGAGTAAGAAGAAATATAAGA<br>GCCACC<br>(5' UTR with miR122-3p binding site at position p1) |
| 59 | GGGAAATAAGAGAGAAAAGAAGAGTAACAAACACCATTGTCACACTCCAGAAGAAATATAAGA<br>GCCACC<br>(5' UTR with miR122-3p binding site at position p2) |
| 60 | GGGAAATAAGAGAGAAAAGAAGAGTAAGAAGAAATATAACAAACACCATTGTCACACTCCAGA<br>GCCACC<br>(5' UTR with miR122-3p binding site at position p3) |
| 61 | UGAUAAUAGUCCAUAAAGUAGGAAACACUACAGCUGGAGCCUCGGUGGCCAUGCUUCUUGCCC<br>CUUGGGCCUCCCCCCAGCCCCUCCUCCCCUUCCUGCACCCGUACCCCCGCAUUAUUACUCAC<br>GGUACGAGUGGUCUUUGAAUAAAGUCUGAGUGGGCGGC<br>(3' UTR with miR 142-3p and miR 126-3p binding sites) |
| 62 | ACCCCUAUCACAAUUAGCAUUAA<br>(miR 155-5p binding site) |
| 63 | UGAUAAUAGUCCAUAAAGUAGGAAACACUACAGCUGGAGCCUCGGUGGCCAUGCUUCUUGCCC<br>CUUGGGCCUCCAUAAAGUAGGAAACACUACAUCCCCCAGCCCCUCCUCCCCUUCCUGCACCC<br>GUACCCCCUCCAUAAAGUAGGAAACACUACAGUGGUCUUUGAAUAAAGUCUGAGUGGGCGGC<br>(3' UTR with 3 miR 142-3p binding sites) |
| 64 | UGAUAAUAGGCUGGAGCCUCGGUGGCCAUGCUUCUUGCCCCUUGGGCCUCCCCCCAGCCCCUC<br>CUCCCCUUCCUGCACCCGUACCCCC*AGUAGUGCUUUCUAUUUAUG*GUGGUCUUUGAAUAAAG<br>UCUGAGUGGGCGCC<br>(3'UTR with miR 142-5p binding site) |
| 65 | UGAUAAUAG*AGUAGUGCUUUCUAUUUAUG*GCUGGAGCCUCGGUGGCCAUGCUUCUUGCCCCU<br>UGGGCCA*GUAGUGCUUUCUAUUUAUG*UCCCCCAGCCCCUCUCCCCUUCCUGCACCCGUACC |

| SEQ ID NO: | Sequence |
|---|---|
| | CCC*AGUAGUGCUUUCUAUUUAUGG*UGGUCUUUGAAUAAAGUCUGAGUGGGCGGC<br>(3'UTR with 3 miR 142-5p binding sites) |
| 66 | UGAUAAUAG*AGUAGUGCUUUCUAUUUAUGG*CUGGAGCCUCGGUGGCCAUGCUUCUUGCCCCU<br>UGGGCCUCCAUAAAGUAGGAAACACUACAUCCCCCCAGCCCCUCCUCCCCUUCCUGCACCCGU<br>ACCCCC*AGUAGUGCUUUCUAUUUAUGG*UGGUCUUUGAAUAAAGUCUGAGUGGGCGGC<br>(3'UTR with 2 miR 142-5p binding sites and 1 miR 142-3p binding site) |
| 67 | UGAUAAUAGGCUGGAGCCUCGGUGGCCAUGCUUCUUGCCCCUUGGGCCUCCCCCAGCCCCUC<br>CUCCCCUCCUGCACCCGUACCCCC*ACCCCUAUCACAAUUAGCAUUAAGUGGUCUUUGAAAUAA<br>AGUCUGAGUGGGCGGC<br>(3'UTR with miR 155-5p binding site) |
| 68 | UGAUAAUAG*ACCCCUAUCACAAUUAGCAUUAAGCUGGAGCCUCGGUGGCCAUGCUUCUUGCCC<br>CUUGGGCCACCCCUAUCACAAUUAGCAUUAAUCCCCCCAGCCCCUCCUCCCCUUCCUGCACCC<br>GUACCCCCACCCCUAUCACAAUUAGCAUUAAGUGGUCUUUGAAUAAAGUCUGAGUGGGCGGC*<br>(3' UTR with 3 miR 155-5p binding sites) |
| 69 | UGAUAAUAG*ACCCCUAUCACAAUUAGCAUUAAGCUGGAGCCUCGGUGGCCAUGCUUCUUGCCC<br>CUUGGGCC*UCCAUAAAGUAGGAAACACUACAUCCCCCCAGCCCCUCCUCCCCUUCCUGCACCC<br>GUACCCCC*ACCCCUAUCACAAUUAGCAUUAAGUGGUCUUUGAAUAAAGUCUGAGUGGGCGGC*<br>(3'UTR with 2 miR 155-5p binding sites and 1 miR 142-3p binding site) |
| 70 | UGAUAAUAGGCUGGAGCCUCGGUGGC<u><u>UCCAUAAAGUAGGAAACACUACA</u></u>CAUGCUUCUUGCCC<br>CUUGGGCCUCCCCCAGCCCCUCCUCCCCUUCCUGCACCCGUACCCCCGUGGUCUUUGAAUAA<br>AGUCUGAGUGGGCGGC<br>(3'UTR with miR 142-3p binding site, P2 insertion) |
| 71 | UGAUAAUAGGCUGGAGCCUCGGUGGCCAUGCUUCUUGCCCCUUGGGCC<u><u>UCCAUAAAGUAGGAA<br>ACACUACAU</u></u>CCCCCAGCCCCUCCUCCCCUUCCUGCACCCGUACCCCCGUGGUCUUUGAAUAA<br>AGUCUGAGUGGGCGGC<br>(3'UTR with miR 142-3p binding site, P3 insertion) |
| 72 | GGGAAAUAAGAGU<u>CCAUAAAGUAGGAAACACUAC</u>AAGAAAAGAAGAGUAAGAAGAAAUAUAAG<br>AGCCACC<br>(5' UTR with miR142-3p binding site at position p1) |
| 73 | GGGAAAUAAGAGAGAAAAGAAGAGUAAU<u>CCAUAAAGUAGGAAACACUAC</u>AGAAGAAAUAUAAG<br>AGCCACC<br>(5' UTR with miR142-3p binding site at position p2) |
| 74 | GGGAAAUAAGAGAGAAAAGAAGAGUAAGAAGAAAUAUAAU<u>CCAUAAAGUAGGAAACACUACAG</u><br>AGCCACC<br>(5' UTR with miR142-3p binding site at position p3) |

Stop codon = bold
miR 142-3p binding site = underline
miR 126-3p binding site = bold underline
miR 122-5p binding site = double underline
miR 155-5p binding site = italicized
miR 142-5p binding site = italicized and bold underline

Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related pseudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

Platelet aggregation is observed soon after LNP administration, and appears to occur at the same time as or potentially before platelet activation as evidenced through increased expression of platelet activation markers such as CD31 and CD62P. LNPs that do not associate with significant numbers of platelets but which are able to activate platelets to a lesser degree than the more robust LNPs (discussed above) also cause platelet aggregation very early after administration, and presumably prior to platelet activation. Thus, in vivo, LNP association with platelets appears to occur at about the same time as aggregation of platelets, and presumably prior to the peak of platelet activation.

Also significant is the additional observation that a subset of LNPs is able to activate platelets, even without appreciable physical association with platelets. This subset is also able to form platelet aggregates comprising B cells and macrophages.

Certain LNPs have also been shown to stimulate early interaction between platelets (whether or not activated) and macrophages and B cells, thereby activating these latter cells as well. The effect of LNPs on B cells and macrophages is therefore both direct and indirect, but ultimately can lead to increased activation of such cells.

Activation of platelets could mediate complement activation. It is therefore contemplated that certain LNPs may induce dose-limiting toxicity such as CARPA and APR via activation of platelets and subsequently the complement system. Certain lipid components of LNPs, such as phosphatidylcholine may bind to and activate CD36 on platelets, which would trigger the TLR2/4/6 signaling, leading to aggregation and activation of the platelets. Activated platelets express CD62P (P selectin), which is a C3b-binding protein and can trigger the complement cascade. Activated platelets also recruit immune cells such as macrophages and neutrophils, which lead to further immune responses including cytokine (e.g., IL-6) secretion. Further, properdin was found to bind directly to activated platelet via, e.g., CD62P and recruits C3b or $C3(H_2O)$, thus triggering the alternative pathway. Saggu et al., J. Immunol. 190:6457-6467 (2013).

Accordingly, uses of LNPs that do not induce platelet activation and/or aggregation; and/or do not promote the activation of the complement system (e.g., the classic pathway and/or the alternative pathway) could reduce the risk of LNP-related toxicity. Such LNPs may not induce the activation of platelets and/or the complement system at all. Alternatively, such LNPs may induce a substantially low level of platelet activation and/or complement system activation, which is not sufficient to result in substantial dose-limiting toxicity.

Alternatively or in addition, secondary agents that block the initial platelet activation/aggregation, the initial activation of the complement system, and/or the downstream complement cascade, either in the classic pathway or in the alternative pathway, could be used to prevent or reduce LNP-related toxicity. In some instances, such a secondary agent may inhibit platelet activation, for example, inhibit CD36 activation triggered by LNPs. In other instances, the secondary agent may inhibit CARPA or ARP, for example, inhibit the classical pathway and/or the alternative pathway. Such a secondary agent may target at least one component in the complement system or proteins involved in ARP, thereby blocking the reaction cascade. For example, the secondary agent may be an antagonist of a TLR receptor (TLR2, TLR4, or TLR6), CD62P, CD31, properdin, a component of the complement system (e.g., C1q, C3a, C3b, C5a, and C5b). In yet other instances, the secondary agent may be an agent that can alleviate at least one symptom of LNP-related toxicity. Such agents include, but are not limited to, nonsteroidal anti-inflammatory drug (NSAID) or an antihistamine agent, which can be a histamine receptor blocker such as an H1 antagonist or an H1 inverse agonist.

In some embodiments, dose-limiting toxicity and/or ABC can be reduced in a subject being treated with a therapeutic regimen involving LNP-mediated drug delivery by using LNPs that do not activate a thrombospondin receptor (e.g., CD36), which may be expressed on the surface of immune cells (e.g., B1a or B1b cells); or other surface receptors involved in triggering the immune responses that lead to dose-limiting toxicity and/or ABC. Such LNPs may not activate the thrombospondin receptor at all, or could only induce a substantially low level of its activity such that it is insufficient to induce clinically significant dose-limiting toxicity and/or ABC. Alternatively or in addition, dose-limiting toxicity and/or ABC can be reduced in a subject being treated with a therapeutic regimen involving LNP-mediated drug delivery by using one or more secondary agent that inhibits the activity of a thrombospondin receptor (e.g., CD36) expressed on the surface of immune cells and platelets. The thrombospondins (TSP) are a family of multifunctional proteins that are expressed on the surface of or secreted by cells such as blood platelets. The family consists of thrombospondins 1-5. TSP-1 is an inhibitory ligand of CD36.

Based on these findings, this disclosure contemplates and provides LNPs as well as LNP-formulated active agents that have reduced platelet association and/or reduced platelet activation and/or reduced platelet aggregation activity. Use of such LNPs, for example as a delivery vehicle for an active agent, reduces the risk of developing coagulopathy, such as disseminated intravascular coagulation (DIC, also referred to as consumptive coagulopathy), whether acute or chronic, and/or vascular thrombosis, as well as any toxicity related thereto. If such toxicity is dose-limiting, then use of these LNPs will enable administration of higher LNP doses and more importantly will enable the delivery of higher doses of the active agent cargo carried by such LNP.

The diminution of the platelet response after LNP administration has additional desirable effects, some of which may be synergistic. LNPs have been reported to activate complement shortly after administration. This activation may be direct or indirect. For example, it has been reported that activated platelets are able to activate complement. Thus LNPs that reduce or prevent platelet activation will also indirectly reduce or prevent complement activation. Complement activation can also contribute to coagulation, for example through complement-mediated generation of thrombin. Thrombin converts available fibrinogen to fibrin, which in turn forms clots together with platelets. Activated platelets have thrombin receptors on their surface and therefore are able to recruit and/or raise the local concentration of thrombin, thereby enhancing fibrin production and ultimately clot formation. The disclosure therefore contemplates and provides additional LNPs that do not activate complement or do not activate complement to the same degree as existing LNPs. Yet still additional LNPs provided herewith are those that do not activate platelet and do not activate complement.

Similarly, this disclosure contemplates LNPs that interfere with properdin binding to platelets. Properdin is a positive regulator of the alternative pathway of the complement system. It has been shown to bind to activated platelets, thereby activating the alternative pathway in response to and in the vicinity of the activated platelet. Thus further contemplated is the use of a properdin inhibitors in combination with LNPs provided herein whether such LNPs activate or do not activate platelets, as defined below. Properdin inhibitors include DNA and sulfated glucoconjugates, both of which are bound by properdin and may interfere with properdin binding to activated platelets.

This disclosure therefore contemplates and provides, in some aspects, LNPs and LNP formulations that have reduced platelet effects including reduced platelet association and/or reduced platelet activation and/or reduced platelet aggregation activity. Certain LNPs may affect one, two or all three of these platelet activities. For example, some LNP may have reduced platelet association activity, or reduced platelet aggregation activity, or reduced platelet activation activity. Some LNP may have reduced platelet association activity and or reduced platelet activation activity, or reduced platelet association activity and reduced platelet activation activity, or reduced platelet aggregation activity and reduced platelet activation activity. Some LNP may have reduced platelet association activity, reduced platelet aggregation activity, and reduced platelet activation activity.

The disclosure contemplates that some LNPs may be universal LNPs, intending that they will down-modulate (or not stimulate in the first instance) one or more of the afore-mentioned platelet activities upon administration in the majority of patients or in all patients.

Additionally, the disclosure contemplates that some LNPs may in some instances be defined and thus identified as patient-specific. That is, some LNPs may be effective at down-regulating a platelet response, as described herein, in some but not all patients. Thus, in some instances, some LNPs and LNP formulations may be identified for particular patients and may then be used only for those particular patients.

In some instances, the findings provided herein may be applied directly to biologically active agents. For example, the biologically active agent that is a lipid or is conjugated to a lipid or that is conjugated to a PEG moiety directly or indirectly, may be modified as described herein to render the agent unable to stimulate a platelet response or cascade.

Platelet Activity Assays

These various activities may be measured as described herein and/or as performed in the art. For example, platelet activation may be assessed by increased expression of activation markers such as CD31 and CD62P. Platelet aggregation may be assessed by flow cytometry. Similarly flow cytometry may be used to detect non-platelet types such as B cells and macrophages within such aggregates. It is to be understood that the platelet effects of LNP can be assessed in vivo, for example in an animal model, as well as in vitro using for example human blood. These assays may be used to screen for and/or identify LNP having one or more of the afore-mentioned activities.

Compounds and Compositions, Including LNP

The disclosure provides lipid-comprising compositions that are less susceptible to clearance and thus have a longer half-life in vivo. This is particularly important where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which lipid-containing exogenously administered agents are rapidly cleared from the blood upon second and subsequent administrations. This phenomenon has been observed for a variety of lipid-containing compositions, including, but not limited to, liposomes, lipid nanoparticles, and lipid-encapsulated agents. Heretofore, the basis of ABC has been poorly understood and accordingly strategies for avoiding it have remained elusive.

The lipid-containing compositions of this disclosure, surprisingly, do not experience or are minimally affected by ABC upon second and subsequent administration in vivo. This resistance to ABC renders these compositions particularly suitable for repeated use in vivo, including for repeated use within short periods of time, including days or 1-2 weeks.

This resistance to ABC is due in part to the inability of these compositions to activate B1a cells. Such compositions are therefore referred to herein as B1a inert compositions or compositions that do not activate substantial B1a, intending that these compositions, when combined with B1a cells, do not activate B1a cells. Activation of B1a cells may be determined in a number of ways including, but not limited to, increased expression of activation markers such as CD86, and expression and/or secretion of cytokines. These compositions may or may not bind to B1a cells, and they may or may not bind to circulating IgM. Thus, these compositions may evade detection by circulating IgM and/or by B1a cells.

B1a cells are a subset of B cells involved in innate immunity. These cells are the source of circulating IgM, referred to as natural antibody or natural serum antibody. These IgM antibodies are characterized as having weak affinity for a number of antigens, and therefore they are referred to as "poly-specific" or "poly-reactive", describing their ability to bind to more than one antigen. Although able to produce such IgM, B1a cells are not capable of producing IgG. Additionally, they do not develop into memory cells and thus do not contribute to an adaptive immune response. However, they are able to secrete IgM upon activation. The secreted IgM is typically cleared within about 12 days (half-life of IgM in sera is about 5-8 days, *Nature Review Drug Discovery* 2, 52-62, January 2003), at which point the immune system is rendered relatively naïve to the previously administered antigen. If the same antigen is presented after this time period (e.g., at about 2 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic compositions unsuitable for repeated use.

The compounds, particles, and compositions described herein overcome these limitations, thereby transforming a variety of lipid-containing compositions into efficacious therapeutic and diagnostic agents. The B1a lipid-compositions provided herein do not undergo accelerated blood clearance upon repeat administration and thus can be administered repeatedly to a subject, including within short periods of time, without loss of activity.

Resistance to ABC may also be due in part to the inability of these compositions to activate B1b cells, pDC and/or platelets. Such compositions are therefore referred to herein as B1b pDC and/or platelets inert compositions or compositions that do not activate substantial B1b pDC and/or platelets, intending that these compositions, when combined with B1b cells pDC and/or platelets, do not activate B1b cells pDC and/or platelets, respectively. Activation of B1b cells, pDC and/or platelets may be determined in a number of ways including, but not limited to, increased expression of activation markers such as CD11b (for B1b cells), and expression and/or secretion of cytokines, and ability to activate B cells (pDC). These compositions may or may not bind to B1b cells, pDC and/or platelets, and they may or may not bind to circulating IgM or IgG. Thus, these compositions may evade detection by circulating IgM, IgG and/or by B1a cells pDC and/or platelets.

Particles, such as LNP, typically comprise one or more of the following components: lipids (which may include cationic lipids, helper lipids which may be neutral lipids, zwitterionic lipid, anionic lipids, and the like), structural lipids such as cholesterol or cholesterol analogs, fatty acids, polymers, stabilizers, salts, buffers, solvent, and the like.

In some embodiments, RNA (e.g., mRNA) of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016/000129; PCT/US2016/014280; PCT/US2016/014280; PCT/US2017/038426; PCT/US2014/027077; PCT/US2014/055394; PCT/US2016/052117; PCT/US2012/069610; PCT/US2017/027492; PCT/US2016/059575 and PCT/US2016/069491 all of which are incorporated by reference herein in their entirety.

RNA of the present disclosure may be formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound of Formula (I):

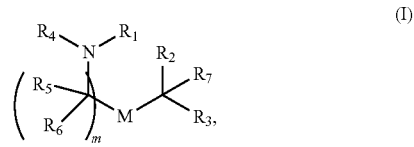

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl:

each Y is independently a C$_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when R$_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R—C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and C$_{1-3}$ alkyl, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{2-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{1-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{2-14}$ alkyl, C$_{2-14}$ alkenyl, —R*YR", R$_4$ is —(CH$_2$)$_n$Q or —(CH$_2$)$_n$CHQR, where Q is —N(R)$_2$, and n is selected from 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —CH$_2$)$_n$Q, —(CH$_2$)CHQR, —CHQR, and —CQ(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

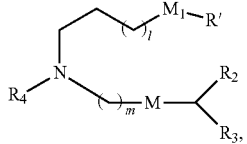

(IA)

or a salt or isomer thereof, wherein 1 is selected from 1, 2, 3, 4, and 5; m is selected from 5, 6, 7, 8, and 9; M$_1$ is a bond or M'; R$_4$ is unsubstituted C$_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (II):

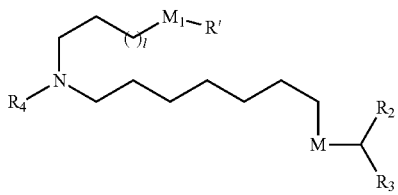

(II)

or a salt or isomer thereof, wherein 1 is selected from 1, 2, 3, 4, and 5; M$_1$ is a bond or M'; R$_4$ is unsubstituted C$_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (IIa), (IIb), (IIc), or (IIe):

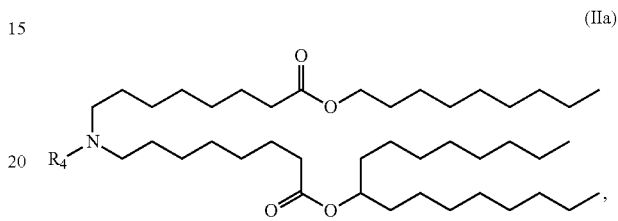

(IIa)

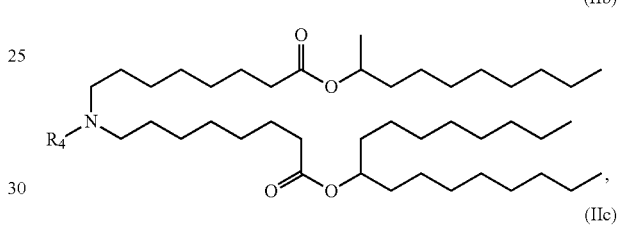

(IIb)

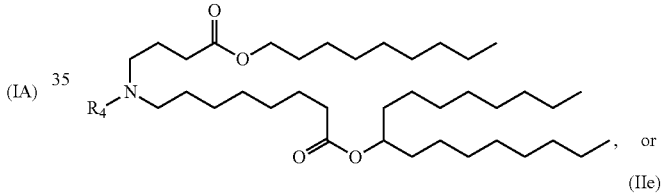

(IIc)

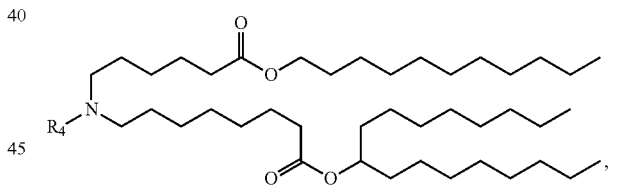

, or (IIe)

or a salt or isomer thereof, wherein R$_4$ is as described herein.

In some embodiments, a subset of compounds of Formula (I) includes those of Formula (IId):

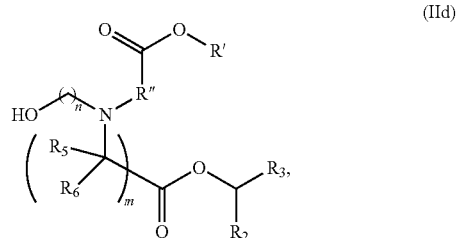

(IId)

or a salt or isomer thereof, wherein n is 2, 3, or 4; and m, R', R", and R$_2$ through R$_6$ are as described herein. For example, each of R$_2$ and R$_3$ may be independently selected from the group consisting of C$_{5-14}$ alkyl and C$_{5-14}$ alkenyl.

In some embodiments, an ionizable cationic lipid of the disclosure comprises a compound having structure:

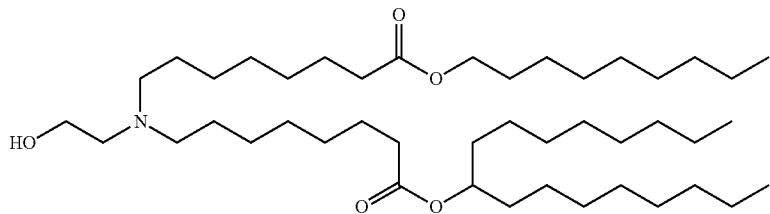

(Cmpd18)

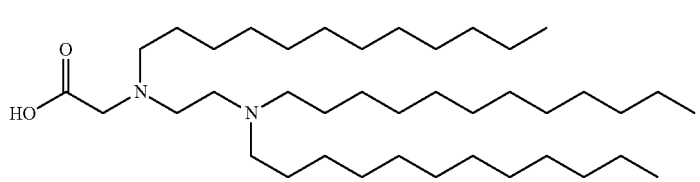

(Cmpd393)

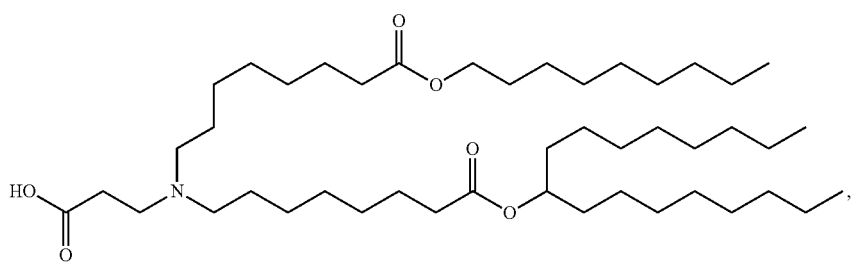

(Cmpd125)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

DSPC has the following structure:

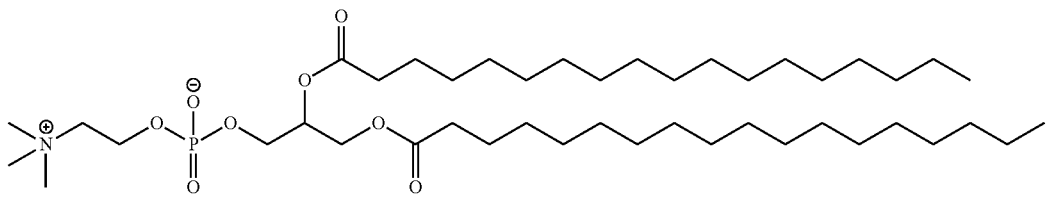 [SMILES: CCCCCCCCCCCCCCCCCC(=O)OCC(COP(=O)([O-])OCC[N+](C)(C)C)OC(=O)CCCCCCCCCCCCCCCCC]

Oleic Acid Analogs

As described herein, non-cationic lipids useful in the present invention include analogs of oleic acid. As described herein, an oleic acid analog can comprise a modified oleic acid tail, a modified carboxylic acid moiety, or both. In certain embodiments, an analog of oleic acid is a compound of Formula (IV). Provided herein are compounds of Formula (IV):

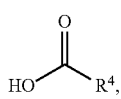

(IV)

or a salt thereof, wherein:

$R^4$ is optionally substituted, $C_{10-40}$ alkyl; optionally substituted, $C_{10-40}$ alkenyl; optionally substituted, $C_{10-40}$ alkynyl; wherein at least one methylene group of $R^4$ is independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N(R)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (IV) is one of the following:

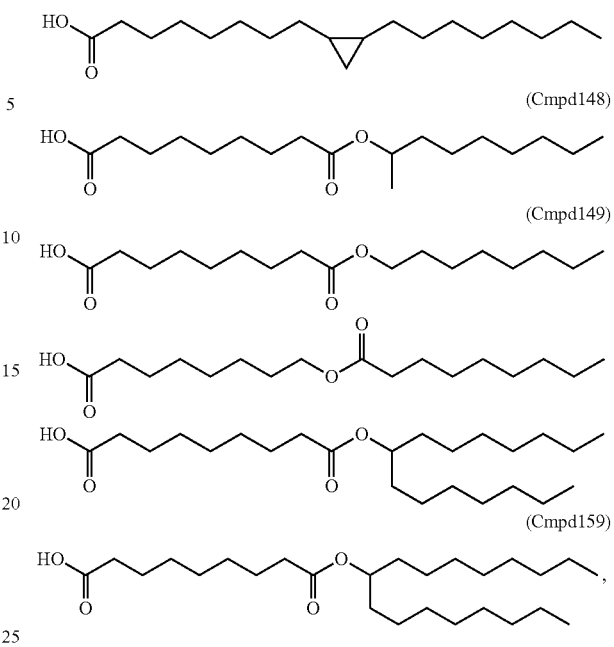

or salts thereof.

In certain embodiments, an oleic acid analog is a compound wherein the carboxylic acid moiety of oleic acid replaced by a different group. In certain embodiments, an oleic acid analog useful in the present invention is one of the following:

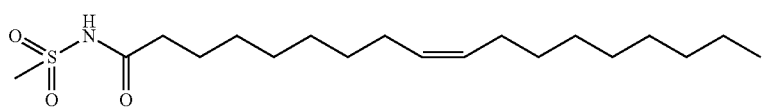

(Cmpd157)

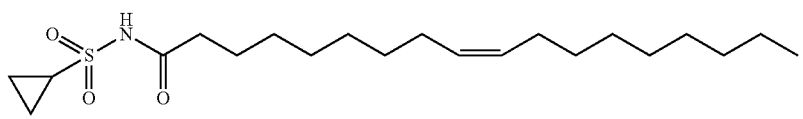

(Cmpd158)

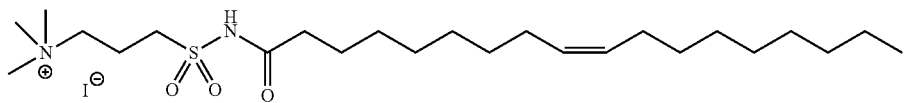

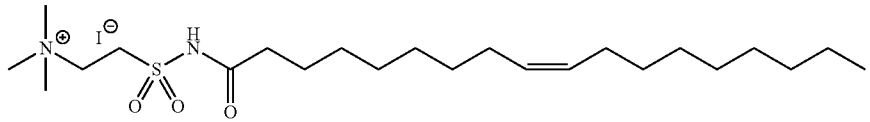

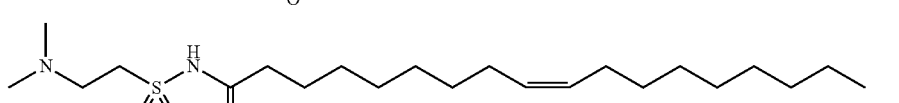

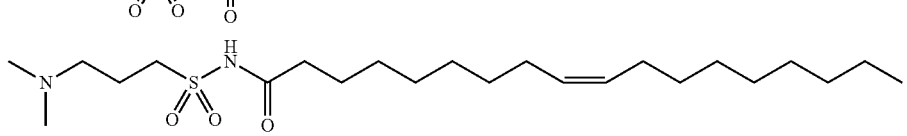

[Chemical structures shown]

or salts thereof.

In certain embodiments, an oleic acid analog useful in the present invention is:

[Chemical structure shown]

PEGylated Lipids

The lipid component of a nanoparticle composition may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

[Chemical structure shown]

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

PEG and PEG-OH Lipids

In certain embodiments, a PEG lipid useful in the present invention is a compound of Formula (III). Provided herein are compounds of Formula (III):

[Chemical structure shown]
(III)

or salts thereof, wherein:
$R^3$ is —$OR^O$;
$R^O$ is hydrogen, optionally substituted alkyl, or an oxygen protecting group;
r is an integer between 1 and 100, inclusive;
$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —N($R^N$)—, —S—, —C(O)—, —C(O)N($R^N$)—, —$NR^N$C(O)—, —C(O) O—, —OC(O)—, —OC(O)O—, —OC(O)N($R^N$)—, —$NR^N$C(O)O—, or —$NR^N$C(O)N($R^N$)—;

D is a moiety obtained by click chemistry or a moiety cleavable under physiological conditions;

m is 0, 1, 2, 3, 4, 5, 6, 7, 8, 9, or 10,

A is of the formula:

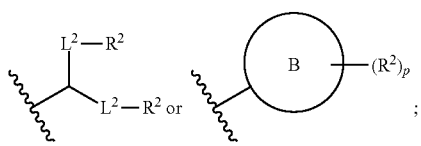

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC (O)—, —OC(O)O—, —OC(O)N($R^N$)—, —$NR^N$C(O) O—, or —$NR^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N ($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C (S)N($R^N$)—, —S(O)—, —OS(O)—, —S(O)O—, —OS(O)O—, —OS(O)$_2$—, —S(O)$_2$O—, —OS(O)$_2$ O—, —N($R^N$)S(O)—, —S(O)N($R^N$)—, —N(R)S(O)N ($R^N$)—, —OS(O)N($R^N$)—, —N($R^N$)S(O)O—, —S (O)$_2$—, —N($R^N$)S(O)$_2$-, —S(O)$_2$N($R^N$)—, —N($R^N$)S (O)$_2$N($R^N$)—, —OS(O)$_2$N($R^N$)—, or —N($R^N$)S(O)$_2$ O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (III) is a PEG-OH lipid (i.e., $R^3$ is —$OR^O$, and $R^O$ is hydrogen). In certain embodiments, the compound of Formula (II) is of Formula (III-OH):

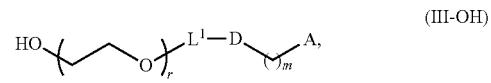

(III-OH)

or a salt thereof.

In certain embodiments, D is a moiety obtained by click chemistry (e.g., triazole). In certain embodiments, the compound of Formula (III) is of Formula (III-a-1) or (III-a-2):

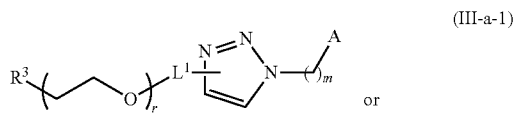

(III-a-1)

or

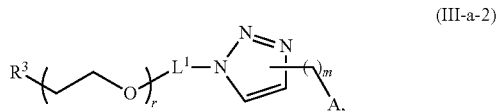

(III-a-2)

or a salt thereof.

In certain embodiments, a PEG lipid is of one of the following formulae:

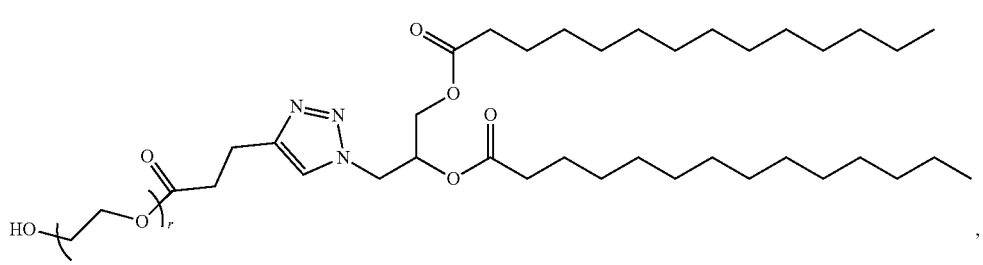

(Cmpd394)

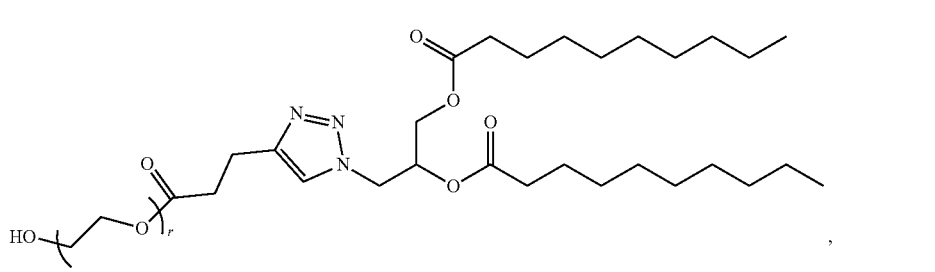

(Cmpd396)

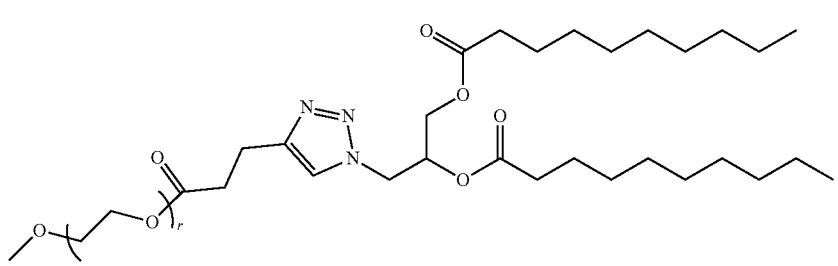
(Cmpd395)

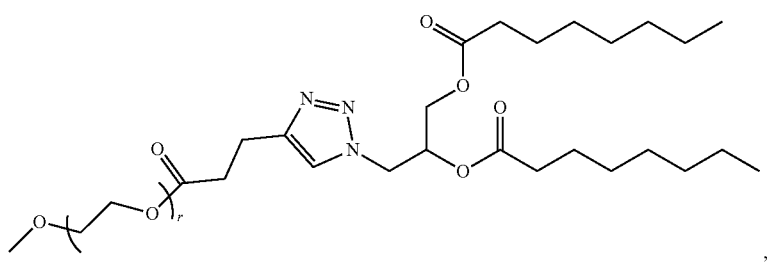
(Cmpd397)

or a salt thereof.

In certain embodiments, a compound of Formula (III) is of one of the following formulae:

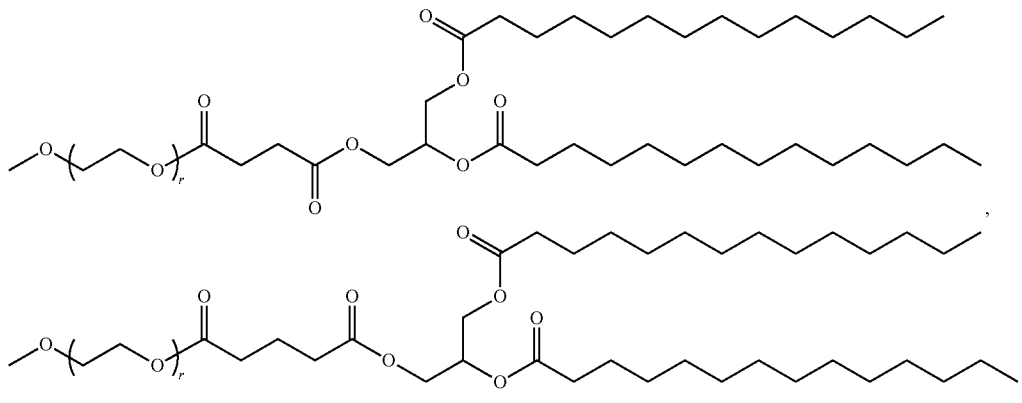

or salts thereof.

In certain embodiments, a PEG lipid useful in the present invention is a PEGylated fatty acid. In certain embodiments, a PEG lipid useful in the present invention is a compound of Formula (V). Provided herein are compounds of Formula (V):

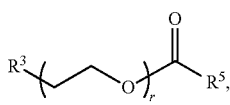

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10\text{-}40}$ alkyl, optionally substituted $C_{10\text{-}40}$ alkenyl, or optionally substituted $C_{10\text{-}40}$ alkynyl; and optionally one or more methylene groups of $R^5$ are replaced with optionally substituted carbocyclylene, optionally substituted heterocyclylene, optionally substituted arylene, optionally substituted heteroarylene, —N($R^N$)—, —O—, —S—, —C(O)—, —C(O)N(R)—, —$NR^N$C(O)—, —$NR^N$C(O)N($R^N$)—, —C(O)O—, —OC(O)—, —OC(O)O—, —OC(O)N($R^N$), —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and each instance of $R^N$ is independently hydrogen, optionally substituted alkyl, or a nitrogen protecting group.

In certain embodiments, the compound of Formula (V) is of Formula (V-OH):

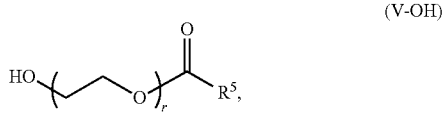

or a salt thereof.

In certain embodiments, a compound of Formula (V) is of one of the following formulae:

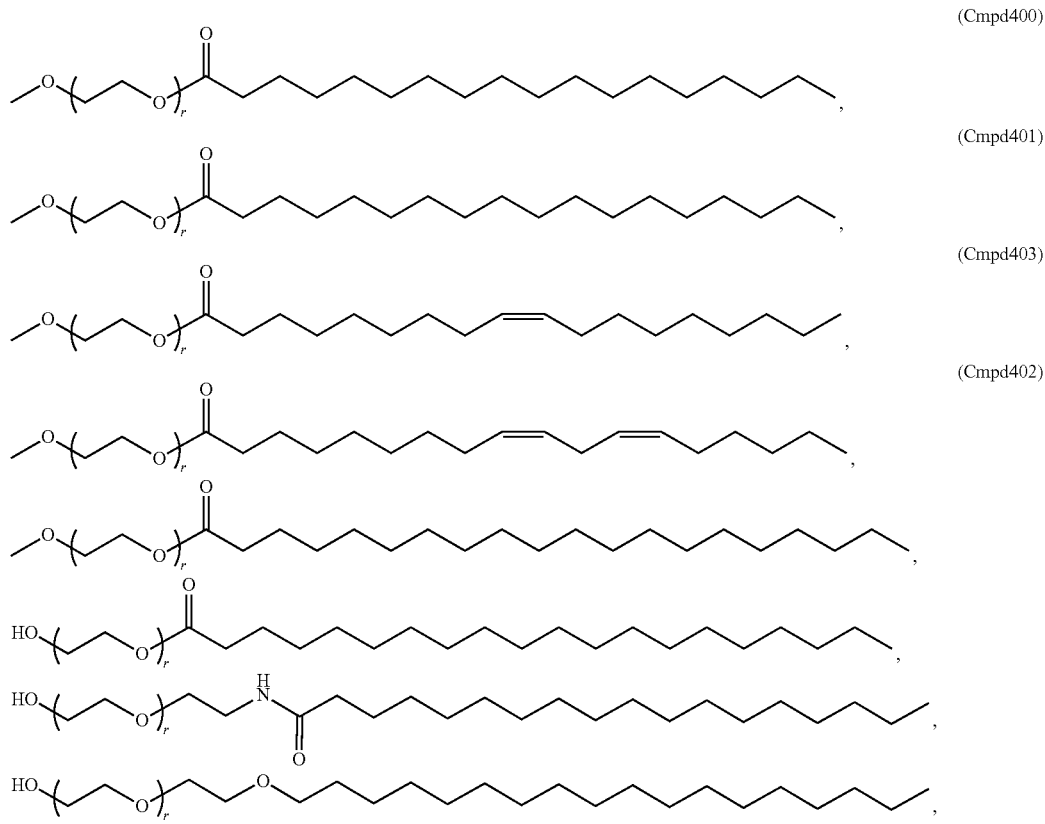

or a salt thereof. In some embodiments r is 2-100, 10-90, 20-80, 30-60, 35-55, 40-45, 45 or 100.

Numerous LNP formulations having different PEG-lipids were prepared and tested for activity, as demonstrated in the Examples included below.

Phospholipids, Including Helper Phospholipids

Phospholipids, as defined herein, are any lipids that comprise a phosphate group. Phospholipids are a subset of non-cationic lipids. The lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye). Each possibility represents a separate embodiment of the present invention.

Phospholipid Head Modifications

In certain embodiments, a phospholipid useful in the present invention comprises a modified phospholipid head (e.g., a modified choline group). In certain embodiments, a phospholipid with a modified head is DSPC, or analog thereof, with a modified quaternary amine.

Phospholipid Core Modifications

In certain embodiments, phospholipids useful in the present invention comprise a modified core. In certain embodiments, a phospholipid with a modified core described herein is DSPC, or analog thereof, with a modified core structure.

Phospholipid Tail Modifications

In certain embodiments, a phospholipid useful in the present invention comprises a modified tail. In certain embodiments, a phospholipid useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof.

The polynucleotides of the invention can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with polynucleotides, hyaluronidase, nanoparticle mimics and combinations thereof.

In some embodiments, nucleic acid molecules of the invention can be formulated using one or more liposomes, lipoplexes, or lipid nanoparticles. In one embodiment, pharmaceutical compositions of nucleic acid molecules include lipid nanoparticles (LNPs). In some embodiments, lipid nanoparticles are MC3-based lipid nanoparticles.

In one embodiment, the polynucleotides may be formulated in a lipid-polycation complex. The formation of the lipid-polycation complex may be accomplished by methods known in the art. As a non-limiting example, the polycation may include a cationic peptide or a polypeptide such as, but not limited to, polylysine, polyornithine and/or polyarginine. In another embodiment, the polynucleotides may be formulated in a lipid-polycation complex which may further include a non-cationic lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to RNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol) 2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the polynucleotide is formulated in a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US2013/0150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US2013/0150625); 2-amino-3-[(9Z)-octadec-9-en-1-yloxy]-2-{[(9Z)-octadec-9-en-1-yloxy]methyl}propan-1-ol (Compound 2 in US2013/0150625); 2-amino-3-[(9Z,12Z)-octadeca-9,12-dien-1-yloxy]-2-[(octyloxy)methyl]propan-1-ol (Compound 3 in US2013/0150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US2013/0150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, and DOPE; (iii) a sterol, e.g., cholesterol; and (iv) a PEG-lipid, e.g., PEG-DMG or PEG-cDMA, in a molar ratio of about 20-60% cationic lipid:5-25% neutral lipid:25-55% sterol; 0.5-15% PEG-lipid.

In one embodiment, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 500/% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, and DOPE. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20° % on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA.

In one embodiment, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations of the inventions include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1.3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 400/o of the sterol, and about 5% of the PEG or PEG-modified lipid on a molar basis.

In one embodiment, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations of the inventions include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ⌇⌇⌇ is a single bond where the stereochemistry of the moieties immediately attached thereto is not specified, - - - is absent or a single bond, and ═══ or ═══ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —CHF$_2$, —CH$_2$F, —CF$_3$, —CH$_2$CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl").

In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphtalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. Each possibility represents a separate embodiment of the present invention.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond. The term "unsaturated" or "partially unsaturated" refers to a moiety that includes at least one double or triple bond. The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl. C$_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —P(=O)(R$^{ee}$)$_2$, —OP(=O)(R$^{ee}$)$_2$, —OP(=O)(R$^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(C$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$), —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein $R^{aa}$, $R^{bb}$ and $R^{cc}$ are as defined herein, and wherein $R^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^−$, wherein R$^{bb}$ and X$^−$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate. 2-iodobenzoate, 4-azidobutyrate. 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, to alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3{}^-$, $ClO_4{}^-$, $OH^-$, $H_2PO_4{}^-$, $HCO_3{}^-$, $HSO_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4{}^-$, $PF_4{}^-$, $PF_6{}^-$, $AsF_6{}^-$, $SbF_6{}^-$, $B[3,5-(CF_3)_2C_6H_3]_4{}^-$, $B(C_6F_5)_4{}^-$, $BPh_4{}^-$, $Al(OC(CF_3)_3)_4{}^-$, and carborane anions (e.g., $CB_{11}H_{12}{}^-$ or $(HC_{11}Me_5Br_6)^-$). Exemplary counterions which may be multivalent include $CO_3{}^{2-}$, $HPO_4{}^{2-}$, $PO_4{}^{3-}$, $B_4O_7{}^{2-}$, $SO_4{}^{2-}$, $S_2O_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

These and other exemplary substituents are described in more detail throughout. The invention is not intended to be limited in any manner by the above exemplary listing of substituents.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4{}^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Biologically Active Agents

This disclosure contemplates that the LNPs provided herein and/or the various combination therapies provided herein may be used to deliver a nucleic acid such as an mRNA to a subject. The nucleic acids typically will encode a biologically active protein. Biologically active proteins are agents that have an effect in vivo, and preferably a beneficial effect, such as desirable immune modulation, immune stimulation, immune inhibition, cell killing, cell preservation, modified gene expression, protein replacement, and the like. Biologically active proteins include but are not limited to prophylactic agents, therapeutic agents, and diagnostic agents. Biologically active proteins include immunomodulatory agents such as immunostimulatory or immunoinhibitory agents, antigens, antibodies and antibody fragments such as antigen-binding antibody fragments, adjuvants, cytokines such as interleukins, anti-bacterial agents, anti-viral agents, anti-fungal agents, anti-parasitic agents, anti-cancer agents, anti-inflammatory agents, and the like.

They may be used to express nucleic acids and/or proteins in cells, particularly in cells that are deficient in such nucleic acids or proteins or have mutated versions of such nucleic acids or proteins. They may be used to introduce and express nucleic acids or proteins that are not native to the cell or organism, as may be done for example in the context of an immunization or vaccination protocol. In this respect, the nucleic acid or protein may be foreign to the subject to whom it is administered (e.g., not naturally occurring in such subject, or not naturally occurring at all), and it is administered to the subject to induce and/or boost an immune response to such nucleic acid or protein. The nucleic acids provided herein may be used for such a purpose.

As used herein, the term "nucleic acid" refers to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. A nucleic acid sequence is presented in the 5' to 3' direction unless otherwise indicated.

Therapeutic compositions of the present disclosure comprise, in some embodiments, at least one nucleic acid (e.g., RNA) having an open reading frame encoding at least one therapeutic protein or intracellular protein, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art. For example, a chemically modified uracil, e.g., pseudouracil, 1-methylpseuodouracil, 5-methoxyuracil, or the like. In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519: PCT/US2013/075177; PCT/US2014/058897; PCT/US2014/058891; PCT/US2014/070413; PCT/US2015/036773; PCT/US2015/036759; PCT/US2015/036771; or PCT/IB2017/051367 all of which are incorporated by reference herein.

In some embodiments, at least one RNA (e.g., mRNA) of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises 1-methyl-pseudouridine (m1ψ) substitutions at one or more or all uridine positions of the nucleic acid.

In some embodiments, a RNA nucleic acid of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80 modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

In some embodiments, polynucleotides function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The basic components of an mRNA molecule typically include at least one coding region, a 5' untranslated region (UTR), a 3' UTR, a 5' cap and a poly-A tail. Polynucleotides may function as mRNA but can be distinguished from wild-type mRNA in their functional and/or structural design features which serve to overcome existing problems of effective polypeptide expression using nucleic-acid based therapeutics.

The mRNA, as provided herein, comprises at least one (one or more) ribonucleic acid (RNA) polynucleotide having an open reading frame encoding at least one polypeptide of interest. In some embodiments, a RNA polynucleotide of an mRNA encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 polypeptides. In some embodiments, a RNA polynucleotide of an mRNA encodes at least 10, 20, 30, 40, 50, 60, 70, 80, 90 or 100 polypeptides. In some embodiments, a RNA polynucleotide of an mRNA encodes at least 100 or at least 200 polypeptides.

In some embodiments, the nucleic acids are therapeutic mRNAs. As used herein, the term "therapeutic mRNA" refers to an mRNA that encodes a therapeutic protein. Therapeutic proteins mediate a variety of effects in a host cell or a subject in order to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). Therapeutic mRNA may be useful for the treatment of the following exemplary diseases and conditions: bacterial infections, viral infections, parasitic infections, cell proliferation disorders, genetic disorders, and autoimmune disorders. In particular, the subject methods are useful for indications in which repeated administration of proteins or polynucleotides encoding those proteins via a non-IV route results in unwanted immune responses, e.g., anti-drug antibodies.

Thus, the IV administration or LNPs comprising polynucleotides encoding therapeutic proteins of the invention can be used to induce tolerance to subsequent non-IV administration of the same therapeutic or prophylactic agents. They are provided for use in medicine. For example, after one or more IV doses of an LNP comprising a polynucleotide that encodes a therapeutic protein, that same therapeutic protein or a polynucleotide encoding that protein can be administered to a subject for a longer period without inducing or inducing a lower immune response.

Provided are compositions, methods, kits, and reagents for diagnosis, treatment or prevention of a disease or condition in humans and other mammals.

An "effective amount" of the compositions are provided based, at least in part, on the target tissue, target cell type, means of administration, physical characteristics of the polynucleotide (e.g., size, and extent of modified nucleosides) and other components of the nucleic acids, and other determinants. In general, an effective amount of the nucleic acids provides an induced or boosted peptide production in the cell.

The mRNA of the present invention may be designed to encode polypeptides of interest selected from any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery.

In certain embodiments, an mRNA included in a nanoparticle composition may encode a polypeptide that may replace one or more polypeptides that may be substantially absent in a cell contacted with the nanoparticle composition. The one or more substantially absent polypeptides may be lacking due to a genetic mutation of the encoding gene or a regulatory pathway thereof. Alternatively, a polypeptide produced by translation of the mRNA may antagonize the activity of an endogenous protein present in, on the surface of, or secreted from the cell. An antagonistic polypeptide may be desirable to combat deleterious effects caused by activities of the endogenous protein, such as altered activities or localization caused by mutation. In another alternative, a polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Polypeptides produced by translation of the mRNA may be engineered for localization within the cell, such as within a specific compartment such as the nucleus, or may be engineered for secretion from the cell or for translocation to the plasma membrane of the cell.

The nanoparticle compositions may be useful for treating a disease, disorder, or condition characterized by missing or aberrant protein or polypeptide activity. Upon delivery of an mRNA encoding the missing or aberrant polypeptide to a cell, translation of the mRNA may produce the polypeptide, thereby reducing or eliminating an issue caused by the absence of or aberrant activity caused by the polypeptide. Because translation may occur rapidly, the methods and compositions of the invention may be useful in the treatment of acute diseases, disorders, or conditions such as sepsis, stroke, and myocardial infarction. An mRNA included in a nanoparticle composition of the invention may also be capable of altering the rate of transcription of a given species, thereby affecting gene expression.

Diseases, disorders, and/or conditions characterized by dysfunctional or aberrant protein or polypeptide activity for which a composition of the invention may be administered include, but are not limited to, cancer and proliferative diseases, genetic diseases (e.g., cystic fibrosis), autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis. The present disclosure provides a method for treating such diseases, disorders, and/or conditions in a subject by administering a nanoparticle composition including an mRNA and a lipid component, wherein the mRNA encodes a polypeptide that antagonizes or otherwise overcomes an aberrant protein activity present in the cell of the subject.

The mRNA disclosed herein, may encode one or more biologics. As used herein, a "biologic" is a polypeptide-based molecule produced by the methods provided herein and which may be used to treat, cure, mitigate, prevent, or diagnose a serious or life-threatening disease or medical condition. Biologics, according to the present invention include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

According to the present invention, one or more biologics currently being marketed or in development may be encoded by the mRNA of the present invention. While not wishing to be bound by theory, it is believed that incorporation of the encoding polynucleotides of a known biologic into the mRNA of the invention will result in improved therapeutic efficacy due at least in part to the specificity, purity and/or selectivity of the construct designs.

The initial administration of an intracellular protein in an LNP may be used to avoid an immune response against subsequent doses of other types of therapeutics. For instance the initial administration of the intracellular protein may be used to avoid ABC or ADA responses to subsequent administration of a therapeutic protein or a polynucleotide encoding a therapeutic protein.

The mRNA disclosed herein, may encode or the therapeutic protein may itself be one or more antibodies or fragments thereof. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. The term "immunoglobulin" (Ig) is used interchangeably with "antibody" herein. As used herein, the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include, but are not limited to, "primatized" antibodies comprising variable domain antigen-binding sequences derived from a non-human primate (e.g., Old World Monkey, Ape etc.) and human constant region sequences.

An "antibody fragment" comprises a portion of an intact antibody, preferably the antigen binding and/or the variable region of the intact antibody. Examples of antibody fragments include Fab, Fab', F(ab')2 and Fv fragments; diabodies; linear antibodies; nanobodies; single-chain antibody molecules and multispecific antibodies formed from antibody fragments.

Any of the five classes of immunoglobulins, IgA, IgD, IgE, IgG and IgM, may be encoded by the mRNA of the invention, including the heavy chains designated alpha, delta, epsilon, gamma and mu, respectively. Also included are polynucleotide sequences encoding the subclasses, gamma and mu. Hence any of the subclasses of antibodies may be encoded in part or in whole and include the following subclasses: IgG1, IgG2, IgG3, IgG4, IgA1 and IgA2. According to the present invention, one or more antibodies or fragments currently being marketed or in development may be encoded by the mRNA of the present invention.

Antibodies encoded in the mRNA of the invention may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective.

In one embodiment, mRNA disclosed herein may encode monoclonal antibodies and/or variants thereof. Variants of antibodies may also include, but are not limited to, substitutional variants, conservative amino acid substitution, insertional variants, deletional variants and/or covalent derivatives. In one embodiment, the mRNA disclosed herein may encode an immunoglobulin Fc region. In another embodiment, the mRNA may encode a variant immunoglobulin Fc region.

The antibody or antibody fragment may be, for instance, bevacizumab (AVASTIN), trastuzumab (HERCEPTIN), alemtuzumab (CAMPATH, indicated for B cell chronic lymphocytic leukemia,), gemtuzumab (MYLOTARG, hP67.6, anti-CD33, indicated for leukemia such as acute myeloid leukemia), rituximab (RITUXAN), tositumomab (BEXXAR, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX, indicated for ovarian cancer), edrecolomab (PANOREX), daclizumab (ZENAPAX), palivizumab (SYNAGIS, indicated for respiratory conditions such as RSV infection), ibritumomab tiuxetan (ZEVALIN, indicated for Non-Hodgkin's lymphoma), cetuximab (ERBITUX), MDX-447, MDX-22, MDX-220 (anti-TAG-72), IOR-C5, IOR-T6 (anti-CD1), IOR EGF/R3, celogovab (ONCOSCINT OV103), epratuzumab (LYMPHOCIDE), pemtumomab (THERAGYN), or Gliomab-H (indicated for brain cancer, melanoma).

The mRNA disclosed herein, may encode one or more vaccine antigens. Vaccine antigens encoded in the mRNA of the invention may be utilized to treat conditions or diseases in many therapeutic areas such as, but not limited to allergy and autoimmune disease.

The mRNA of the present invention may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals. The anti-microbial polypeptides described herein may block cell fusion and/or viral entry by one or more enveloped viruses (e.g., HIV, HCV). For example, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the transmembrane subunit of a viral envelope protein, e.g., HIV-1 gp120 or gp41. The amino acid and nucleotide sequences of HIV-1 gp120 or gp41 are described in, e.g., Kuiken et al., (2008). "HIV Sequence Compendium," Los Alamos National Laboratory.

In some embodiments, the anti-microbial polypeptide may have at least about 75%, 80%, 85%, 90%, 95%, 100% sequence homology to the corresponding viral protein sequence. In some embodiments, the anti-microbial polypeptide may have at least about 75%, 80%, 85%, 90%, 95%, or 100% sequence homology to the corresponding viral protein sequence.

In other embodiments, the anti-microbial polypeptide may comprise or consist of a synthetic peptide corresponding to a region, e.g., a consecutive sequence of at least about 5, 10, 15, 20, 25, 30, 35, 40, 45, 50, 55, or 60 amino acids of the binding domain of a capsid binding protein. In some embodiments, the anti-microbial polypeptide may have at least about 75%, 80%, 85%, 90%, 95%, or 100% sequence homology to the corresponding sequence of the capsid binding protein.

The anti-microbial polypeptides described herein may block protease dimerization and inhibit cleavage of viral proproteins (e.g., HIV Gag-pol processing) into functional proteins thereby preventing release of one or more enveloped viruses (e.g., HIV, HCV). In some embodiments, the anti-microbial polypeptide may have at least about 75%, 80%, 85%, 90%, 95%, 100% sequence homology to the corresponding viral protein sequence.

In other embodiments, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the binding domain of a protease binding protein. In some embodiments, the anti-microbial polypeptide may have at least about 75%, 80%, 85%, 90%, 95%, 100% sequence homology to the corresponding sequence of the protease binding protein.

A non-limiting list of infectious diseases that the mRNA anti-microbial peptides may treat is presented below: human immunodeficiency virus (HIV), HIV resulting in mycobacterial infection, AIDS related Cacheixa, AIDS related Cytomegalovirus infection, HIV-associated nephropathy, Lipodystrophy, AID related cryptococcal meningitis, AIDS related neutropaenia, *Pneumocysitis jiroveci* (*Pneumocystis carinii*) infections, AID related toxoplasmosis, hepatitis A, B, C, D or E, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, staphylococcal infections, *salmonella* infections or streptococcal infections, tetanus (*Clostridium tetani*), protozoan infectious diseases (malaria, sleeping sickness, leishmaniasis, toxoplasmosis, i.e. infections caused by *plasmodium*, trypanosomes, *leishmania* and *toxoplasma*), diphtheria, leprosy, measles, pertussis, rabies, tetanus, tuberculosis, typhoid, varicella, diarrheal infections such as Amoebiasis, *Clostridium difficile*-associated diarrhea (CDAD), Cryptosporidiosis, Giardiasis, Cyclosporiasis and Rotaviral gastroenteritis, encephalitis such as Japanese encephalitis, Wester equine encephalitis and Tick-borne encephalitis (TBE), fungal skin diseases such as candidiasis, onychomycosis, Tinea captis/scal ringworm, Tinea corporis/body ringworm, Tinea cruris/jock itch, sporotrichosis and Tinea pedis/ Athlete's foot, Meningitis such as *Haemophilus* influenza type b (Hib), Meningitis, viral, meningococcal infections and pneumococcal infection, neglected tropical diseases such as Argentine haemorrhagic fever, Leishmaniasis, Nematode/roundworm infections, Ross river virus infection and West Nile virus (WNV) disease, Non-HIV STDs such as Trichomoniasis, Human papillomavirus (HPV) infections, sexually transmitted chlamydial diseases, Chancroid and Syphilis, Non-septic bacterial infections such as cellulitis, lyme disease, MRSA infection, *pseudomonas*, staphylococcal infections, Boutonneuse fever, Leptospirosis, Rheumatic fever, Botulism, Rickettsial disease and Mastoiditis, parasitic infections such as Cysticercosis, Echinococcosis, Trematode/Fluke infections, Trichinellosis, Babesiosis, Hypodermyiasis, Diphyllobothriasis and Trypanosomiasis, respiratory infections such as adenovirus infection, aspergillosis infections, avian (H5N1) influenza, influenza, RSV infections, severe acute respiratory syndrome (SARS), sinusitis, Legionellosis, Coccidioidomycosis and swine (H1N1) influenza, sepsis such as bacteraemia, sepsis/septic shock, sepsis in premature infants, urinary tract infection such as vaginal infections (bacterial), vaginal infections (fungal) and gonococcal infection, viral skin diseases such as B19 parvovirus infections, warts, genital herpes, orofacial herpes, shingles, inner ear infections, fetal cytomegalovirus syndrome, foodborn illnesses such as brucellosis (*Brucella* species), *Clostridium perfringens* (Epsilon toxin), *E. Coli* O157:H7 (*Escherichia coli*), Salmonellosis (*Salmonella* species), Shingellosis (Shingella), Vibriosis and Listeriosis, bioterrorism and potential epidemic diseases such as Ebola haemorrhagic fever, Lassa fever, Marburg haemorrhagic fever, plague, Anthrax Nipah virus disease, Hanta virus, Smallpox, Glanders (*Burkholderia mallei*), Melioidosis (*Burkholderia pseudomallei*). Psittacosis (*Chlamydia psittaci*), Q fever (*Coxiella burnetii*), Tularemia (*Fancisella tularensis*), rubella, mumps and polio.

The mRNA disclosed herein, may encode one or more validated or "in testing" therapeutic proteins or peptides. According to the present invention, one or more therapeutic proteins or peptides currently being marketed or in development may be encoded by the mRNA of the present invention. Therapeutic proteins and peptides encoded in the mRNA of the invention may be utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective.

The mRNA disclosed herein, may encode one or more cell-penetrating polypeptides. As used herein, "cell-penetrating polypeptide" or CPP refers to a polypeptide which may facilitate the cellular uptake of molecules. A cell-penetrating polypeptide of the present invention may contain one or more detectable labels. The polypeptides may be partially labeled or completely labeled throughout. The mRNA may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

In one embodiment, the mRNA may also encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

The cell-penetrating polypeptide encoded by the mRNA may form a complex after being translated. The complex may comprise a charged protein linked, e.g. covalently linked, to the cell-penetrating polypeptide.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but is not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the mRNA may be introduced. The cell-penetrating polypeptide may also be capable of penetrating the first cell.

In one embodiment, the mRNA may encode a cell-penetrating polypeptide which may comprise a protein-binding partner. The protein binding partner may include, but is not limited to, an antibody, a supercharged antibody or a functional fragment. The mRNA may be introduced into the cell where a cell-penetrating polypeptide comprising the protein-binding partner is introduced.

Some embodiments of the present disclosure provide a therapeutic mRNA that includes at least one ribonucleic acid (RNA) polynucleotide having an open reading frame encoding at least one polypeptide, in which the RNA polynucleotide of the RNA includes at least one chemical modification. In some embodiments, the chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine,), 5-methoxyuridine, and 2'-O-methyl uridine. Each possibility represents a separate embodiment of the present invention.

Any of the foregoing polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., a protein or polypeptide)). In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., protein or polypeptide)). In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., protein or polypeptide)). In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., protein or polypeptide)). In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., protein or polypeptide)).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., protein or polypeptide)). In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., protein or polypeptide)).

In some embodiments a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

As used herein, when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% or 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453.). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and nonidentical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

An immunoinhibitory agent is an agent that inhibits an immune response in a subject to whom it is administered, whether alone or in combination with another agent. Examples include steroids, retinoic acid, dexamethasone, cyclophosphamide, anti-CD3 antibody or antibody fragment, and other immunosuppressants. Such agents may be used in combination with the methods of the invention.

When it is desirable to induce tolerance against an antigen, such a self-antigen or an allergen, such antigens may be delivered according to the methods described herein. The antigen may be peptide, lipid, or carbohydrate in nature, but it is not so limited.

In the circumstance when it is desirable to administer more than one dose of vaccine antigen to a subject encoded within a polynucleotide and formulated in an LNP within a short period of time (i.e., less than 2 to 3 weeks between doses), the methods of the invention may be used to avoid any unwanted or detrimental immune responses and/or ADA. For instance, a LNP-polynucleotide encoding an antigen may be administered a first intravenous dose and subsequently administered as a second SC dose within a 2 to 3 week time period.

A diagnostic agent, which may be referred to herein as an imaging agent, is an agent that emits a signal directly or indirectly thereby allowing its detection in vivo. Diagnostic agents include, but are not limited to, contrast agents and radioactive agents that can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide 99 mTc; imaging agents for positron-emission tomography (PET) include positron-emitting isotopes, (18)F-fluorodeoxyglucose ((18) FDG), (18)F-fluoride, copper-64, gadoamide, and radioisotopes of Pb(II) such as 203 Pb, and 11In; imaging agents for in vivo fluorescence imaging such as fluorescent dyes or dye-conjugated nanoparticles. In other embodiments, the agent to be delivered is conjugated, or fused to, or mixed or combined with a diagnostic agent.

The compounds and compositions may be administered to virtually any subject type that is likely to benefit from delivery of agents as contemplated herein. Human subjects are preferred subjects in some embodiments of the invention. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., mice, rats, rabbits, etc.), and the like. Subjects also include fish and other aquatic species.

The subjects to whom the agents are delivered may be normal subjects. Alternatively they may have or may be at risk of developing a condition that can be diagnosed or that can benefit from localized delivery of one or more particular agents. Such conditions include cancer (e.g., solid tumor cancers), infections (particularly infections localized to particular regions or tissues in the body), autoimmune disorders, allergies or allergic conditions, asthma, transplant rejection, and the like. In some embodiments, the subjects have been diagnosed with a genetic defect and are being administered a nucleic acid based therapeutic.

Agents may be administered systemically or locally. Agents may be administered in effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

The invention provides pharmaceutical compositions. Pharmaceutical compositions are sterile compositions that comprise agents and may comprise delivery vehicles, nanoparticles and the like, preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention. The term "carrier" denotes an organic or inorganic ingredient, natural or synthetic, with which the cells, nanoparticles and agent(s) are combined to facilitate administration. The components of the pharmaceutical compositions are commingled in a manner that precludes interaction that would substantially impair their desired pharmaceutical efficiency.

The compositions of the invention are delivered by intravenous administration to induce tolerance, and subsequently by non-IV route(s), e.g., subcutaneous, intramuscular, and/ or intradermal administration. In another embodiment, e.g., where the LNP used effectively reduces immune responses, a therapeutic regimen involves subcutaneous administration. The compounds and compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions such as are known in the art or that will be readily apparent to those of ordinary skill in the art based on this disclosure.

This disclosure further contemplates use of LNPs together with one or more secondary agents, including agents that would normally be indicated for the subject.

In some instances, the LNPs may be administered substantially simultaneously with the secondary agents. By substantially simultaneously, it is meant that a LNP is administered to a subject close in time with the administration of the secondary agent, including for example with 1 hour, within 30 minutes, within 10 minutes, or within 5 minutes.

In some instances, the secondary agent(s) may be administered prior to the LNP. For example, the secondary agent(s) may be administered prior to and within 24 hours, or within 18 hours, or within 12 hours, or within 6 hours, or within 3 hours, or within 2 hours of the LNP administration. The secondary agent(s) may be administered 18-24 hours prior to LNP administration, or 12-18 hours prior to LNP administration, or 6-12 hours prior to LNP administration, or 2-6 hours prior to LNP administration.

Subjects who have been administered one or more secondary agents 2 or more hours prior to LNP administration may be referred to as having been pre-medicated with such agent(s). Subjects who have been administered one or more secondary agents within 1 hour prior to LNP administration may be referred to as having been co-mediated with such agent(s).

In some instances, the secondary agent(s) may be administered continuously to the subject, on an as needed basis or on a regular schedule (e.g., every day, every two days, etc.).

In other instances, the secondary agent may be administered before or after the administration of the LNP.

Such secondary agents may include but are not limited to anti-histamines, anti-platelet agents, and non-steroidal anti-inflammatory drugs. In certain embodiments, the LNPs are not formulated with and subjects are not pre- or co-medicated with a corticosteroid, such as but not limited to dexamethasone.

In certain embodiments, single secondary agents having anti-inflammatory and anti-platelet effects are used. An example of such an agent is aspirin.

In certain embodiments, a combination of aspirin, clopidrogrel (Plavix®), and an anti-histamine such as but not limited to diphenhydramine (Benadryl), fexofenadine (Allegra), loratadine (Claritin), or cetirizine is used. One or more of the secondary agents may be administered once per LNP administration while others may be administered more frequently. For example, clopidrogrel (Plavix®) may be administered once per LNP administration while aspirin and/or the anti-histamine may be administered daily.

Anti-histamines include H1 receptor antagonists and H1 receptor inverse agonists.

Examples of H1 receptor antagonists include but are not limited to acrivastine, alimemazine, alimemazine tartrate, antazoline, astemizole, azatadine, azatadine maleate, azelastine, bamipine, benzquinamide, bepotastine, bepotastine besilate, bilastine bromazine, bromopheniramine, buclizine, carbinoxamine, chlorphenoxamine, chlorcyclizine, cinnopentazone histapyrrodine, chlorodipheynhydramine, chloropyramine, chlorphenamine, Chlorpromazine, cinnarizine, clemastine, clemizole, clocinizine, cyclizine, cyproheptadine, desloratadine, deptropine, dexchlorpheniramine, dexbrompheniraine, dimenhydrinate, dimetindene, dimetotiazine, diphenhydramine (Benadryl), piphenylpyraline, doxepin, doxylamine, ebastine, efletirizine, embramine, emedastine, epinastine, fexofenadine (Allegra), flunarizine, homochlorcyclizine, hydroxyzine, isothipendyl, ketotifen, levocabastine (2nd generation), loratadine (Claritin), mebhydroline, meclozine, mepyramine, mequitazine, methdilazine, mirtazapine, mizolastine, niaprazine, olopatadine, orphenadrine, oxatomide, oxomemazine, pemirolast, phenindamine, pheniramine, phenyltoloxamine, pimethixene, piprinhydrinate, promethazine, propiomazine, pyrrobutamine, quetiapine, quifenadine, rupatadine, setastine, terfenadine, thenyldiamine, thiethylperazine, thonzylamine, tolpropamine, trimethobenzamine, tripelennamine, triprolidine and tritoqualine.

Examples of H1 receptor inverse agonists include but are not limited to pyrilamine, cetirizine, levocetirizine, and desloratadine.

Anti-platelet agents include but are not limited to activation inhibitors, aggregation inhibitors, adhesion antagonists, anti-coagulation drugs (that do not target platelets directly), and agents that reduce platelet count or numbers.

Examples of activation inhibitors include but are not limited to (1) thrombin receptor PAR-1 inhibitors such as SCH 530348 (vorapaxar), E-5555 (atopaxar), SCH79797, FR 171113, RWJ 56110, BMS-200661, RWJ-58259, SCH205831, Pipal-7 pepducin, P1pal-12 pepducin; (2) thrombin receptor PAR-4 inhibitors such as ML 354, tcY-NH2, P4pal-10 pepducin, P4pal-i1 pepducin; (3) FSLLRY-NH2 (PAR-2 peptide antagonist); (4) TxA2 receptor antagonists such as AH 23,848, SQ 29.548, or R 68,070, S-1452, iosartan, seratrodast; (5) thromboxane receptor antagonists such as terutroban; (6) ADP P2Y12 receptor inhibitors such as ticlopidine, clopidogrel, prasugrel, ticagrelor, cangrelor, elinogrel, AZD6140, AR-C69931, CoA; (7) ADP P2Y1 receptor inhibitors such as A2P5P, A3P5P, MRS2179, MRS2279, MRS2500, palmitoyl-CoA (also acts on P2Y12), and other compounds from SAR study by Thalji et al. 2010; (8) 5-HT2A antagonists such as R-1012444, naftidrofuryl, sarpogrelate, AT-1015; (9) thromboxane syntahase inhibitors such as dazoxiben, CS-518 (TXA2 synthase inhibitor), SB 203580, U63557A, imidazo (1,5-2) pyridine-5-hexanoic acid; (10) COX-1 inhibitors such as aspirin, NCX-4016, ridogrel, S18886, picotamide, ramatroban (also TXA2 receptor antagonist), SC-560, FR122047, mofezolac, P6, TFAP, ibuprofen and naproxen (also Cox-2 inhibitors); (11) COX-2 inhibitors such as triflusal (also COX-1 and PDE inhibitor), Etoricoxib, rofecoxib, celecoxib, meloxicam; and (12) PI3K inhibitors such as AZD6482.

Examples of aggregation inhibitors include but are not limited to (1) GPIa/IIa Inhibitors such as EMS16; (2) GPVI inhibitors such as monoclonal antibodies and Fab fragments of mAb 12A5; (3) GPIIb/IIIa inhibitors such as abciximab, eptifibatide, tirofiban; (4) PDE inhibitors such as dipyridamole (also adenosine reuptake inhibitor), cilostazol (PDE3 inhibitor that results in increased cAMP, and activated PKA), and (5) ADP receptor antagonists. Other platelet aggregation inhibitors include aspirin, clopidrogrel (Plavix®), aspirin/pravastatin, cilostazol, prasugrel, aspirin/dipyridamole, ticagrelor, cangrelor, elinogrel, dipyridamole, and ticlopidine.

Examples of adhesion antagonists (to fibrinogen) include but are not limited to C1qTNF-related protein-1, DZ-697b, RG12986.

Examples of non-platelet anti-coagulation agents include but are not limited to warfarin; Xa inhibitors such as rivaroxaban, apixaban, edoxaban, betrixaban, darexaban, otamixaban; thrombin inhibitors such as bivalirudin, hirudin, dabigatran, lepirudin, desirudin, argatroban, melagatran, dabigatran, CDSO3, FDSO3, SDSO3, and additional sulphated benzofurans allorsteric inhibitors reported by Sidhu et al. paper.

Examples of agents that reduce platelet count or number include but are not limited to (1) cAMP phosphodiesterase inhibitors (e.g., anagrelide), 6,7-dichloro-1,5-dihydroimidazo-[2,1-b]quinazolin-2(3H)-one or 6,7-dichloro-1,2,3,5-tetrahydroimidazo[2, I-b]quinazolin-2-one (U.S. Pat. Nos. 3,932,407; 4,146,718; RE31,617, Haematologica 1992 77:40-3), (2) antibodies to cell surface receptors specifically expressed by platelets or megakaryocytes such as glycoprotein IIb/IIIa receptor antibodies, (3) most chemotherapeutic anti-cancer drugs such as busulphan (Br. J. Haematol. 1986 62:229-37), hydroxyurea (N Engl J Med 1995 332:1132-6), hepsulfan, phosphorus-32 (Br J Radiol 1997 70:1169-73), pipobroman (Scand J. Haematol 1986 37:306-9), cyclophosphamide (J Cell Physiol 1982 112:222-8), certain alkylating agents and certain antimetabolites, (4) cytokines, growth factors and interleukins such as alpha-interferon (Cancer Immunol Immunother 1987 25:266-73), gamma-interferon, transforming growth factor-beta, neutrophil activating peptide-2 and its analogs (U.S. Pat. No. 5,472,944), macrophage inflammatory protein and its analogs (U.S. Pat. No. 5,306, 709), (5) compounds secreted by either platelets or megakaryocytes such as platelet-factor 4 (U.S. Pat. No. 5,185, 323), transforming growth factor-beta, the 12-17 kD glycoprotein produced by megakaryocytes, thrombin and thrombospondin and its amino (1-174 amino acid) terminal fragment (J Lab Clin Med 1997 129:231-8), and (6) other agents including anti-cheloid agents such as Tranilast (Rizaben) (J Dermatol 1998 25:706-9); forskolin and spleen anti-maturation factor (U.S. Pat. No. 4,088,753).

Anti-platelet agents may also be characterized as anti-thrombotic agents, fibrinolytic agents, direct thrombin inhibitors, glycoprotein IIb/IIIa receptor inhibitors, agents that bind to cellular adhesion molecules and inhibit the ability of white blood cells to attach to such molecules, calcium channel blockers, beta-adrenergic receptor blockers, cyclooxygenase-2 inhibitors, and angiotensin system inhibitors.

Anti-thrombotic agents are defined as agents which prevent the formation of a blood thrombus via a number of potential mechanisms and they include fibrinolytic agents, anti-coagulant agents, and inhibitors of platelet function.

Fibrinolytic agents are defined as agents that lyse a thrombus (e.g., a blood clot), usually through the dissolution of fibrin by enzymatic action. Examples of thrombolytic agents include but are not limited to ancrod, anistreplase, bisobrin lactate, brinolase, Hageman factor (i.e. factor XII) fragments, molsidomine, plasminogen activators such as streptokinase, tissue plasminogen activators (TPA) and urokinase, and plasmin and plasminogen. Anti-coagulant agents also include inhibitors of factor Xa, factor TFPI, factor VIIa, factor IXc, factor Va, factor VIIIa as well as inhibitors of other coagulation factors.

Anti-coagulant agents are agents which inhibit the coagulation pathway by impacting negatively upon the production, deposition, cleavage and/or activation of factors essential in the formation of a blood clot. Anti-coagulant agents include but are not limited to vitamin K antagonists such as coumarin and coumarin derivatives (e.g., warfarin sodium); glycosoaminoglycans such as heparins both in unfractionated form and in low molecular weight form; ardeparin sodium, bivalirudin, bromindione, coumarin dalteparin sodium, desirudin, dicumarol, lyapolate sodium, nafamostat mesylate, phenprocoumon, sulfatide, and tinzaparin sodium.

Other "anti-coagulant" and/or "fibrinolytic" agents include Plasminogen; Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Streptase; Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Still other anti-coagulant agents include, but are not limited to, Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bromindione; Desirudin; Dicumarol; Heparin Calcium; Heparin Sodium; Lyapolate Sodium; Nafamostat Mesylate; Phenprocoumon.

Clot lysing agents include, but are not limited to, tissue plasminogen activator, streptokinase, and nimodipine.

Inhibitors of platelet function are agents that impair the ability of mature platelets to perform their normal physiological roles (i.e., their normal function). Platelets are normally involved in a number of physiological processes such as adhesion, for example, to cellular and non-cellular entities, aggregation, for example, for the purpose of forming a blood clot, and release of factors such as growth factors (e.g., platelet-derived growth factor (PDGF)) and platelet granular components. One subcategory of platelet function inhibitors are inhibitors of platelet aggregation which are compounds which reduce or halt the ability of platelets to associate physically with themselves or with other cellular and non-cellular components, thereby precluding the ability of a platelet to form a thrombus.

Examples of useful inhibitors of platelet function include but are not limited to acadesine, anagrelide, anipamil, argatroban, aspirin, clopidogrel, cyclooxygenase inhibitors such as nonsteroidal anti-inflammatory drugs and the synthetic compound FR-122047, danaparoid sodium, dazoxiben hydrochloride, diadenosine 5',5'''-P1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin (PGI2), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and anti-serotonin drugs, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine.

"Direct thrombin inhibitors" include hirudin, hirugen, hirulog, agatroban, PPACK, thrombin aptamers.

"Glycoprotein IIb/IIIa receptor inhibitors" are both antibodies and non-antibodies, and include but are not limited to ReoPro (abcixamab), lamifiban, tirofiban.

"Calcium channel blockers" are a chemically diverse class of compounds having important therapeutic value in the control of a variety of diseases (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that prevent or slow the entry of calcium into cells by regulating cellular calcium channels. (Remington, The Science and Practice of Pharmacy, Nineteenth Edition, Mack Publishing Company, Eaton, PA, p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy) phthalide. The above-identified compounds can be used as isomeric mixtures, or in their respective levorotating or dextrorotating form.

Cyclooxygenase-2 (COX-2) is a recently identified form of a cyclooxygenase. "Cyclooxygenase" is an enzyme complex present in most tissues that produces various prostaglandins and thromboxanes from arachidonic acid. Non-steroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, CA, entitled: "Human cyclooxygenase-2 cDNA and assays for evaluating cyclooxygenase-2 activity").

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, CA). Additional COX-2 inhibitors are also described in U.S. Pat. No. 5,643,933, assigned to G. D. Searle & Co. (Skokie, IL), entitled: "Substituted sulfonylphenylheterocycles as cyclooxygenase-2 and 5-lipoxygenase inhibitors." Aspirin is an example of a COX-2 inhibitor.

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO1995/000501, published Jan. 5, 1995, WO1995/018799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

Non-steroidal anti-inflammatory drugs include but are not limited to naproxen sodium, diclofenac, sulindac, oxaprozin, diflunisal, aspirin, piroxicam, indomethocin, etodolac, ibuprofen, fenoprofen, ketoprofen, mefenamic acid, nabumetone, tolmetin sodium, and ketorolac tromethamine.

In some embodiments, the secondary agent may be an agent that inhibits the production of natural IgM, IgG, and/or activation of B1a and/or B1b cells by LNPs. Such agents may be antagonists of a surface receptor of B1a cells (e.g., CD36 and C5a) or B1b cells, for examples, antibodies or small molecule inhibitors that bind the surface receptor and interfere with its binding to its cognate ligands (e.g., lipid component such as phosphatidylcholine in certain LNPs).

In other embodiments, the secondary agent may be an agent that inhibits the activation of platelets and/or complement system (classical pathway or alternative pathway) by LNPs. Such agents may be CD36 antagonists, TLR antagonists, or antagonists of any component in the complement cascade. Such antagonists may be antagonistic antibodies specific to one of the targets. In some examples, the antagonists may be a protease inhibitor that targets one or more of the serine protease component in the complement system. Other CD36 antagonists include, but are not limited to, salvianolic acid or metabolites thereof (e.g., RA and DSS), 3-cinnamoyl indole, 13-pentyl berberine, hexarelin, or certain fatty acids such as DHA.

It is to be understood that the disclosure contemplates use of one or more of the foregoing secondary agents with any of the LNP provided herein, including for example those that comprise a cationic lipid such as MC3, a helper lipid such as DSPC or DOPE, a structural lipid such as cholesterol, and a methoxy-PEGylated lipid such as DMG-PEG, including when such methoxy-PEGylated lipid is used at a molar percentage of greater than 0.5% including 1.5%. Thus, the disclosure contemplates that LNPs that would otherwise trigger a platelet response may be used together with secondary agents that include one or more anti-platelet secondary agents. Such combinations are intended to reduce frequency and/or severity of ABC and toxicity related to LNP use in vivo.

Also provided herein are methods for reducing drug responses, including ABC and dose-limiting toxicity, associated with LNPs encapsulating mRNAs.

ABC is a threshold phenomenon, which means that the dose of an agent such as LNPs must reach a threshold to induce clinically significant ABC (substantial). Accordingly, it is contemplated that using a dose lower than the threshold could reduce ABC or prevent its occurrence. Alternatively, the LNPs described herein can lower B1a and/or B1b and/or natural IgM stimulating activity and thus increase the dosing threshold.

In some embodiments, a method for reducing ABC of lipid LNPs encapsulating an mRNA can be performed by at least (i) administering to a subject in need thereof a first dose of the LNPs, and (ii) administering to the subject a second dose of the LNPs; wherein the first dose, the second dose, or both are equal to or less than about 0.3 mg/kg. For example, the first dose, the second dose, or both can be equal to or less than 0.2 mg/kg or 0.1 mg/kg. In some examples, the first dose, the second dose, or both, can range from about 0.1-0.3 mg/kg. The interval between the first dose and the second dose can be less than 2 weeks, e.g, less than 10 days, less than 1 week, less than 4 days, or less than 2 days. When subsequent doses are required, the same low doses described herein may be used. The interval between two consecutive doses may be less than 2 weeks, for example, less than 10 days, less than 1 week, less than 4 days, or less than 2 days.

Dose-limiting toxicity, such as CARPA, refers to side effects of a drug or other treatment that are serious enough to prevent an increase in dose or level of treatment. It is contemplated that using treatment regimens that could maintain the serum level of LNPs below the threshold for triggering clinically significant dose-limiting toxicity would reduce such toxicity or prevent its occurrence.

Accordingly, provided herein is a method for delivering lipid nanoparticles (LNPs) encapsulating an mRNA to a subject without promoting LNP-related toxicity. Such a method comprises administering an amount of the LNPs to a subject during a period, wherein the serum level of the LNPs in the subject during the administration period is not sufficient to induce LNP-related toxicity. The LNP-related toxicity may be coagulopathy, disseminated intravascular coagulation (DIC), vascular thrombosis, activation-related pseudoallergy (CARPA), acute phase response (APR), or a combination thereof.

It is within the knowledge of those skilled in the art to select suitable doses of the mRNA-encapsulating LNPs and the duration of the administration (e.g., infusion) so as to maintain the serum level of the LNPs below the threshold. For example, when a large dose is needed to reach the intended therapeutic effects, a longer administration period can be used. Occurrence of any of the dose-limiting toxicity can be monitored via conventional approaches in medical practice. The dose and administration period can be adjusted upon showing of any symptom associated with the toxicity. In some examples, the dose of the LNPs may be lower than 1 mg/kg, e.g., 0.5 mg/kg, 0.3 mg/kg, 0.2 mg/kg, or 0.1 mg/kg. In other examples, the LNP dose may range from 0.5 to 1 mg/kg (e.g., 0.3 to 0.5 mg/kg). The administration period may range from 30 minutes to 3 hours, for example 1-2 hours. In some instances, the administration period is no less than 1 hour, for example, no less than 1.5 hours, no less than 2 hours, no less than 2.5 hours, or no less than 3 hours.

In any of the methods described herein, the mRNA encapsulated in LNPs can be a therapeutic mRNA, which may code for a therapeutic protein. The mRNA encapsulated in LNPs may also be an mRNA encoding a vaccine antigen. In some instances, the mRNA encapsulated in LNPs may encode multiple proteins. In some embodiments, the LNPs used in this method can be any of the LNPs described herein.

In some aspects the invention encompasses one or more of the following embodiments:

1. A method of reducing or inhibiting an anti-drug antibody response in a subject, comprising subcutaneously administering to the subject a modified messenger RNA (mmRNA) encoding a polypeptide of interest, wherein the mmRNA comprises: (i) at least one miR-142-3p microRNA binding site; (ii) at least one miR-126 binding site; or (iii) at least one miR-142-3p microRNA binding site and at least one miR-126 binding site, and wherein to the mmRNA comprises one or more modified nucleobases, such that an anti-drug antibody response to the polypeptide of interest is reduced or inhibited in the subject.
2. The method of embodiment 1, wherein the mmRNA is administered encapsulated in a lipid nanoparticle.
3. The method of embodiment 2, wherein the mmRNA is administered by once weekly subcutaneous administration.
4. The method of any of the preceding embodiments wherein the mmRNA comprises a 5' UTR, a codon optimized open reading frame encoding the polypeptide of interest, a 3' UTR comprising (i) the at least one miR-142-3p microRNA binding site; (ii) the at least one miR-126 binding site; or (iii) the at least one miR-142-3p microRNA binding site and at least one miR-126 binding site, and a 3' tailing region of linked nucleosides.

5. The method of any of the preceding embodiments wherein the mmRNA comprises a 5' UTR and 3'UTR which are heterologous to the coding region.

6. The method of any of the preceding embodiments wherein the mmRNA is fully modified.

7. The method of any of the preceding embodiments wherein the mmRNA comprises pseudouridine ($\psi$), pseudouridine ($\psi$) and 5-methyl-cytidine ($m^5C$), 1-methyl-pseudouridine ($m^1\psi$), 1-methyl-pseudouridine ($m^1\psi$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).

8. The method of any of the preceding embodiments wherein the mmRNA comprises pseudouridine ($\psi$), N1-methylpseudouridine ($m^1\psi$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.

9. The method of any of the preceding embodiments wherein the mmRNA comprises 1-methyl-pseudouridine ($m_1\psi$), 5-methoxy-uridine ($mo^5U$), 5-methyl-cytidine ($m^5C$), pseudouridine ($\psi$), α-thio-guanosine, or α-thio-adenosine, or combinations thereof.

10. The method of any of the preceding embodiments wherein the polypeptide of interest is a therapeutic protein, cytokine, growth factor, antibody or fusion protein.

11. The method of any of the preceding embodiments wherein lipid nanoparticle is a liposome.

12. The method of any of the preceding embodiments wherein lipid nanoparticle comprises a cationic and/or ionizable lipid.

13. The method of embodiment 12, wherein the cationic and/or ionizable lipid is DLin-KC2-DMA or DLin-MC3-DMA.

14. The method of any of one of embodiments 1-13, wherein the mmRNA comprises at least one miR-142-3p microRNA binding site comprising the sequence shown in SEQ ID NO: 3.

15. The method of any one of embodiments 1-13, wherein the mmRNA comprises at least two microRNA binding sites, wherein at least one of the microRNA binding sites is a miR-142-3p microRNA binding site.

16. The method of embodiment 15, wherein the mmRNA comprises a miR-142-3p binding site and a second microRNA binding site for a miR selected from the group consisting of miR-142-5p, miR-146-3p, miR-146-5p, miR-155, miR-126, miR-16, miR-21, miR-223, miR-24 and miR-27.

17. The method of any one of embodiments 1-13, wherein the mmRNA comprises at least one miR-126 microRNA binding site comprising the sequence shown in SEQ ID NO: 26.

18. The method of any one of embodiments 1-13, wherein the mmRNA comprises at least two microRNA binding sites, wherein at least one of the microRNA binding sites is a miR-126 microRNA binding site.

19. The method of embodiment 18, wherein the mmRNA comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27.

20. The method of any one of embodiments 1-13, wherein the mmRNA construct comprises a miR-126 binding site and a miR-142-3p binding site.

21. The method of any one of embodiments 1-13, wherein the mmRNA construct comprises three miR-142-3p binding sites.

22. The method of any one of embodiments 1-13, wherein the mmRNA construct comprises three miR-126 binding sites.

23. The method of any one of embodiments 1-13, wherein the codon optimized open reading frame encoding the polypeptide of interest comprises a stop codon and wherein the (i) at least one miR-142-3p microRNA binding site; (ii) at least one miR-126 binding site; or (iii) at least one miR-142-3p microRNA binding site and at least one miR-126 binding site is located within the 3' UTR 30-50 nucleotides after the stop codon.

24. The method of any one of embodiments 1-13, wherein the codon optimized open reading frame encoding the polypeptide of interest comprises a stop codon and wherein the (i) at least one miR-142-3p microRNA binding site; (ii) at least one miR-126 binding site; or (iii) at least one miR-142-3p microRNA binding site and at least one miR-126 binding site is located within the 3' UTR at least 50 nucleotides after the stop codon.

25. The method of any one of embodiments 1-13, wherein the (i) at least one miR-142-3p microRNA binding site; (ii) at least one miR-126 binding site; or (iii) at least one miR-142-3p microRNA binding site and at least one miR-126 binding site is located within a 5' UTR of the mmRNA construct.

26. A method of reducing or inhibiting an anti-drug antibody response following repeated administration of a polypeptide of interest to a subject, comprising administering to the subject intravenously a first dose of a modified mRNA (mmRNA) encoding a polypeptide of interest encapsulated in an LNP, wherein the mmRNA comprises: (i) at least one miR-142-3p microRNA binding site; (ii) at least one miR-126 binding site; or (iii) at least one miR-142-3p microRNA binding site and at least one miR-126 binding site, and wherein the mmRNA comprises one or more modified nucleobases;

and administering to the subject subcutaneously a subsequent dose of the mmRNA encapsulated in an LNP, such that an anti-drug antibody response to the polypeptide of interest is reduced or inhibited in the subject.

27. A method of reducing or inhibiting an anti-drug antibody response following repeated administration of a polypeptide of interest to a subject, comprising (i) administering to the subject intravenously a first dose of a modified mRNA (mmRNA) encoding a polypeptide of interest encapsulated in an LNP, wherein the mmRNA comprises: (i) at least one miR-142-3p microRNA binding site; (ii) at least one miR-126 binding site; or (iii) at least one miR-142-3p microRNA binding site and at least one miR-126 binding site, and wherein the mmRNA comprises one or more modified nucleobases;

(ii) detecting a level of anti-drug antibodies in a sample from the subject; and (iii) administering to the subject subcutaneously a subsequent dose of the mmRNA encapsulated in an LNP when the level of anti-drug antibodies in the sample is diminished, such that an anti-drug antibody response to the polypeptide of interest is reduced or inhibited in the subject.

28. A method of reducing or inhibiting drug-related toxicity in a subject, comprising administering to the subject a modified messenger RNA (mmRNA) encoding a polypeptide of interest, wherein the mmRNA comprises: (i) at least one miR-142-3p microRNA binding site; (ii) at least one miR-126 binding site; or (iii) at least one miR-142-3p microRNA binding site and at least one miR-126 binding site, and wherein the mmRNA comprises one or more modified nucleobases, such that drug-related toxicity to the polypeptide of interest is reduced or inhibited in the subject.

29. A method of reducing or inhibiting unwanted immune cell activation in a subject administered a messenger RNA (mRNA) encoding a polypeptide of interest, the method comprising administering to the subject a chemically modified mRNA encoding the polypeptide of interest, wherein the chemically modified mRNA comprises at least one microRNA binding site for a microRNA expressed in immune cells, and wherein the chemically modified mRNA comprises one or more modified nucleobases, such that unwanted immune cell activation is reduced or inhibited in the subject.

30. The method of embodiment 29, wherein reduction or inhibition of unwanted immune cell activation is determined compared to control administration of a chemically modified mRNA lacking the at least one microRNA binding site.

31. The method of embodiment 29, wherein the reduction or inhibition of unwanted immune cell activation is reduction or inhibition of lymphocyte activation.

32. The method of embodiment 31, wherein the reduction or inhibition of lymphocyte activation is reduction or inhibition of B cell activation.

33. The method of embodiment 32, wherein reduction or inhibition of B cell activation is determined by frequency of $CD19^+$ $CD86^+$ $CD69^+$ B cells.

34. The method of any one of embodiments 29-33, wherein the reduction or inhibition of unwanted immune cell activation causes reduced or inhibited cytokine production.

35. The method of any one of embodiment 29-34, wherein immune cell activation is decreased without a corresponding decrease in expression of the polypeptide of interest encoded by the chemically modified mRNA.

36. A method of reducing or inhibiting unwanted cytokine production in a subject administered a messenger RNA (mRNA) encoding a polypeptide of interest, the method comprising administering to the subject a chemically modified mRNA encoding the polypeptide of interest, wherein the chemically modified mRNA comprises at least one microRNA binding site for a microRNA expressed in immune cells, and wherein the chemically modified mRNA comprises one or more modified nucleobases, such that unwanted cytokine production is reduced or inhibited in the subject.

37. The method of embodiment 36, wherein reduction or inhibition of unwanted cytokine production is determined compared to control administration of a chemically modified mRNA lacking the at least one microRNA binding site for a microRNA expressed in immune cells.

38. The method of embodiment 36, wherein the reduced or inhibited cytokine production is reduced or inhibited production of interleukin-6 (IL-6), tumor necrosis factor α (TNF-α) or interferon-γ (IFN-γ).

39. The method of embodiment 36, wherein the reduced or inhibited cytokine production is reduced or inhibited production of interleukin-6 (IL-6).

40. The method of any one of embodiment 36-39, wherein cytokine production is decreased without a corresponding decrease in expression of the polypeptide of interest encoded by the chemically modified mRNA.

41. The method of embodiment any one of embodiments 29-40, wherein the chemically modified mRNA is administered subcutaneously encapsulated in a lipid nanoparticle.

42. The method of embodiment 41, wherein the chemically modified mRNA is administered by once weekly administration.

43. The method of any one of embodiments 29-42 wherein the chemically modified mRNA comprises a 5' UTR, a codon optimized open reading frame encoding the polypeptide of interest, a 3' UTR comprising the at least one microRNA binding site, and a 3' tailing region of linked nucleosides.

44. The method of embodiment 43, wherein the chemically modified mRNA comprises a 5' UTR and 3'UTR which are heterologous to the open reading frame.

45. The method of any one of embodiments 29-44, wherein the mRNA is fully modified.

46. The method of any of embodiments 29-45, wherein the mRNA comprises pseudouridine (ψ), pseudouridine (ψ) and 5-methyl-cytidine ($m^5C$), 1-methyl-pseudouridine ($m^1ψ$), 1-methyl-pseudouridine ($m^1ψ$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).

47. The method of any of one of embodiments 29-46, wherein the mRNA comprises pseudouridine (ψ), N1-methylpseudouridine ($m^1ψ$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.

48. The method of any of embodiments 29-47, wherein the m RNA comprises 1-methyl-pseudouridine ($m^1ψ$), 5-methoxy-uridine ($mo^5U$), 5-methyl-cytidine ($m^5C$), pseudouridine (ψ), α-thio-guanosine, or α-thio-adenosine, or combinations thereof.

49. The method of any one of embodiments 29-48, wherein the microRNA binding site binds a microRNA expressed in myeloid cells.

50. The method of any one of embodiments 29-48, wherein the microRNA binding site binds a microRNA expressed in plasmacytoid dendritic cells.

51. The method of any one of embodiments 29-48, wherein the microRNA binding site binds a microRNA expressed in macrophages.

52. The method of any one of embodiments 29-48, wherein the microRNA binding site is a miR-126 microRNA binding site.

53. The method of embodiment 52, wherein the miR-126 microRNA binding site comprises the sequence shown in SEQ ID NO: 26.

54. The method of any one of embodiments 29-48, wherein the microRNA binding site is a miR-142 microRNA binding site.

55. The method of embodiment 54, wherein the miR-142 microRNA binding site comprises the sequence shown in SEQ ID NO: 3.

56. The method of any one of embodiments 29-48, wherein the microRNA binding site is a miR-155 microRNA binding site.

57. The method of embodiment 56, wherein the miR-155 microRNA binding site comprises the sequence shown in SEQ ID NO: 35.

58. The method of any one of embodiments 29-57, wherein the polypeptide of interest is a therapeutic protein, cytokine, growth factor, antibody or fusion protein.

59. The method of any one of embodiments 29-58, wherein the chemically modified mRNA comprises at least two microRNA binding sites.

60. The method of embodiment 59, wherein at least one of the microRNA binding sites is a miR-126 microRNA binding site.

61. The method of embodiment 60, wherein the chemically modified mRNA comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27.

62. The method of embodiment 60, wherein the chemically modified mRNA comprises a miR-126 binding site and a miR-142 binding site.

63. The method of embodiment 41, wherein the lipid nanoparticle is a liposome.

64. The method of embodiment 41, wherein the lipid nanoparticle comprises a cationic and/or ionizable lipid.

65. The method of embodiment 64, wherein the cationic and/or ionizable lipid is DLin-KC2-DMA or DLin-MC3-DMA.

66. A method of reducing or inhibiting unwanted immune cell activation in a subject administered a messenger RNA (mRNA) encoding a polypeptide of interest, comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases;
and administering to the subject subcutaneously a subsequent dose of the chemically modified mRNA encapsulated in an LNP, such that unwanted immune cell activation is reduced or inhibited in the subject.

67. A method of reducing or inhibiting unwanted immune cell activation in a subject following repeated administration of a messenger RNA (mRNA) encoding a polypeptide of interest to the subject, comprising
(i) administering to the subject intravenously a first dose of a chemically modified mRNA encapsulated in a lipid nanoparticle (LNP), wherein the chemically modified mRNA comprises at least one microRNA binding site for a microRNA expressed in immune cells, and wherein the chemically modified mRNA comprises one or more modified nucleobases;
(ii) detecting a level of immune cell activation in a sample from the subject; and
(iii) administering to the subject subcutaneously a subsequent dose of the chemically modified mRNA encapsulated in an LNP when the level of immune cell activation in the sample is diminished, such that unwanted immune cell activation is reduced or inhibited in the subject.

68. The method of embodiment 66 or 67, wherein the reduced or inhibited unwanted immune cell activation is reduced or inhibited B cell activation.

69. The method of embodiment 66 or 67, wherein the reduced or inhibited unwanted immune cell activation causes reduced or inhibited cytokine production.

70. A method of reducing or inhibiting accelerated blood clearance in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that accelerated blood clearance is reduced or inhibited in the subject upon repeat administration.

71. A method of reducing or inhibiting accelerated blood clearance in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases;
and administering to the subject subcutaneously a subsequent dose of the chemically modified mRNA encapsulated in an LNP, such that accelerated blood clearance is reduced or inhibited in the subject.

72. The method of anyone of embodiments 70-71, wherein the mRNA encoding a polypeptide of interest encapsulated in a lipid nanoparticle (LNP) does not activate B cells and/or does not induce production of IgM molecules capable of binding to the LNP.

73. The method of any one of embodiments 70-72, wherein reduction or inhibition of accelerated blood clearance is determined compared to control administration of a chemically modified mRNA lacking the at least one microRNA binding site encapsulated in a lipid nanoparticle (LNP).

74. The method of any one of embodiments 70-73, wherein accelerated blood clearance is reduced or inhibited without a corresponding reduction or inhibition in expression of the polypeptide of interest encoded by the chemically modified mRNA.

75. The method of any one of embodiments 70-74, wherein the interval between two consecutive doses is less than 2 weeks.
76. The method of embodiment 75, wherein the interval between two consecutive doses is less than 1 week.
77. A method of reducing or inhibiting production of IgM molecules that recognize polyethylene glycol (PEG) in a subject repeatedly administered a messenger RNA (mRNA) encoding a polypeptide of interest encapsulated in an lipid nanoparticle (LNP), the method comprising administering to the subject a chemically modified mRNA encoding the polypeptide of interest encapsulated in an lipid nanoparticle (LNP), wherein the chemically modified mRNA comprises at least one microRNA binding site for a microRNA expressed in immune cells, and wherein the chemically modified mRNA comprises one or more modified nucleobases, such that production of IgM molecules that recognize PEG are reduced or inhibited in the subject upon repeat administration.
78. A method of reducing or inhibiting production of IgM molecules that recognize polyethylene glycol (PEG) in a subject administered a messenger RNA (mRNA) encoding a polypeptide of interest encapsulated in an lipid nanoparticle (LNP), comprising administering to the subject intravenously a first dose of a chemically modified mRNA encapsulated in an lipid nanoparticle (LNP), wherein the chemically modified mRNA comprises at least one microRNA binding site for a microRNA expressed in immune cells, and wherein the chemically modified mRNA comprises one or more modified nucleobases;
and administering to the subject subcutaneously a subsequent dose of the chemically modified mRNA encapsulated in an LNP, such that production of IgM molecules that recognize PEG are reduced or inhibited in the subject.
79. The method of any one of embodiments 70-78, wherein the chemically modified mRNA comprises a 5' UTR, a codon optimized open reading frame encoding the polypeptide of interest, a 3' UTR comprising the at least one microRNA binding site, and a 3' tailing region of linked nucleosides.
80. The method of embodiment 79, wherein the chemically modified mRNA comprises a 5' UTR and 3'UTR which are heterologous to the open reading frame.
81. The method of any one of embodiments 70-80, wherein the mRNA is fully modified.
82. The method of any one of embodiments 70-81, wherein the mRNA comprises pseudouridine (ψ), pseudouridine (ψ) and 5-methyl-cytidine ($m^5C$), 1-methyl-pseudouridine ($m^1ψ$), 1-methyl-pseudouridine ($m^1ψ$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).
83. The method of any one of embodiments 70-82, wherein the mRNA comprises pseudouridine (ψ), N1-methylpseudouridine ($m^1ψ$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.
84. The method of any one of embodiments 70-83, wherein the mRNA comprises 1-methyl-pseudouridine ($m_1ψ$), 5-methoxy-uridine ($mo^5U$), 5-methyl-cytidine ($m^5C$), pseudouridine (ψ), α-thio-guanosine, or α-thio-adenosine, or combinations thereof.
85. The method of any one of embodiments 70-84, wherein the microRNA binding site binds a microRNA expressed in myeloid cells.
86. The method of any one of embodiments 70-84, wherein the microRNA binding site is a miR-142 microRNA binding site
87. The method of embodiment 86, wherein the miR-142 microRNA binding site comprises the sequence shown in SEQ ID NO: 3.
88. The method of any one of embodiments 70-84, wherein the microRNA binding site binds a microRNA expressed in plasmacytoid dendritic cells.
89. The method of any one of embodiments 70-84, wherein the microRNA binding site is a miR-126 microRNA binding site
90. The method of embodiment 89, wherein the miR-126 microRNA binding site comprises the sequence shown in SEQ ID NO: 26.
91. The method of any one of embodiments 70-84, wherein the microRNA binding site binds a microRNA expressed in macrophages.
92. The method of any one of embodiments 70-84, wherein the microRNA binding site is a miR-155 microRNA binding site.
93. The method of embodiment 92, wherein the miR-155 microRNA binding site comprises the sequence shown in SEQ ID NO: 35.
94. The method of any one of embodiments 70-93, wherein the polypeptide of interest is a therapeutic protein, cytokine, growth factor, antibody or fusion protein.
95. The method of any one of embodiments 70-94, wherein the chemically modified mRNA comprises at least two microRNA binding sites.
96. The method of embodiment 95, wherein at least one of the microRNA binding sites is a miR-126 microRNA binding site.
97. The method of embodiment 96, wherein the chemically modified mRNA comprises a miR-126 binding site and a second microRNA binding site for a miR selected from the group consisting of miR-142-3p, miR-142-5p, miR-146-3p, miR-146-5p, miR-155, miR-16, miR-21, miR-223, miR-24 and miR-27.
98. The method of embodiment 96, wherein the chemically modified mRNA comprises a miR-126 binding site and a miR-142 binding site.
99. The method of any one embodiments 70-98, wherein the lipid nanoparticle is a liposome.
100. The method of any one embodiments 70-98, wherein the lipid nanoparticle comprises a cationic and/or ionizable lipid.
101. The method of embodiment 100, wherein the cationic and/or ionizable lipid is DLin-KC2-DMA or DLin-MC3-DMA.
102. A modified messenger RNA (mmRNA) encoding a polypeptide of interest, wherein the mmRNA comprises at least two different microRNA (miR) binding sites, wherein the microRNA is expressed in an immune cell of hematopoietic lineage or a cell that expresses TLR7 and/or TLR8 and secretes pro-inflammatory cytokines and/or chemokines, and wherein the mmRNA comprises one or more modified nucleobases.

103. The mmRNA of embodiment 102, wherein the immune cell of hematopoietic lineage is a lymphoid cell, such as a T cell, B cell, or NK cell.

104. The mmRNA of embodiment 102, wherein the immune cell of hematopoietic lineage is a myeloid cell, such as a monocyte, macrophage, neutrophil, basophil, eosinophil, erythrocyte, dendritic cell, megakaryocyte, or platelet.

105. The mmRNA of embodiment 102, wherein the immune cell of hematopoietic lineage is a hematopoietic progenitor cell.

106. The mmRNA of embodiment 102, wherein the cell that expresses TLR7 and/or TLR8 and secretes pro-inflammatory cytokines and/or chemokines is an endothelial cell.

107. The mmRNA of any one of embodiments 102-106, wherein the microRNA is abundant in the same or different cell type of interest.

108. The mmRNA of any one of embodiments 102-106, wherein the microRNA is abundant in multiple cell types of interest.

109. The mmRNA of embodiment 102, wherein the mmRNA comprises at least one first microRNA binding site of a microRNA abundant in an immune cell of hematopoietic lineage and at least one second microRNA binding site is of a microRNA abundant in endothelial cells 110. The mmRNA of embodiment 102, wherein the mmRNA comprises at least one first microRNA binding site of a microRNA abundant in B cells and at least one second microRNA binding site of a microRNA abundant in endothelial cells.

111. The mmRNA of embodiment 102, wherein the mmRNA comprises at least one first microRNA binding site of a microRNA abundant in plasmacytoid dendritic cells and at least one second microRNA binding site of a microRNA abundant in endothelial cells.

112. The mmRNA of any one of embodiments 102-111, wherein the mmRNA comprises multiple copies of a first microRNA binding site and at least one copy of a second microRNA binding site.

113. The mmRNA of embodiment 112, wherein the mmRNA comprises 2 copies of the first microRNA binding site.

114. The mmRNA of embodiment any one of embodiments 102-111, wherein the mmRNA comprises first and second microRNA binding sites of the same microRNA.

115. The mmRNA of embodiment 114, wherein the microRNA binding sites are of the 3p and 5p arms of the same microRNA.

116. The mmRNA of embodiment 102, wherein the microRNA is selected from the group consisting of miR-126, miR-142, miR-144, miR-146, miR-150, miR-155, miR-16, miR-21, miR-223, miR-24, miR-27 and miR-26a.

117. The mmRNA of embodiment 102, wherein the microRNA is selected from the group consisting of miR126-3p, miR-142-3p, miR-142-5p, and miR-155.

118. The mm RNA of embodiment 102, wherein at least one microRNA binding site is a miR-126 binding site.

119. The mmRNA of embodiment 102, wherein at least one microRNA binding site is a miR-142 binding site.

120. The mmRNA of embodiment 102, wherein one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27.

121. The mmRNA of embodiment 102, comprising at least one miR-126-3p binding site and at least one miR-142-3p binding site.

122. The mmRNA of embodiment 102, comprising at least one miR-142-3p binding site and at least one 142-5p binding site.

123. The mmRNA of embodiment 102, comprising at least three different microRNA binding sites, wherein at least one of the microRNA binding sites is a miR-126 binding site.

124. The mmRNA of embodiment 102, comprising at least three different microRNA binding sites, wherein at least one of the microRNA binding sites is a miR-142 binding site.

125. The mmRNA of embodiment 102, comprising at least one miR-126-3p binding site, at least one miR-142-3p, and a third microRNA binding site for a microRNA selected from the group consisting of miR-146-3p, miR-146-5p, miR-155, miR-16, miR-21, miR-223, miR-24 and miR-27.

126. The mmRNA of embodiment 102, comprising at least one miR-126-3p binding site, at least one miR-142-3p binding site, and at least one miR-155 binding site.

127. The mmRNA of embodiment 102, comprising at least one miR-126-3p binding site, at least one miR-142-3p binding site, at least one miR-142-5p binding site, and at least one miR-155 binding site.

128. The mmRNA of any of the preceding embodiments, wherein the microRNA binding sites are located in the 5' UTR, 3' UTR, or both the 5' UTR and 3' UTR of the mmRNA.

129. The mmRNA of embodiment 128, wherein the microRNA binding sites are located in the 3' UTR of the mmRNA.

130. The mmRNA of embodiment 128, wherein the microRNA binding sites are located in the 5' UTR of the mmRNA.

131. The mmRNA of embodiment 128, wherein the microRNA binding sites are located in both the 5' UTR and 3' UTR of the mmRNA.

132. The mmRNA of embodiment 128, wherein at least one microRNA binding site is located in the 3' UTR immediately adjacent to the stop codon of the coding region of the mmRNA.

133. The mmRNA of embodiment 128, wherein at least one microRNA binding site is located in the 3' UTR 70-80 bases downstream of the stop codon of the coding region of the mmRNA.

134. The mmRNA of embodiment 128, wherein at least one microRNA binding site is located in the 5' UTR immediately preceding the start codon of the coding region of the mmRNA.

135. The mmRNA of embodiment 128, wherein at least one microRNA binding site is located in the 5' UTR 15-20 nucleotides preceding the start codon of the coding region of the mmRNA.

136. The mmRNA of embodiment 128, wherein at least one microRNA binding site is located in the 5' UTR 70-80 nucleotides preceding the start codon of the coding region of the mmRNA.
137. The mmRNA of embodiment 128, wherein the mmRNA comprises multiple copies of the same microRNA binding site positioned immediately adjacent to each other or with a spacer of less than 5, 5-10, 10-15, or 15-20 nucleotides.
138. The mmRNA of embodiment 128, wherein the mmRNA comprises multiple copies of the same microRNA binding site located in the 3' UTR, wherein the first microRNA binding site is positioned immediately adjacent to the stop codon and the second and third microRNA binding sites are positioned 30-40 bases downstream of the first microRNA binding site.
139. The mmRNA of embodiment 128, wherein the mmRNA comprises 2 copies of a first microRNA binding site and 1 copy of a second microRNA binding site located in the 3' UTR, wherein the first copy of the first microRNA binding site is positioned immediately adjacent to the stop codon, the second microRNA binding site is positioned 30-40 bases downstream of the first copy of the first microRNA binding site, and the second copy of the first microRNA binding site is positioned 30-40 bases downstream of the second microRNA binding site
140. The mmRNA of any of the preceding embodiments, wherein the mmRNA is fully modified.
141. The mmRNA of any of the preceding embodiments wherein the mmRNA comprises pseudouridine (ψ), pseudouridine (ψ) and 5-methyl-cytidine ($m^5C$), 1-methyl-pseudouridine ($m^1\psi$), 1-methyl-pseudouridine ($m^1\psi$) and 5-methyl-cytidine ($m^5C$), 2-thiouridine ($s^2U$), 2-thiouridine and 5-methyl-cytidine ($m^5C$), 5-methoxy-uridine ($mo^5U$), 5-methoxy-uridine ($mo^5U$) and 5-methyl-cytidine ($m^5C$), 2'-O-methyl uridine, 2'-O-methyl uridine and 5-methyl-cytidine ($m^5C$), N6-methyl-adenosine ($m^6A$) or N6-methyl-adenosine ($m^6A$) and 5-methyl-cytidine ($m^5C$).
142. The mmRNA of any of the preceding embodiments wherein the mmRNA comprises pseudouridine (ψ), N1-methylpseudouridine ($m^1\psi$), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.
143. The mmRNA of any of the preceding embodiments wherein the mmRNA comprises 1-methyl-pseudouridine ($m^1\psi$), 5-methoxy-uridine ($mo^5U$), 5-methyl-cytidine ($m^5C$), pseudouridine (ψ), α-thio-guanosine, or α-thio-adenosine, or combinations thereof.
144. The mmRNA of any of the preceding embodiments wherein the polypeptide of interest is a therapeutic protein, cytokine, growth factor, antibody or fusion protein.
145. A lipid nanoparticle comprising the mmRNA of any of the preceding embodiments.
146. The lipid nanoparticle of embodiment 145 wherein the lipid nanoparticle comprises a liposome.
147. The lipid nanoparticle of embodiment 145 wherein lipid nanoparticle comprises a cationic and/or ionizable lipid.
148. The lipid nanoparticle of embodiment 147, wherein the cationic and/or ionizable lipid is DLin-KC2-DMA or DLin-MC3-DMA.
149. A pharmaceutical composition comprising the mmRNA of any one of embodiments 102-144 or the lipid nanoparticle of any one of embodiments 145-148, and a pharmaceutically acceptable carrier, diluent or excipient.
150. The mmRNA according to any one of embodiments 102-144, the lipid nanoparticle according to any one of embodiments 145-148, or the pharmaceutical composition according to embodiment 149, for use in reducing or inhibiting an anti-drug antibody response or inhibiting drug-related toxicity in a subject in need thereof.
151. The mmRNA according to any one of embodiments 102-144, the lipid nanoparticle according to any one of embodiments 145-148 or the pharmaceutical composition according to embodiment 149, for use in reducing or inhibiting unwanted immune cell activation or reducing or inhibiting unwanted cytokine production in a subject in need thereof.
152. The mmRNA according to any one of embodiments 102-144, the lipid nanoparticle according to any one of embodiments 145-148 or the pharmaceutical composition according to embodiment 149, for use in reducing or inhibiting accelerated blood clearance in a subject in need thereof.
153. The mmRNA according to any one of embodiments 102-144, the lipid nanoparticle according to any one of embodiments 145-148 or the pharmaceutical composition according to embodiment 149, for use in reducing or inhibiting production of IgM molecules that recognize polyethylene glycol (PEG) in a subject in need thereof.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Repeat Dose IV/SC±MIR

In this study, the effects of repeat intravenous (IV) dosing followed by subcutaneous (SC) administration were examined. Female CD1 mice (n=8 per group) were given six doses of hEPO in different lipid nanoparticle formulations (0.5 mg/kg) either IV or SC weekly. After the six doses, the IV groups (groups 8-14) were given weekly SC doses for three weeks. The groups are shown in Table 1 below.

TABLE 1

Experimental Groups

| Group | Test/Control Material | Vehicle | Formulation | Route |
|---|---|---|---|---|
| 1 | Compound 18 | LNP | 50:10:38:5:1.5 | SC |
| 2 | Compound 18 EPO 142/126 | LNP | 50:10:38:5:1.5 | SC |

TABLE 1-continued

Experimental Groups

| Group | Test/Control Material | Vehicle | Formulation | Route |
|---|---|---|---|---|
| 3 | Compound 18 PEG Steric OH | LNP | 50:10:38:5:1.5 | SC |
| 4 | Compound 18 PEG Steric OH EPO 142/126 | LNP | 50:10:38:5:1.5 | SC |
| 5 | Compound 18 Oleic | LNP | 50:10:38:5:1.5 | SC |
| 6 | Compound 18 Oleic EPO 142/126 | LNP | 50:10:38:5:1.5 | SC |
| 7 | Compound 18 DSPE methoxy PEG | LNP | 50:10:38:5:1.5 | SC |
| 8 | Compound 18 | LNP | 50:10:38:5:1.5 | IV |
| 9 | Compound 18 EPO 142/126 | LNP | 50:10:38:5:1.5 | IV |
| 10 | Compound 18 PEG Steric OH | LNP | 50:10:38:5:1.5 | IV |
| 11 | Compound 18 PEG Steric OH EPO 142/126 | LNP | 50:10:38:5:1.5 | IV |
| 12 | Compound 18 Oleic | LNP | 50:10:38:5:1.5 | IV |
| 13 | Compound 18 Oleic EPO 142/126 | LNP | 50:10:38:5:1.5 | IV |
| 14 | Compound 18 DSPE methoxy PEG | LNP | 50:10:38:5:1.5 | IV |
| 15 | PBS | LNP | 50:10:38:5:1.5 | |
| 16 | Naïve | LNP | 50:10:38:5:1.5 | |

Blood samples were taken six hours after each dose, and the concentration of hEPO was measured. The hEPO concentrations from six doses of via IV (top) or SC (bottom) routes are shown in FIG. 1. The effect of MIR was more pronounced in the MIR+ SC groups.

Figure 2:
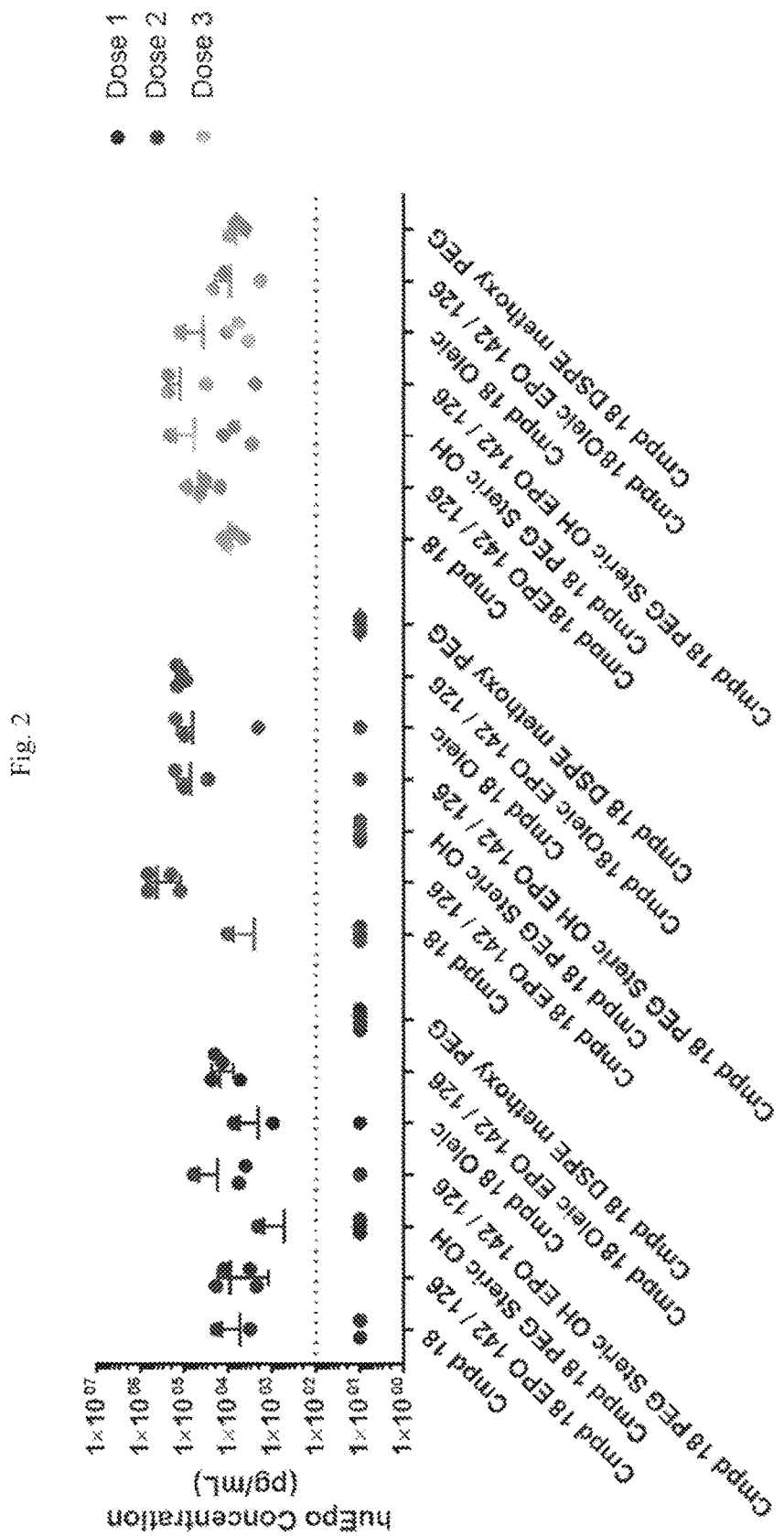
FIG. 2 is a graph showing the results of SC administration after six IV doses. The group receiving the Compound 18 PEG steric OH formulation was sacrificed after two doses, and the group receiving the Compound 18 DSPE methoxy PEG formulation was sacrificed after four doses.

In some groups, the mice were given six IV doses and then three weekly SC doses subsequently. The results are shown in FIG. 2. The effect of MIRs was found to be the most pronounced after two SC doses following the six IV doses.

Figure 3:
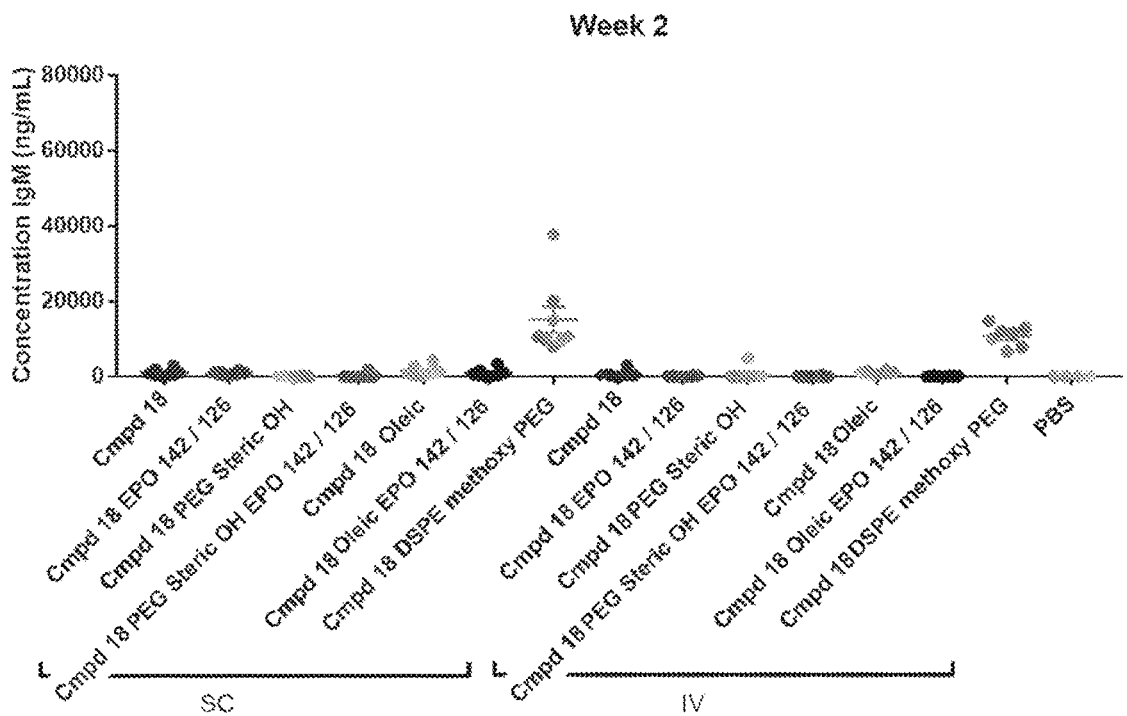
FIG. 3 shows the concentration of IgM in mice two weeks after SC or IV administration with the indicated formulations.
Figure 5:
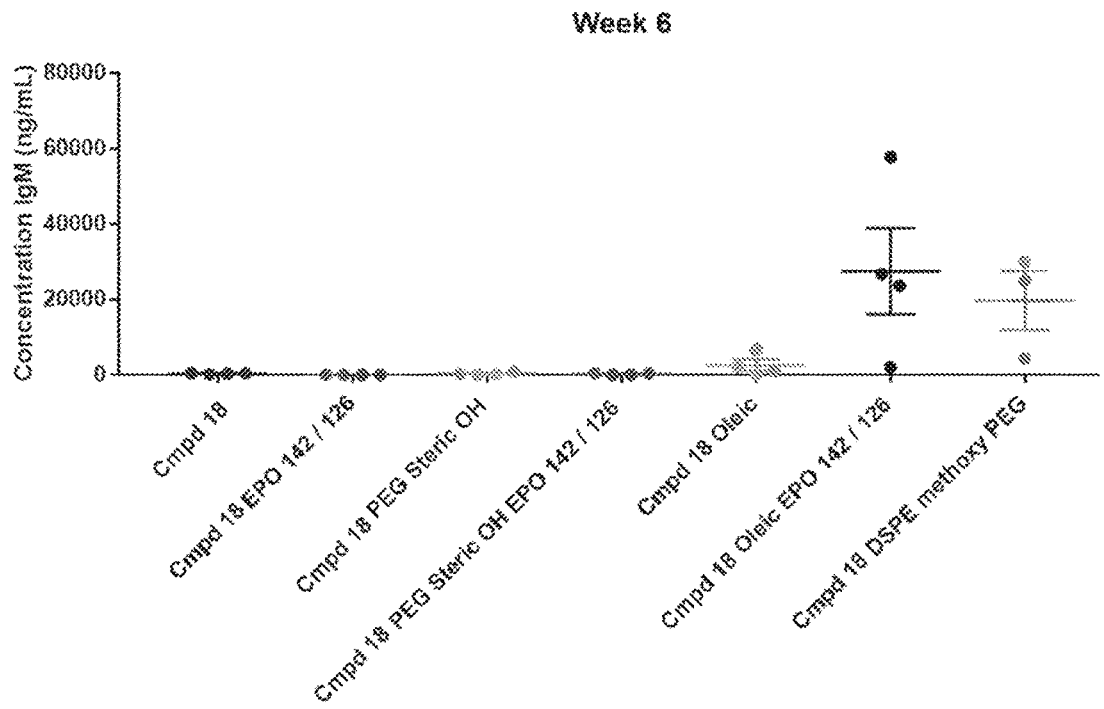
FIG. 5 shows the concentration of IgM in mice six weeks after SC administration with the indicated formulations (six total SC doses).
Figure 6:
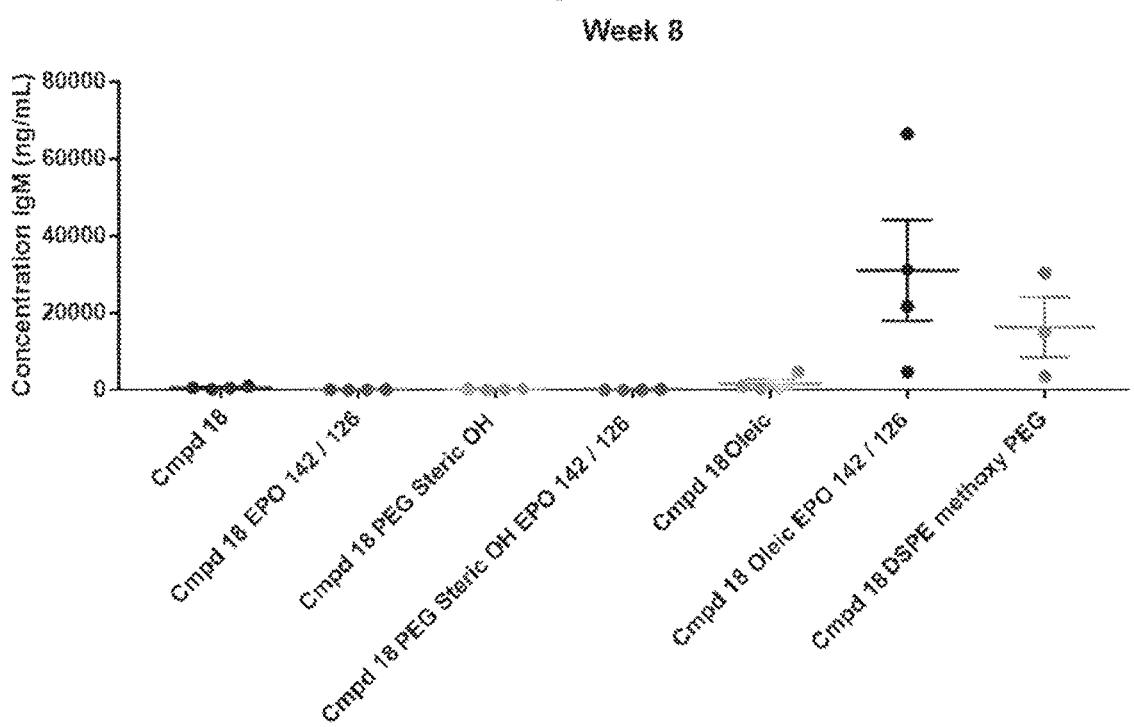
FIG. 6 shows the concentration of IgM in mice eight weeks after IV and SC administration with the indicated formulations. The mice were administered weekly IV doses for six consecutive weeks, followed by weekly SC doses for two consecutive weeks.

Anti-PEG IgM was also measured. Serum samples were diluted 1:100 and assayed using AGP4 standard mouse anti-PEG IgM. Median fluorescence intensity (MFI) with APC was used for quantification. The results after two weeks (FIG. 3), four weeks (FIG. 4), six weeks (FIG. 5; SC only), and eight weeks (FIG. 6; six IV doses and two SC doses), are given.

Example 2: Luciferase Repeat Dose SC Study

Figure 7:
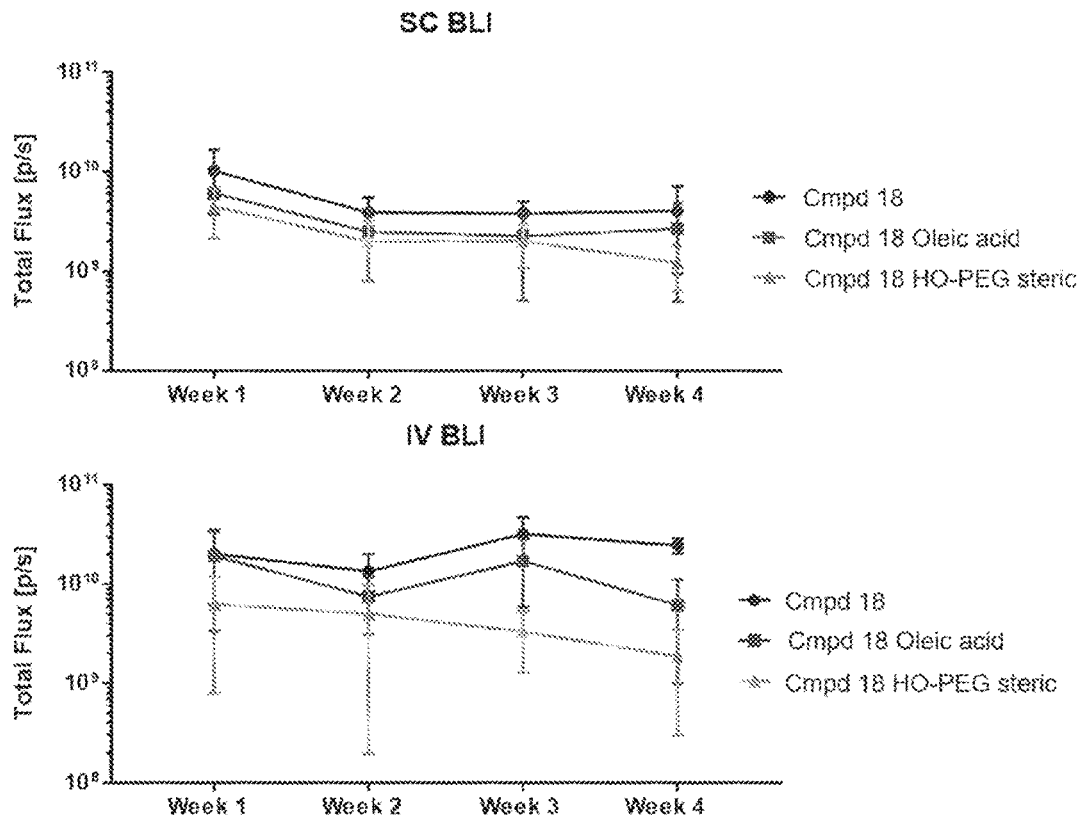
FIG. 7 shows the results of SC bioluminescence imaging (BLI) (top) and IV BLI (bottom) following luciferase administration at different time points.

In this experiment, mice were administered (either SC or IV) luciferase, an intracellular protein, in different lipid nanoparticle formulations (0.5 mg/kg) weekly as shown in FIG. 7. Bioluminescence imaging (BLI) was performed after each dose. No loss in protein expression after four doses with luciferase was detected, as the intracellular protein maintained expression regardless of the formulation tested. The groups are shown in Table 2 below.

TABLE 2

Experimental Groups

| Group | Test/Control Material | Vehicle | Formulation | Route |
|---|---|---|---|---|
| 1 | Compound 18 | LNP | 50:10:38:5:1.5 | SC |
| 2 | Compound 18 Oleic acid | LNP | 50:10:38:5:1.5 | SC |
| 3 | Compound 18 PEG Steric OH | LNP | 50:10:38:5:1.5 | SC |
| 4 | Compound 18 | LNP | 50:10:38:5:1.5 | IV |
| 5 | Compound 18 Oleic acid | LNP | 50:10:38:5:1.5 | IV |
| 6 | Compound 18 PEG Steric OH | LNP | 50:10:38:5:1.5 | IV |

After the first dose, five mice from each group were sacrificed and spleen, liver, draining lymph nodes, and the site of injections were imaged ex vivo. The remaining five animals from each group were sacrificed six hours after the final dose, and the spleen, liver, draining lymph node, and site of injection were imaged.

Example 3: Repeat Dose SC Expression after Administration in Nude Mice

In this experiment, BALB/c nude mice (groups 1-3) and BALB/c wild-type mice (groups 4-6) were administered hEPO, a secreted protein, formulated in different lipid nanoparticles at 0.5 mg/kg. The experimental groups are shown in Table 3 below.

TABLE 3

Experimental Groups

| Group | Test/Control Material | Vehicle | Formulation | Route |
|---|---|---|---|---|
| 1 | Compound 18 | LNP | 50:10:38:5:1.5 | SC |
| 2 | Compound 18 Oleic acid | LNP | 50:10:38:5:1.5 | SC |
| 3 | Compound 18 PEG Steric OH | LNP | 50:10:38:5:1.5 | SC |
| 4 | Compound 18 | LNP | 50:10:38:5:1.5 | SC |
| 5 | Compound 18 Oleic acid | LNP | 50:10:38:5:1.5 | SC |
| 6 | Compound 18 PEG Steric OH | LNP | 50:10:38:5:1.5 | SC |
| 7 | PBS BALB/c | | | SC |

Figure 8:
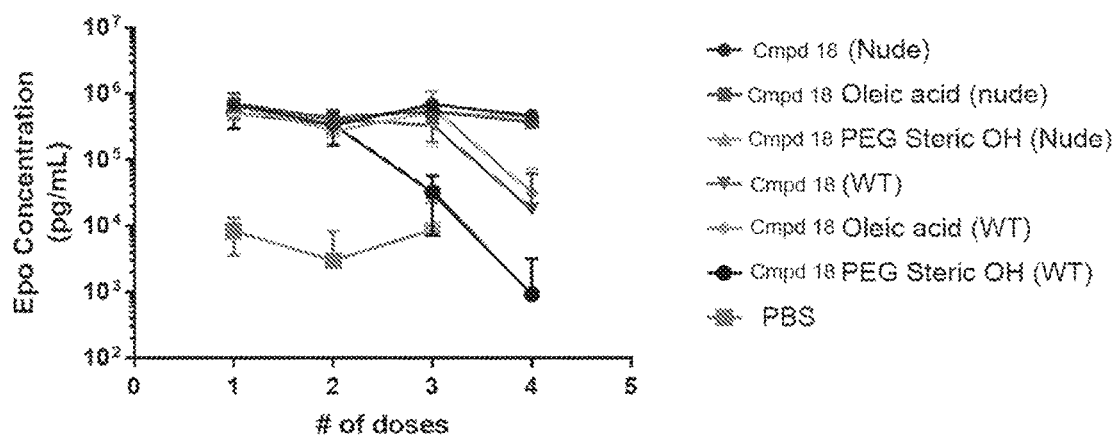
FIG. 8 shows hEPO concentration following repeated SC administration in nude and wild-type mice.
Figure 10:
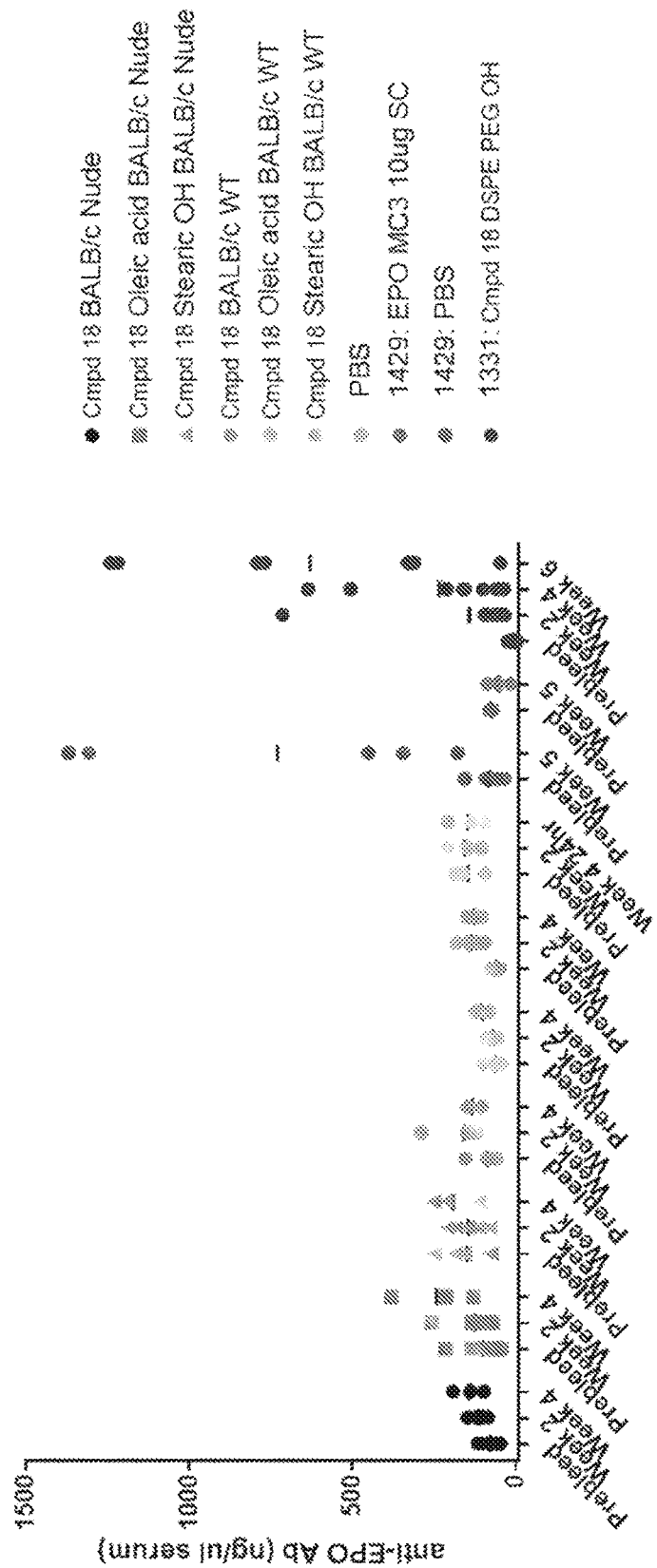
FIG. 10 shows the concentration of anti-EPO antibody in the serum of nude and wild-type mice. The SC positive controls underwent weekly dosing of 10 µg EPO protein during weeks 1-3, and then 10 µg EPO in lipid nanoparticles (LNP) on weeks 4 and 5.
Figure 11:
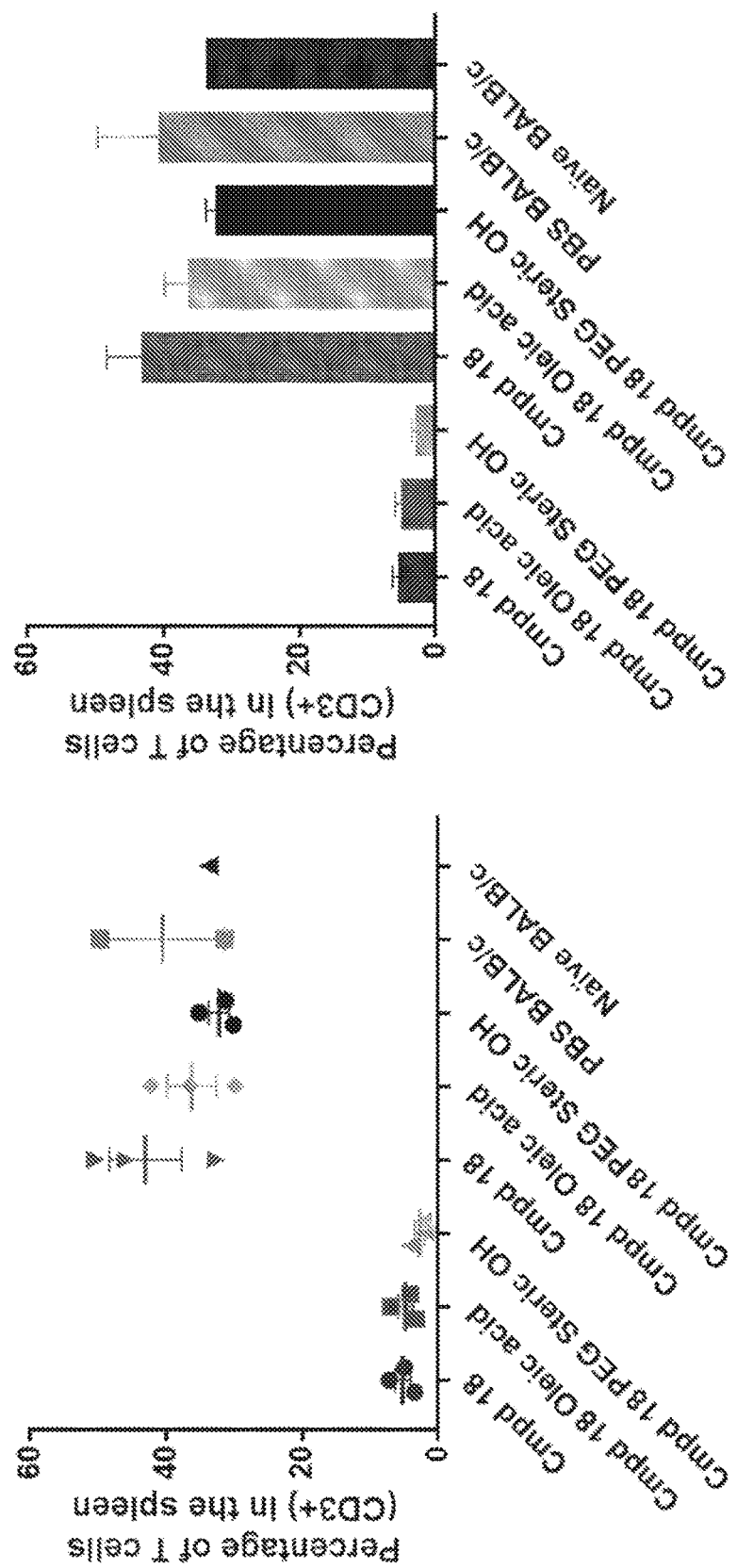
FIG. 11 shows T cell frequencies in different formulations.
Figure 12:
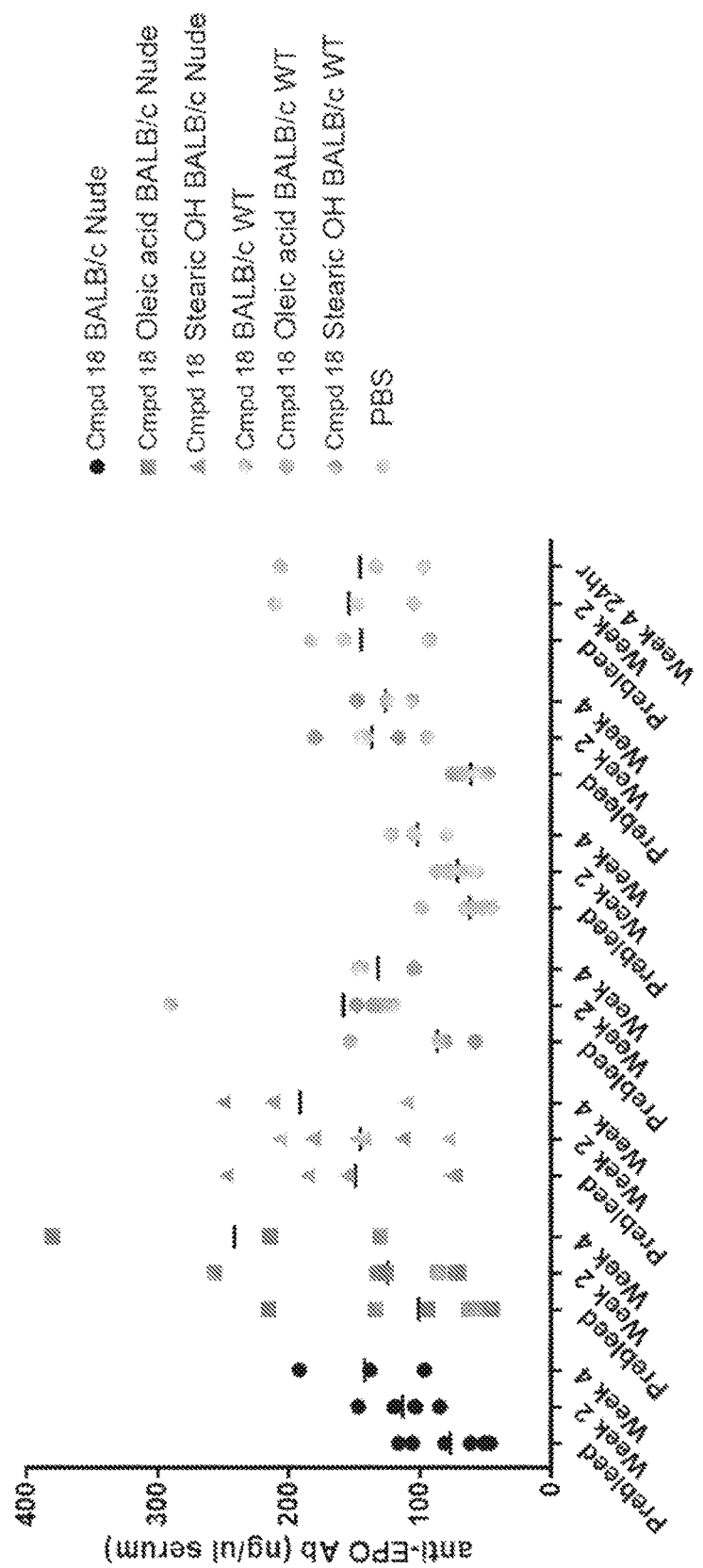
FIG. 12 shows anti-EPO antibody serum concentrations in nude and wild-type mice following SC injections of the indicated formulations at different time points.

As shown in FIG. 8, expression after SC administration showed no protein loss in nude mice; however, in wild-type mice, formulations containing PC or PEG modifications showed no increase in PEG IgM (FIG. 9) while protein expression dropped relative to earlier dosing. T cell frequencies, as shown in FIG. 11, demonstrate higher levels in BALB/c wild-type mice, as compared to nude mice. As shown in FIG. 10, anti-EPO antibody was consistently lower in the BALB/c wild-type mice. The results of an anti-EPO antibody ELISA, which are consistent, are shown in FIG. 12.

Expression loss after four SC doses (FIG. 8) appears to be T-cell dependent (FIG. 11). The higher response observed for anti-PEG IgM in BALB/c wild-type compared to BALB/c nude mice suggests that T cells have a role (FIG. 9). T cell cytokine production may lead to increased anti-PEG IgM in wild-type (as compared to nude) BALB/c mice. However, the small changes in the anti-EPO antibodies alone do not explain the differences in protein expression (FIG. 10). The results demonstrate that a combination of immune cells, including T cells, is involved in regulating protein expression levels and loss of protein expression.

Example 4: Repeat Dose SC (Rotation of Site of Injection)

Female CD1 mice (n=8 per group) were administered different formulations subcutaneously. Blood was sampled before the first dose (baseline) and one and six hours after each dose. The one hour samples were used to measure mRNA bDNA and the six hours samples were assayed for huEPO, IP10, and IL-6. Ninety-six hours after the second and fourth doses, samples were drawn for serum to measure PEG IgM, and 24 hours after the sixth dose, blood was drawn, and spleens and injection sites were saved.

Figure 13:
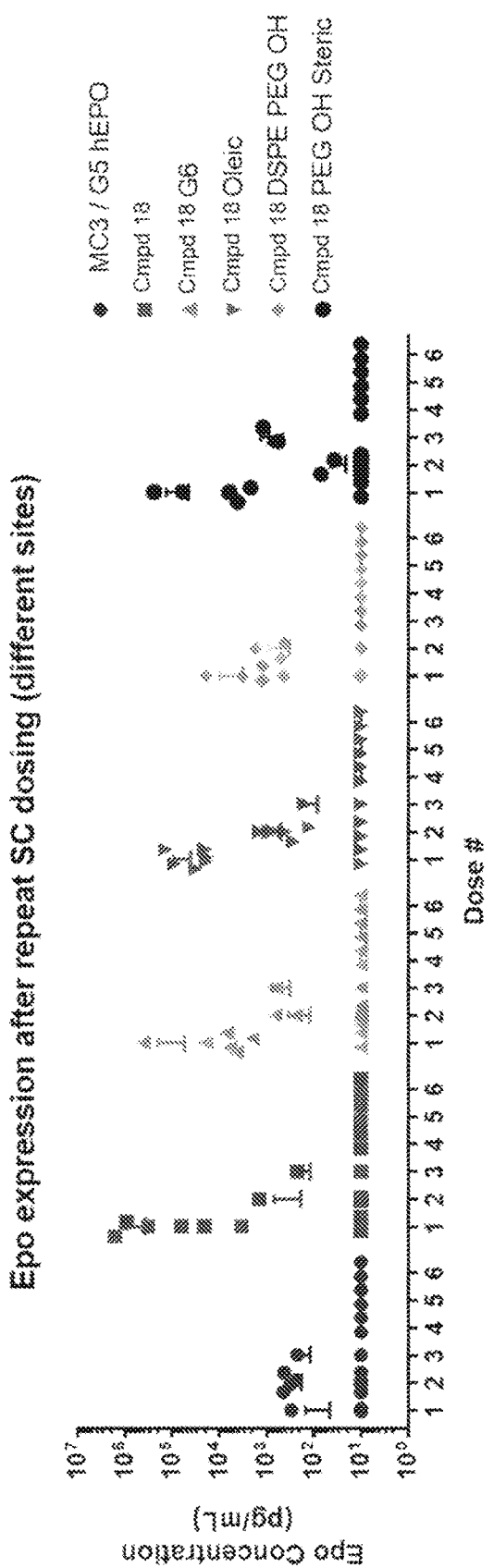
FIG. 13 shows EPO expression following repeat dosing at different sites using the formulations indicated.
Figure 14:
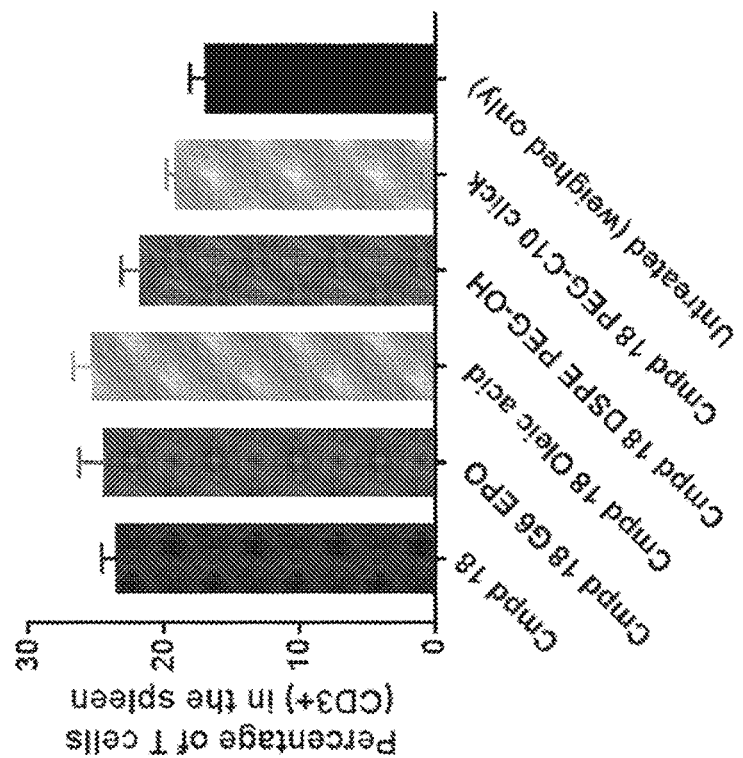
FIG. 14 shows T cell frequencies following repeat dosing at different sites using the formulations indicated.
Figure 14:
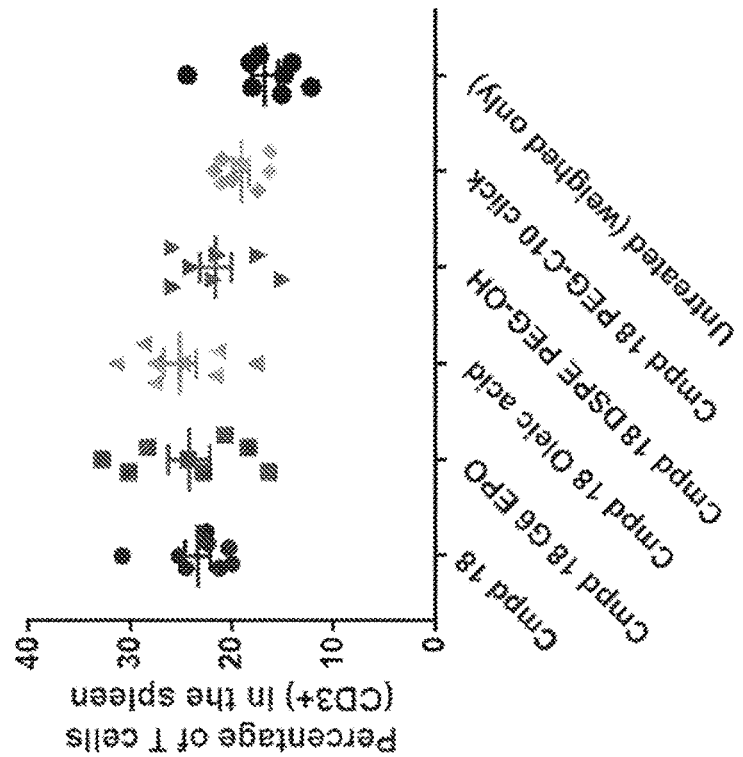
Figure 15:
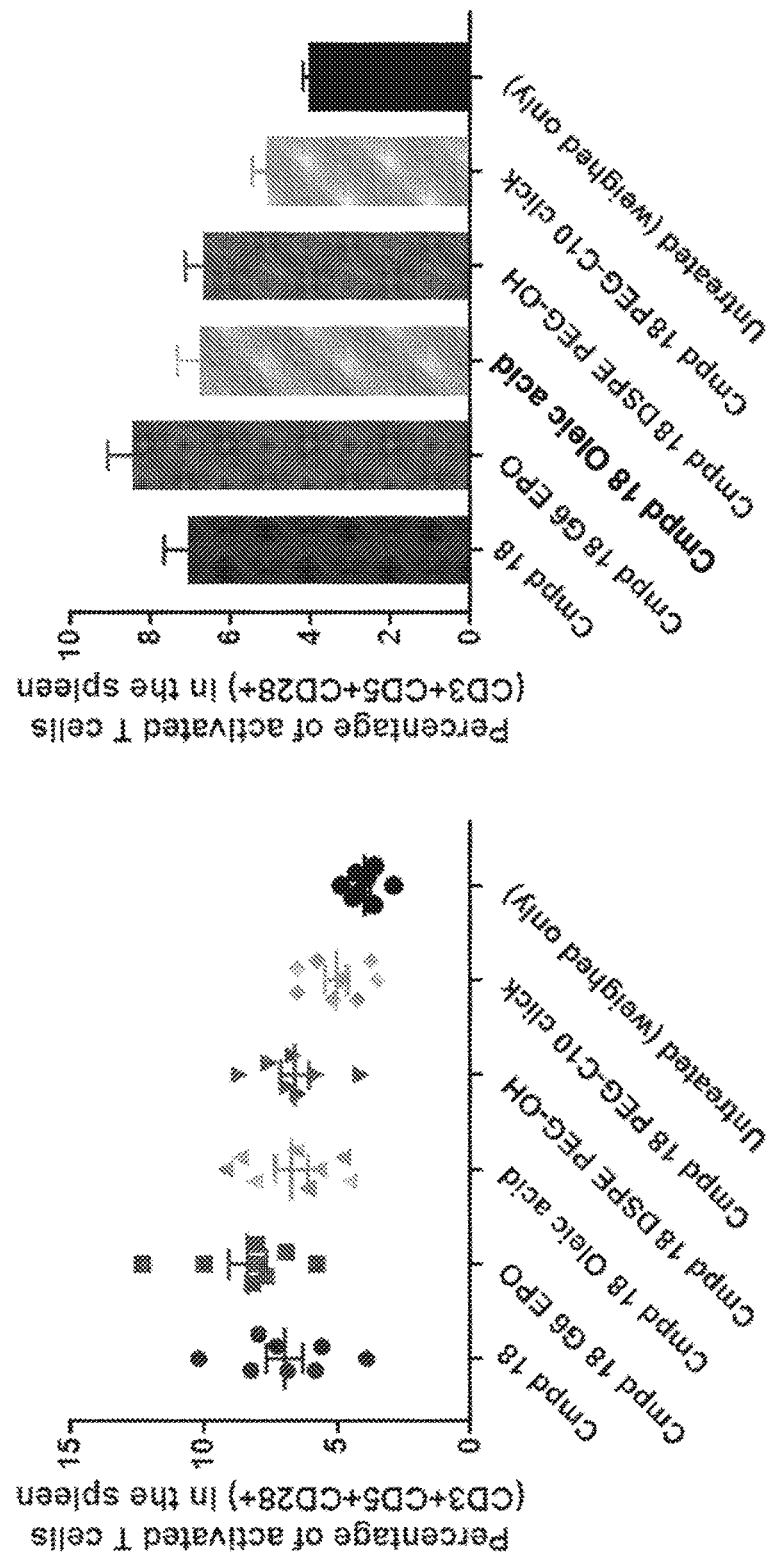
FIG. 15 shows activated T cell frequencies following repeat dosing at different sites using the formulations indicated.

As shown in FIG. 13, the results are consistent with previous data, showing a drop in protein expression with each dose. FIGS. 14 and 15 show T cell frequencies and activated T cell frequencies, respectively.

Example 5. IV Dosing Prior to SC Dosing Maintains Expression

Mice were pre-dosed IV for 6 weeks (at 3 dose levels) with LNP comprising mRNA encoding hEpo prior to 6 SC doses. As shown supra, IV predosing enables sustained expression upon subsequent SC dosing. As shown in FIG. 14, SC-only dosed mice show reduced Epo expression after only 4 SC doses, whereas IV+SC mice showed sustained expression.

Consistent with the expression data, there is minimal ADA in the IV predosed animals, while SC-only animals show a spike in anti-Epo antibody levels after 5 doses. (FIG. 15). Expression in SC-only animals dropped around day 63, which coincides with the increase in anti-Epo antibody levels.

Example 6: Repeat Dose IV/SC

In this study, the immune effects of repeat intravenous (IV) dosing followed by subcutaneous (SC) administration were examined. Female CD1 mice (n=5 per group) were given six intravenous doses of hEPO ($m^1\psi$) in Cmpd18 lipid nanoparticle formulations for six weeks (1 dose per week; the "predosing regimen"). Three different concentrations (0.50 mg/kg, 0.10 mg/kg, and 0.02 mg/kg) were tested. The three groups were then given six subcutaneous doses of hEPO ($m^1\psi$) in Cmpd18 lipid nanoparticle formulations for six weeks (1 dose per week; 0.50 mg/kg). An additional group did not receive the predosing regimen and only received the six subcutaneous doses (1 per week; 0.50 mg/kg).

Figure 16:
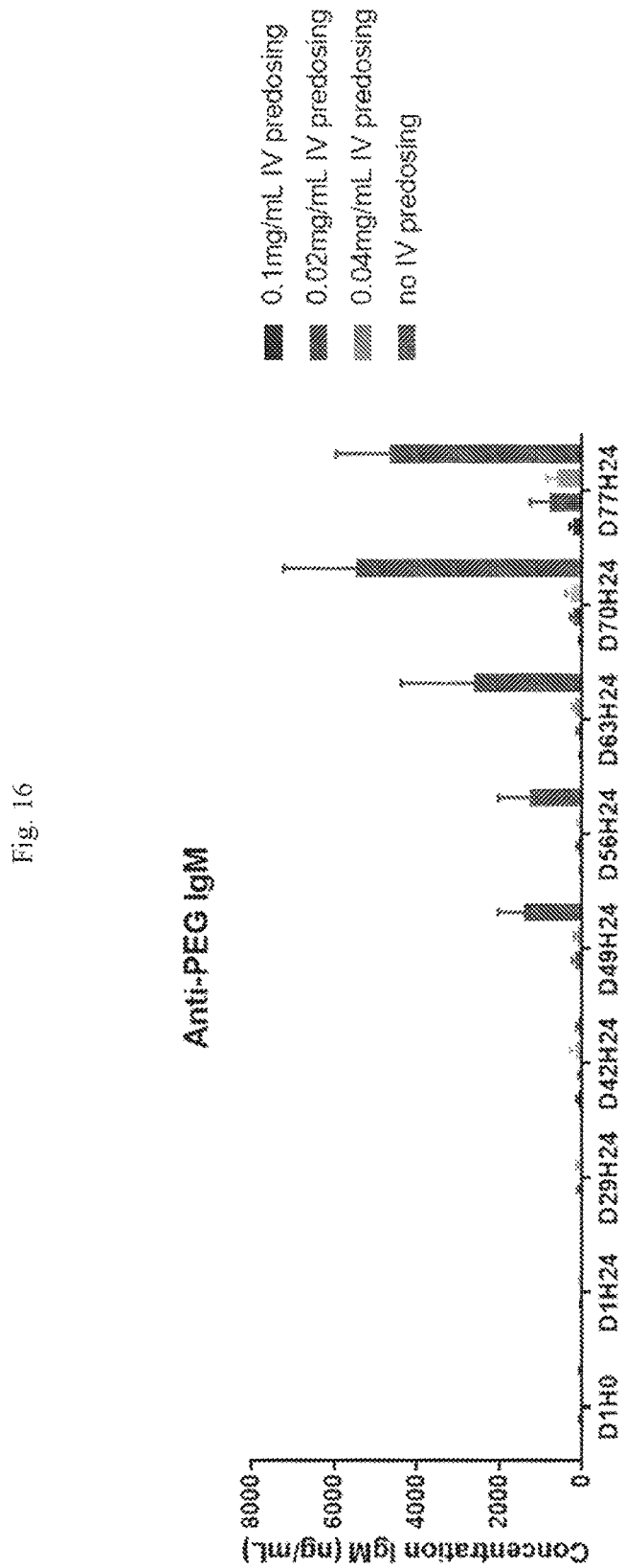
FIG. 16 shows anti-PEG IgM concentrations following administration of six repeated IV doses of an LNP formulation (1/week; predosing) followed by six repeated subcutaneous doses of the LNP formulation (1/week) at the concentrations indicated. Samples after baseline were taken 24 hours after dosing (e.g., D1H24 represents the sample taken 24 hours after the Day 1 dose).
Figure 17:
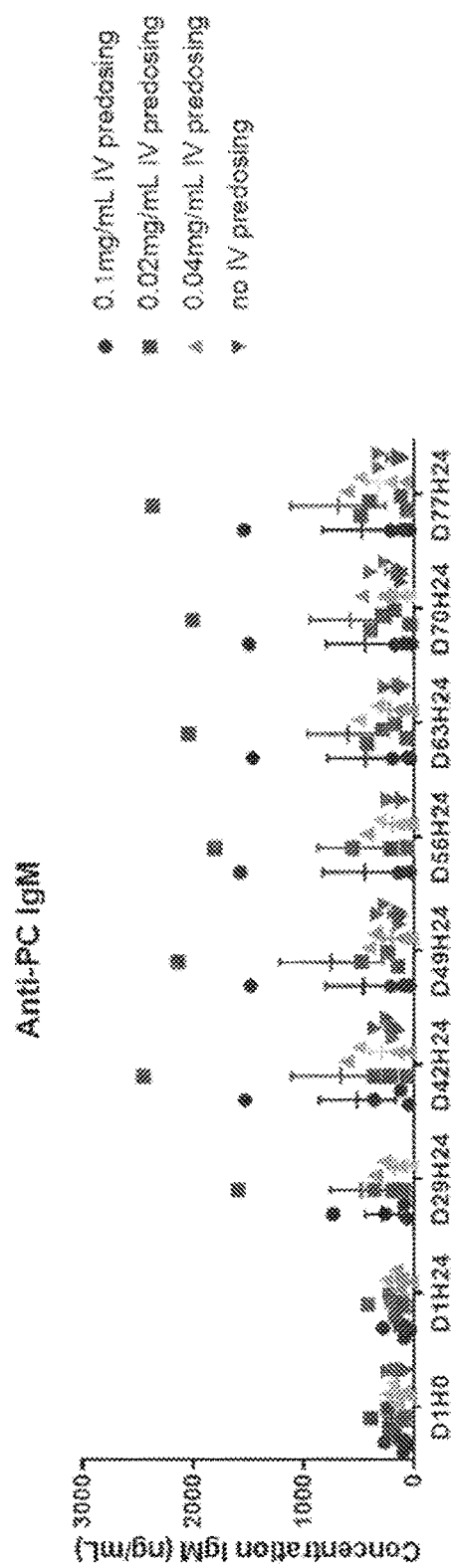
FIG. 17 shows anti-PC IgM concentrations following administration of six repeated IV doses of an LNP formulation (1/week; predosing) followed by six repeated subcutaneous doses of the LNP formulation (1/week) at the concentrations indicated.

Blood samples were taken just prior to the first IV dose to establish a baseline level of IgM. After the first sample, blood samples were taken 24 hours after each subsequent dose, and the anti-PEG IgM and anti-PC IgM were measured. The results are shown in FIGS. 16 and 17. As shown in FIG. 16, a significant increase in anti-PEG IgM was observed in Group 4, the group that did not receive the predosing regimen at both the Day 70 and Day 77 24-hour time points. No significant differences were observed at earlier time points based on a 2-way ANOVA.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. Each possibility represents a separate embodiment of the present invention.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for sequentially delivering lipid nanoparticles (LNPs) and an mRNA encoding a protein incorporated therein, to a subject to produce therapeutically effective amounts of the protein, the method comprising:
administering a first dose of LNPs to the subject intravenously to produce a therapeutically effective amount of the protein, and
subcutaneously administering at least a second dose and a third dose of LNPs to the subject, wherein the third dose is administered within 2 to 3 weeks of the second or a prior dose, wherein the subject does not have an immune response that promotes accelerated blood clearance (ABC) and/or anti-drug antibody (ADA) to the second and third doses of LNPs and wherein the subject receives an effective amount of the mRNA for treating a disease, wherein the subcutaneous doses are administered within three weeks of one another and wherein the LNPs comprise a molar ratio of about 20-60% ionizable cationic lipid, 0.5-25% neutral lipid, 25-55% sterol, and 0.5-15% PEG-lipid and wherein the ionizable cationic lipid comprises a compound of Formula (I):

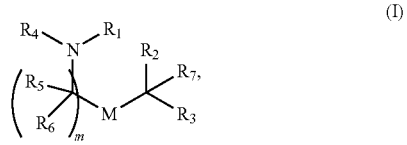

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a carbocycle, heterocycle, —OR, —$O(CH_2)_n$N$(R)_2$, —C(O)OR, —OC(O)R, —$CX_3$, —$CX_2$H, —$CXH_2$, —CN, —$N(R)_2$, —C(O)N$(R)_2$, —N(R)C(O)R, —N(R)S(O)$_2$R, —N(R)C(O)N$(R)_2$, —N(R)C(S)N$(R)_2$, —N(R)$R_8$, —$O(CH_2)_n$OR, —N(R)C($=NR_9$)N$(R)_2$, —N(R)C($=CHR_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C($=NR_9$)N$(R)_2$, —N(OR)C($=CHR_9$)N$(R)_2$, —C($=NR_9$)N$(R)_2$, —C($=NR_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

2. The method of claim 1, wherein an additional dose is administered intravenously before the second and third doses of LNPs are administered subcutaneously.

3. The method of claim 1, wherein the subcutaneous doses are administered within two weeks of one another.

4. The method of claim 1, wherein the protein is a secreted protein, an intracellular protein, or a transmembrane protein.

5. The method of claim 1, wherein the immune response involves activation of T cells and wherein the T cells are not activated in the subject to a level which promotes ADA.

6. The method of claim 1, wherein the LNPs comprise oleic acid or an oleic acid analog.

7. The method of claim 1, wherein the LNPs are administered to the subject at multiple doses.

8. The method of claim 1, wherein the mRNA comprises at least one microRNA binding site for a microRNA expressed in immune cells.

9. The method of claim 8, wherein the mRNA having at least one microRNA binding site causes unwanted immune cell activation to be reduced or inhibited in the subject.

10. The method of claim 8, wherein the mRNA is chemically modified mRNA.

11. The method of claim 10, wherein the mRNA comprises pseudouridine (ψ), pseudouridine (ψ) and 5-methyl-cytidine (m5C), 1-methyl-pseudouridine (m1ψ), 1-methyl-pseudouridine (m1ψ) and 5-methyl-cytidine (m5C), 2-thiouridine (s2U), 2-thiouridine and 5-methyl-cytidine (m5C), 5-methoxy-uridine (mo5U), 5-methoxy-uridine (mo5U) and 5-methyl-cytidine (m5C), 2'-O-methyl uridine, 2'-O-methyl uridine and 5-methyl-cytidine (m5C), N6-methyl-adenosine (m6A), N6-methyl-adenosine (m6A) and 5-methyl-cytidine (m5C), pseudouridine (ψ), N1-methylpseudouridine (m1ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine, or combinations thereof.

12. A method in a subject of increasing a therapeutic index of a therapeutic regimen involving lipid nanoparticle (LNP)-mediated mRNA drug delivery, the method comprising:
administering LNPs comprising an mRNA encoding a protein to the subject in multiple doses, each dose sequentially administered within three weeks of another dose,
wherein a first dose is administered intravenously and subsequent doses are administered via non-intravenous routes,
wherein the LNPs do not induce an immune response associated with reduced protein expression, such that an increased therapeutic index of the therapeutic regimen is achieved relative to administration of an LNP comprising an mRNA encoding a protein that induces an immune response associated with reduced protein expression, and wherein the LNP comprises a molar ratio of about 20-60% ionizable cationic lipid, 0.5-25% neutral lipid, 25-55% sterol, and 0.5-15% PEG-lipid and wherein the ionizable cationic lipid comprises a compound of Formula (I):

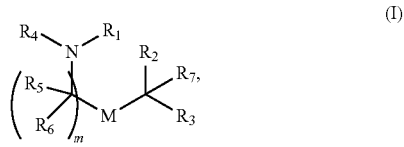

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

13. A method comprising
(i) administering a first dose of an LNP and an mRNA encoding a therapeutic or intracellular protein incorporated therein to a subject intravenously (IV),
(ii) administering a second or subsequent dose of the LNP to the subject via a non-IV route, (optionally, the second or subsequent dose is administered within 2 weeks of the first or prior dose), and
(iii) repeating step (ii) one or more times,
wherein the LNP comprises a molar ratio of about 20-60% ionizable cationic lipid, 0.5-25% neutral lipid, 25-55% sterol, and 0.5-15% PEG-lipid and wherein the ionizable cationic lipid comprises a compound of Formula (I):

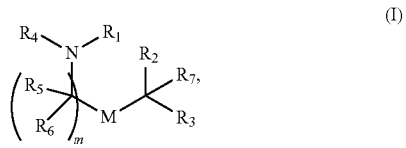

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

14. A method for delivering an agent to a subject comprising:
(i) administering a first dose of an agent comprising an LNP and an mRNA encoding a therapeutic protein or intracellular protein incorporated therein to a subject intravenously, (ii) administering a second or subsequent dose of the agent to the subject via a non-intravenous route, wherein the second or subsequent dose is administered within 2 to 3 weeks of the first or prior dose, and (iii) repeating step (ii) one or more times, Wherein the half-life of the agent after the second or subsequent dose is at least 50%, 60%, 70%, 80%, 85%, 90%, 95% or more of the half-life of the agent after the first dose and wherein the LNP comprises a molar ratio of about 20-60% ionizable cationic lipid, 0.5-25% neutral lipid, 25-55% sterol, and 0.5-15% PEG-lipid and wherein the ionizable cationic lipid comprises a compound of Formula (I):

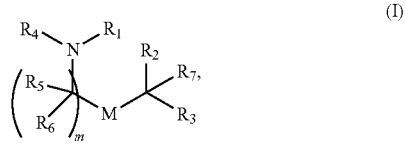

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

15. A method for delivering an agent to a subject comprising:

(i) administering a first dose of an agent comprising an LNP and an mRNA encoding a therapeutic protein or intracellular protein incorporated therein to a subject intravenously, (ii) administering a second or subsequent dose of the agent to the subject via a non-intravenous route, wherein the second or subsequent dose is administered within 2 to 3 weeks of the first or prior dose, and (iii) repeating step (ii) one or more times, wherein the activity or blood concentration of the agent after the second or subsequent dose is at least 50%, 60%, 70%, 80%, 85%, 90%, 95% or more of the activity or blood concentration of the agent after the first dose, and wherein the LNP comprises a molar ratio of about 20-60% ionizable cationic lipid, 0.5-25% neutral lipid, 25-55% sterol, and 0.5-15% PEG-lipid and wherein the ionizable cationic lipid comprises a compound of Formula (I):

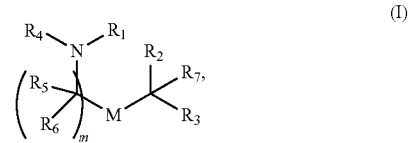

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH (OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13.

16. A pharmaceutical composition of a subcutaneous formulation comprising a lipid nanoparticle (LNP) comprising an mRNA encoding a protein incorporated therein, wherein the mRNA comprises at least one miR-142 binding site and at least one miR-126 binding site, wherein the LNP and/or microRNA binding sites increases or increase a therapeutic index greater than 10% relative to a chemically modified mRNA encoding a protein alone, and wherein the LNP comprises a molar ratio of about 20-60% ionizable cationic lipid, 0.5-25% neutral lipid, 25-55% sterol, and 0.5-15% PEG-lipid and wherein the ionizable cationic lipid comprises a compound of Formula (I):

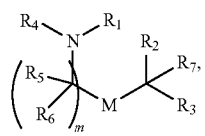

(I)

or a salt or isomer thereof, wherein:

R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$CHQR, —CHQR, —CQ(R)$_2$, and unsubstituted C$_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13.

\* \* \* \* \*

UNITED STATES PATENT AND TRADEMARK OFFICE
CERTIFICATE OF CORRECTION

| | |
|---|---|
| PATENT NO. | : 11,905,525 B2 |
| APPLICATION NO. | : 16/603111 |
| DATED | : February 20, 2024 |
| INVENTOR(S) | : Luis Brito et al. |

It is certified that error appears in the above-identified patent and that said Letters Patent is hereby corrected as shown below:

On the Title Page

In item (54) and In the Specification, Column 1, Lines 1-5, the title:
"REDUCTION OF ELIMINATION OF IMMUNE RESPONSES TO NON- INTRAVENOUS, E.G., SUBCUTANEOUSLY ADMINISTERED THERAPEUTIC PROTEINS"

Should be replaced with:
-- REDUCTION OR ELIMINATION OF IMMUNE RESPONSES TO NON-INTRAVENOUS, E.G., SUBCUTANEOUSLY ADMINISTERED THERAPEUTIC PROTEINS --

Signed and Sealed this
Ninth Day of April, 2024

Katherine Kelly Vidal
*Director of the United States Patent and Trademark Office*

```
                           SEQUENCE LISTING

<160> NUMBER OF SEQ ID NOS: 74

<210> SEQ ID NO 1
<211> LENGTH: 768
<212> TYPE: RNA
<213> ORGANISM: Artificial Sequence
<220> FEATURE:
<223> OTHER INFORMATION: Synthetic Polynucleotide

<400> SEQUENCE: 1
gggaaauaag agagaaaaga agaguaagaa gaaauauaag agccaccaug ggagugcacg      60 aguguccogc gugguugugg uugcugcugu cgcucuugag ccucccacug ggacugccug     120
ugcugggggc accacccaga uugaucugcg acucacgggu acuugagagg uaccuucuug     180
aagccaaaga agccgaaaac aucacaaccg gaugcgccga gcacugcucc cucaaugaga     240
acauuacugu accggauaca aaggucaauu ucuaugcaug gaagagaaug gaaguaggac     300
agcaggccgu cgaagugugg caggggcucg cgcuuuuguc ggaggcggug uugcggggguc    360 aggcccuccu cgucaacuca ucacagccgu gggagcccu ccaacuucau gucgauaaag      420
cggugucggg gcuccgcagc uugacgacgu ugcuucgggc ucgggcgca caaaggagg      480 cuauuucgcc gccugacgcg gccuccgcgg cacccccuccg aacgaucacc gcggacacgu    540
uuaggaagcu uuuuagagug uacagcaauu uccuccgcgg aaagcugaaa uuguauacug    600
gugaagcgug uaggacaggg gaucgcugau aauaggcugg agccucggug gccaugcuuc    660 uugcccuug ggccucccc cagcccucc uccccuuccu gcacccguac ccccuccaua      720
aaguaggaaa cacuacagug gucuuugaau aaagucugag ugggcggc                 768

<210> SEQ ID NO 2
<211> LENGTH: 133
<212> TYPE: RNA
<213> ORGANISM: Artificial Sequence
<220> FEATURE:
<223> OTHER INFORMATION: Synthetic Polynucleotide

<400> SEQUENCE: 2
gcuggagccu cgguggccau gcuucuugcc ccuugggccu ccccccagcc ccuccuccc      60 uuccugcacc cguaccccu ccauaaagua ggaaacacua caggggucuu ugaauaaagu    120 cugaguggc ggc                                                       133

<210> SEQ ID NO 3
<211> LENGTH: 23
<212> TYPE: RNA
<213> ORGANISM: Artificial Sequence
<220> FEATURE:
```

<223> OTHER INFORMATION: Synthetic Polynucleotide

<400> SEQUENCE: 3
uccauaaagu aggaaacacu aca                                           23

<210> SEQ ID NO 4
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 4

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 5
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 5
ggaagcggag ctactaactt cagcctgctg aagcaggctg agacgtgga ggagaaccct    60 ggacct                                                              66

<210> SEQ ID NO 6
<211> LENGTH: 108
<212> TYPE: DNA
<213> ORGANISM: Artificial Sequence
<220> FEATURE:
<223> OTHER INFORMATION: Synthetic Polynucleotide

<400> SEQUENCE: 6
tccggactca gatccgggga tctcaaaatt gtcgctcctg tcaaacaaac tcttaacttt    60
gatttactca aactggctgg ggatgtagaa agcaatccag gtccactc                108

<210> SEQ ID NO 7
<211> LENGTH: 745
<212> TYPE: RNA
<213> ORGANISM: Artificial Sequence
<220> FEATURE:
<223> OTHER INFORMATION: Synthetic Polynucleotide

<400> SEQUENCE: 7 gggaauaag agagaaaaga agaguaagaa gaaauauaag agccaccaug ggagugcacg    60
agugucccgc gugguugugg uugcugcugu cgcucuugag ccucccacug ggacugccug   120 ugcuggggc accacccaga uugaucgcg acucacgggu acuugagagg uaccuucuug    180
aagccaaaga agccgaaaac aucacaaccg gaugcgccga gcacugcucc cucaaugaga   240
acauuacugu accggauaca aaggucaauu cuaugcaug gaagagaaug gaaguaggac    300
agcaggccgu cgaagugugg caggggcucg cgcuuuuguc ggaggcggug uugcggggguc   360 aggcccuccu cgucaacuca ucacagccgu gggagcccu ccaacuucau gucgauaaag    420
cggugucggg gcccgcagc uugacgacgu ugcuucgggc ucugggcgca caaaaggagg    480
cuauuucgcc gccugacgcg gccuccgcgg cacccuccg aacgaucacc gcggacacgu    540
uuaggaagcu uuuuagagug uacagcaauu cccuccgcgg aaagcugaaa uuguauacug    600

| | |
|---|---|
| gugaagcgug uaggacaggg gaucgcugau aauaggcugg agccucggug gccaugcuuc | 660 |
| uugccccuug ggccucccc cagccccucc uccccuuccu gcaccgcuac ccccgugguc | 720 |
| uuugaauaaa gucugagugg gcggc | 745 |

```
<210> SEQ ID NO 8
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 8
```

| | |
|---|---|
| uguaguguuu ccuacuuuau gga | 23 |

```
<210> SEQ ID NO 9
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 9
```

| | |
|---|---|
| cauaaaguag aaagcacuac u | 21 |

```
<210> SEQ ID NO 10
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 10
```

| | |
|---|---|
| ccucugaaau ucaguucuuc ag | 22 |

```
<210> SEQ ID NO 11
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 11
```

| | |
|---|---|
| ugagaacuga auccauggg uu | 22 |

```
<210> SEQ ID NO 12
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 12
```

| | |
|---|---|
| cuccuacaua uuagcauuaa ca | 22 |

```
<210> SEQ ID NO 13
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 13
```

| | |
|---|---|
| uuaaugcuaa ucgugauagg ggu | 23 |

<210> SEQ ID NO 14
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 14
ucguaccgug aguaauaaug cg                                              22

<210> SEQ ID NO 15
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 15
cauuauuacu uuugguacgc g                                               21

<210> SEQ ID NO 16
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 16
ccaguauuaa cugugcugcu ga                                              22

<210> SEQ ID NO 17
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 17
uagcagcacg uaaauauugg cg                                              22

<210> SEQ ID NO 18
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 18
caacaccagu cgaugggcug u                                               21

<210> SEQ ID NO 19
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 19
uagcuuauca gacugauguu ga                                              22

<210> SEQ ID NO 20
<211> LENGTH: 22
<212> TYPE: RNA
<213> ORGANISM: Artificial Sequence
<220> FEATURE:
<223> OTHER INFORMATION: Synthetic Polynucleotide

```
<400> SEQUENCE: 20
ugucaguuug ucaaauaccc ca                                              22

<210> SEQ ID NO 21
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 21
cguguauuug acaagcugag uu                                              22

<210> SEQ ID NO 22
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 22
uggcucaguu cagcaggaac ag                                              22

<210> SEQ ID NO 23
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 23
ugccuacuga gcugauauca gu                                              22

<210> SEQ ID NO 24
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 24
uucacagugg cuaaguuccg c                                               21

<210> SEQ ID NO 25
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 25
agggcuuagc ugcuugugag ca                                              22

<210> SEQ ID NO 26
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 26
cgcauuauua cucacgguac ga                                              22

<210> SEQ ID NO 27
```

```
<211> LENGTH: 141
<212> TYPE: RNA
<213> ORGANISM: Artificial Sequence
<220> FEATURE:
<223> OTHER INFORMATION: Synthetic Polynucleotide

<400> SEQUENCE: 27
ugauaauagg cuggagccuc gguggccaug cuucuugccc cuugggccuc ccccagccc      60 cuccucccu uccugcaccc guaccccccg cauuauuacu cacgguacga guggucuuug    120
aauaaagucu gagugggcgg c                                             141

<210> SEQ ID NO 28
<211> LENGTH: 767
<212> TYPE: RNA
<213> ORGANISM: Artificial Sequence
<220> FEATURE:
<223> OTHER INFORMATION: Synthetic Polynucleotide

<400> SEQUENCE: 28 gggaauaag agagaaaaga agaguaagaa gaaauauaag agccaccaug ggagugcacg     60 aguguccgc gugguugugg uugcugcugu cgcucuugag ccucccacug ggacugccug    120
ugcugggggc accacccaga uugaucugcg acucacgggu acuugagagg uaccuucuug   180
aagccaaaga agccgaaaac aucacaaccg gaugcgccga gcacugcucc cucaaugaga   240
acauuacugu accggauaca aaggucaauu ucuaugcaug gaagagaaug gaaguaggac   300
agcaggccgu cgaaguguug cagggggcucg cgcuuuuguc ggaggcgggug uugcggggguc  360 aggcccuccu cgucaacuca ucacagccgu gggagccccu ccaacuucau gucgauaaag   420
cgugucgggg gcuccgcagc uugacgacgu ugcuucgggc ucugggcgca caaaaggagg   480
cuauuucgcc gccugacgcg gccuccgcgg cacccccucg aacgaucacc gcggacacgu   540
uuaggaagcu uuuuagagug uacagcaauu uccuccgcgg aaagcugaaa uuguauacug   600
gugaagcgug uaggacaggg gaucgcugau aauaggcugg agccucgggu gccaugcuuc   660
uugccccuug ggccucccc cagccccucc uccccuuccu gcacccguac ccccgcauu     720 auuacucacg guacgagugg ucuuugaaua aagucugagu gggcggc                 767

<210> SEQ ID NO 29
<211> LENGTH: 790
<212> TYPE: RNA
<213> ORGANISM: Artificial Sequence
<220> FEATURE:
<223> OTHER INFORMATION: Synthetic Polynucleotide

<400> SEQUENCE: 29 gggaauaag agagaaaaga agaguaagaa gaaauauaag agccaccaug ggagugcacg     60 aguguccgc gugguugugg uugcugcugu cgcucuugag ccucccacug ggacugccug    120
ugcugggggc accacccaga uugaucugcg acucacgggu acuugagagg uaccuucuug   180
aagccaaaga agccgaaaac aucacaaccg gaugcgccga gcacugcucc cucaaugaga   240
acauuacugu accggauaca aaggucaauu ucuaugcaug gaagagaaug gaaguaggac   300
agcaggccgu cgaaguguug cagggggcucg cgcuuuuguc ggaggcgggug uugcggggguc  360 aggcccuccu cgucaacuca ucacagccgu gggagccccu ccaacuucau gucgauaaag   420
cgugucgggg gcuccgcagc uugacgacgu ugcuucgggc ucugggcgca caaaaggagg   480
cuauuucgcc gccugacgcg gccuccgcgg cacccccucg aacgaucacc gcggacacgu   540
uuaggaagcu uuuuagagug uacagcaauu uccuccgcgg aaagcugaaa uuguauacug   600
```

```
gugaagcgug uaggacaggg gaucgcugau aauaguccau aaaguaggaa acacuacagc    660
uggagccucg guggccaugc uucuugcccc uugggccucc ccccagcccc uccuccccuu    720
ccugcacccg uacccccgc auuauuacuc acgguacgag uggucuuuga auaaagucug    780
agugggcggc                                                          790

<210> SEQ ID NO 30
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 30
tgataatagg ctggagcctc ggtggccatg cttcttgccc cttgggcctc ccccagccc     60 ctcctcccct tcctgcaccc gtaccccgt ggtctttgaa taaagtctga gtgggcggc    119

<210> SEQ ID NO 31
<211> LENGTH: 142
<212> TYPE: DNA
<213> ORGANISM: Artificial Sequence
<220> FEATURE:
<223> OTHER INFORMATION: Synthetic Polynucleotide

<400> SEQUENCE: 31
tgataatagg ctggagcctc ggtggccatg cttcttgccc cttgggcctc ccccagccc     60 ctcctcccct tcctgcaccc gtaccccctc cataaagtag gaaacactac agtggtcttt   120
gaataaagtc tgagtgggcg gc                                           142

<210> SEQ ID NO 32
<211> LENGTH: 141
<212> TYPE: DNA
<213> ORGANISM: Artificial Sequence
<220> FEATURE:
<223> OTHER INFORMATION: Synthetic Polynucleotide

<400> SEQUENCE: 32
tgataatagg ctggagcctc ggtggccatg cttcttgccc cttgggcctc ccccagccc     60 ctcctcccct tcctgcaccc gtaccccccg cattattact cacggtacga gtggtctttg   120
aataaagtct gagtgggcgg c                                            141

<210> SEQ ID NO 33
<211> LENGTH: 164
<212> TYPE: DNA
<213> ORGANISM: Artificial Sequence
<220> FEATURE:
<223> OTHER INFORMATION: Synthetic Polynucleotide

<400> SEQUENCE: 33
tgataatagt ccataaagta ggaaacacta cagctggagc ctcggtggcc atgcttcttg    60
ccccttgggc ctccccccag ccctcctcc ccttcctgca cccgtacccc ccgcattatt   120
actcacggta cgagtggtct ttgaataaag tctgagtggg cggc                   164

<210> SEQ ID NO 34
<211> LENGTH: 23
<212> TYPE: RNA
<213> ORGANISM: Artificial Sequence
<220> FEATURE:
<223> OTHER INFORMATION: Synthetic Polynucleotide
```

```
<400> SEQUENCE: 34
uuaaugcuaa uugugauagg ggu                                             23

<210> SEQ ID NO 35
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 35
acccctatca caattagcat taa                                             23

<210> SEQ ID NO 36
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 36
tgataatagg ctggagcctc ggtggccatg cttcttgccc cttgggcctc ccccagccc      60 ctcctcccct tcctgcaccc gtaccccgt ggtctttgaa taaagtctga gtgggcggc     119

<210> SEQ ID NO 37
<211> LENGTH: 142
<212> TYPE: DNA
<213> ORGANISM: Artificial Sequence
<220> FEATURE:
<223> OTHER INFORMATION: Synthetic Polynucleotide

<400> SEQUENCE: 37
ugauaauagg cuggagccuc gguggccaug cuucuugccc cuugggccuc ccccagccc      60 cuccucccu uccugcaccc guaccccuc cauaaaguag gaaacacuac aguggucuuu     120
gaauaaaguc ugaguggggcg gc                                            142

<210> SEQ ID NO 38
<211> LENGTH: 188
<212> TYPE: DNA
<213> ORGANISM: Artificial Sequence
<220> FEATURE:
<223> OTHER INFORMATION: Synthetic Polynucleotide

<400> SEQUENCE: 38
tgataatagt ccataaagta ggaaacacta cagctggagc tcggtggcc atgcttcttg      60 cccttgggc ctccataaag taggaaacac tacatccccc cagcccctcc tcccttcct     120 gcacccgtac cccctccata agtaggaaa cactacagtg gtctttgaat aaagtctgag    180
tgggcggc                                                            188

<210> SEQ ID NO 39
<211> LENGTH: 140
<212> TYPE: DNA
<213> ORGANISM: Artificial Sequence
<220> FEATURE:
<223> OTHER INFORMATION: Synthetic Polynucleotide

<400> SEQUENCE: 39
tgataatagg ctggagcctc ggtggccatg cttcttgccc cttgggcctc ccccagccc      60 ctcctcccct tcctgcaccc gtaccccag tagtgctttc tactttatgg tggtctttga    120
ataaagtctg agtgggcggc                                               140
```

<210> SEQ ID NO 40
<211> LENGTH: 182
<212> TYPE: DNA
<213> ORGANISM: Artificial Sequence
<220> FEATURE:
<223> OTHER INFORMATION: Synthetic Polynucleotide

<400> SEQUENCE: 40
tgataataga gtagtgcttt ctactttatg gctggagcct cggtggccat gcttcttgcc      60
ccttgggcca gtagtgcttt ctactttatg tcccccagc ccctcctccc cttcctgcac     120
ccgtaccccc agtagtgctt tctactttat ggtggtcttt gaataaagtc tgagtgggcg     180
gc                                                                    182

<210> SEQ ID NO 41
<211> LENGTH: 184
<212> TYPE: DNA
<213> ORGANISM: Artificial Sequence
<220> FEATURE:
<223> OTHER INFORMATION: Synthetic Polynucleotide

<400> SEQUENCE: 41
tgataataga gtagtgcttt ctactttatg gctggagcct cggtggccat gcttcttgcc      60
ccttgggcct ccataaagta ggaaacacta catcccccca gccctcctc cccttcctgc     120 acccgtaccc ccagtagtgc tttctacttt atggtggtct ttgaataaag tctgagtggg     180
cggc                                                                  184

<210> SEQ ID NO 42
<211> LENGTH: 142
<212> TYPE: DNA
<213> ORGANISM: Artificial Sequence
<220> FEATURE:
<223> OTHER INFORMATION: Synthetic Polynucleotide

<400> SEQUENCE: 42
tgataatagg ctggagcctc ggtggccatg cttcttgccc cttgggcctc ccccagccc      60 ctcctcccct tcctgcaccc gtaccccac ccctatcaca attagcatta agtggtcttt     120
gaataaagtc tgagtgggcg gc                                              142

<210> SEQ ID NO 43
<211> LENGTH: 188
<212> TYPE: DNA
<213> ORGANISM: Artificial Sequence
<220> FEATURE:
<223> OTHER INFORMATION: Synthetic Polynucleotide

<400> SEQUENCE: 43
tgataataga ccctatcac aattagcatt aagctggagc tcggtggcc atgcttcttg       60 ccccttgggc caccccctatc acaattagca ttaatccccc cagcccctcc tcccttcct    120 gcaccCgtac ccccaccCct atcacaatta gcattaagtg gtctttgaat aaagtctgag    180
tgggcggc                                                              188

<210> SEQ ID NO 44
<211> LENGTH: 188
<212> TYPE: DNA
<213> ORGANISM: Artificial Sequence
<220> FEATURE:
<223> OTHER INFORMATION: Synthetic Polynucleotide

```
<400> SEQUENCE: 44
tgataataga cccctatcac aattagcatt aagctggagc ctcggtggcc atgcttcttg      60 cccttgggc ctccataaag taggaaacac tacatccccc cagcccctcc tccccttcct     120
gcacccgtac ccccaccccct atcacaatta gcattaagtg gtctttgaat aaagtctgag    180
tgggcggc                                                               188

<210> SEQ ID NO 45
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 45
uauuuagugu gauaauggcg uu                                               22

<210> SEQ ID NO 46
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 46
caaacaccau ugucacacuc ca                                               22

<210> SEQ ID NO 47
<211> LENGTH: 164
<212> TYPE: DNA
<213> ORGANISM: Artificial Sequence
<220> FEATURE:
<223> OTHER INFORMATION: Synthetic Polynucleotide

<400> SEQUENCE: 47
tgataatagt ccataaagta ggaaacacta cagctggagc ctcggtggcc atgcttcttg      60 cccttgggc ccaaacacca ttgtcacact ccatccccccc agcccctcct ccccttcctg    120
cacccgtacc cccgtggtct ttgaataaag tctgagtggg cggc                     164

<210> SEQ ID NO 48
<211> LENGTH: 142
<212> TYPE: DNA
<213> ORGANISM: Artificial Sequence
<220> FEATURE:
<223> OTHER INFORMATION: Synthetic Polynucleotide

<400> SEQUENCE: 48
tgataatagt ccataaagta ggaaacacta cagctggagc ctcggtggcc atgcttcttg      60 cccttgggc ctcccccag ccctcctcc ccttcctgca cccgtacccc cgtggtcttt       120
gaataaagtc tgagtgggcg gc                                              142

<210> SEQ ID NO 49
<211> LENGTH: 142
<212> TYPE: DNA
<213> ORGANISM: Artificial Sequence
<220> FEATURE:
<223> OTHER INFORMATION: Synthetic Polynucleotide

<400> SEQUENCE: 49
tgataatagg ctggagcctc ggtggctcca taaagtagga aacactacac atgcttcttg      60 cccttgggc ctcccccag ccctcctcc ccttcctgca cccgtacccc cgtggtcttt       120
```

```
gaataaagtc tgagtgggcg gc                                           142

<210> SEQ ID NO 50
<211> LENGTH: 142
<212> TYPE: DNA
<213> ORGANISM: Artificial Sequence
<220> FEATURE:
<223> OTHER INFORMATION: Synthetic Polynucleotide

<400> SEQUENCE: 50
tgataatagg ctggagcctc ggtggccatg cttcttgccc cttgggcctc cataaagtag    60
gaaacactac atcccccag cccctcctcc ccttcctgca cccgtacccc cgtggtcttt    120
gaataaagtc tgagtgggcg gc                                           142

<210> SEQ ID NO 51
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 51
aguagugcuu ucuacuuuau g                                             21

<210> SEQ ID NO 52
<211> LENGTH: 87
<212> TYPE: RNA
<213> ORGANISM: Artificial Sequence
<220> FEATURE:
<223> OTHER INFORMATION: Synthetic Polynucleotide

<400> SEQUENCE: 52
gacagugcag ucacccauaa aguagaaagc acuacuaaca gcacuggagg guguaguguu    60
uccuacuuua uggaugagug uacugug                                        87

<210> SEQ ID NO 53
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 53
gggaaataag agagaaaaga agagtaagaa gaaatataag agccacc                   47

<210> SEQ ID NO 54
<211> LENGTH: 185
<212> TYPE: DNA
<213> ORGANISM: Artificial Sequence
<220> FEATURE:
<223> OTHER INFORMATION: Synthetic Polynucleotide

<400> SEQUENCE: 54
tgataatagc aaacaccatt gtcacactcc agctggagcc tcggtggcca tgcttcttgc    60
cccttgggcc caaacaccat tgtcacactc catcccccca gccctcctc ccttcctgc     120 acccgtaccc cccaaacacc attgtcacac tccagtggtc tttgaataaa gtctgagtgg   180
gcggc                                                              185

<210> SEQ ID NO 55
<211> LENGTH: 70
<212> TYPE: DNA
```

<213> ORGANISM: Artificial Sequence
<220> FEATURE:
<223> OTHER INFORMATION: Synthetic Polynucleotide

<400> SEQUENCE: 55
gggaaataag agtccataaa gtaggaaaca ctacaagaaa agaagagtaa gaagaaatat    60
aagagccacc                                                           70

<210> SEQ ID NO 56
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 56
gggaaataag agagaaaaga agagtaatcc ataaagtagg aaacactaca gaagaaatat    60
aagagccacc                                                           70

<210> SEQ ID NO 57
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 57
gggaaataag agagaaaaga agagtaagaa gaaatataat ccataaagta ggaaacacta    60
cagagccacc                                                           70

<210> SEQ ID NO 58
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 58
gggaaataag agcaaacacc attgtcacac tccaagaaaa gaagagtaag aagaaatata    60
agagccacc                                                            69

<210> SEQ ID NO 59
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 59
gggaaataag agagaaaaga agagtaacaa acaccattgt cacactccag aagaaatata    60
agagccacc                                                            69

<210> SEQ ID NO 60
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 60
gggaaataag agagaaaaga agagtaagaa gaaatataac aaacaccatt gtcacactcc    60
agagccacc                                                            69

```
<210> SEQ ID NO 61
<211> LENGTH: 164
<212> TYPE: RNA
<213> ORGANISM: Artificial Sequence
<220> FEATURE:
<223> OTHER INFORMATION: Synthetic Polynucleotide

<400> SEQUENCE: 61
ugauaauagu ccauaaagua ggaaacacua cagcuggagc cucgguggcc augcuucuug      60
ccccuugggc uccccccag ccccuccucc ccuuccugca cccguacccc ccgcauuauu     120
acucacggua cgaguggucu uugaauaaag ucgaguggg cggc                      164

<210> SEQ ID NO 62
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 62
accccuauca caauuagcau uaa                                             23

<210> SEQ ID NO 63
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 63
ugauaauagu ccauaaagua ggaaacacua cagcuggagc cucgguggcc augcuucuug      60
ccccuugggc cuccauaaag uaggaaacac uacauccccc cagccccucc ucccuuccu     120 gcacccguac ccccuccaua aaguaggaaa cacuacagug gucuuugaau aaagucugag    180
ugggcggc                                                             188

<210> SEQ ID NO 64
<211> LENGTH: 140
<212> TYPE: RNA
<213> ORGANISM: Artificial Sequence
<220> FEATURE:
<223> OTHER INFORMATION: Synthetic Polynucleotide

<400> SEQUENCE: 64
ugauaauagg cuggagccuc ggguggccaug cuucuugccc cuugggccuc ccccagccc      60 cuccuccccu uccugcaccc guaccccag uagugcuuuc uacuuuaugg ggucuuuga     120 auaaagucug agugggcggc                                                140

<210> SEQ ID NO 65
<211> LENGTH: 181
<212> TYPE: RNA
<213> ORGANISM: Artificial Sequence
<220> FEATURE:
<223> OTHER INFORMATION: Synthetic Polynucleotide

<400> SEQUENCE: 65
ugauaauaga guagugcuuu cuacuuuaug gcuggagccu cgguggccau gcuucuugcc      60
ccuugggcca guagugcuuu cuacuuuaug uccccccagc cccucccccc uuccugcacc     120
cguaccccca guagugcuuu cuacuuuaug guggucuuug aauaaagucu gagugggcgg     180
```

<210> SEQ ID NO 66
<211> LENGTH: 184
<212> TYPE: RNA
<213> ORGANISM: Artificial Sequence
<220> FEATURE:
<223> OTHER INFORMATION: Synthetic Polynucleotide

<400> SEQUENCE: 66
ugauaauaga guagugcuuu cuacuuuaug gcuggagccu cgguggccau gcuucuugcc    60
ccuugggccu ccauaaagua ggaaacacua cauccccca gccccuccuc cccuuccugc   120
acccguaccc ccaguagugc uuucuacuuu auggugucu uugaauaaag ucgaguggg    180 cggc                                                               184

<210> SEQ ID NO 67
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 67
ugauaauagg cuggagccuc gguggccaug cuucuugccc cuugggccuc ccccagccc    60 cuccucccu uccugcaccc guaccccac cccaucaca auuagcauua aguggucuuu    120
gaauaaaguc ugagugggcg gc                                           142

<210> SEQ ID NO 68
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 68
ugauaauaga ccccuaucac aauuagcauu aagcuggagc cucgguggcc augcuucuug    60
ccccuugggc cacccuauc acaauuagca uuaauccccc cagccccucc ucccuuccu    120 gcacccguac ccccaccccu aucacaauua gcauuaagug gucuuugaau aaagucugag    180
ugggcggc                                                             188

<210> SEQ ID NO 69
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 69
ugauaauaga ccccuaucac aauuagcauu aagcuggagc cucgguggcc augcuucuug    60
ccccuugggc cuccauaaag uaggaaacac uacauccccc cagccccucc ucccuuccu    120 gcacccguac ccccaccccu aucacaauua gcauuaagug gucuuugaau aaagucugag    180
ugggcggc                                                             188

<210> SEQ ID NO 70
<211> LENGTH: 142
<212> TYPE: RNA
<213> ORGANISM: Artificial Sequence
<220> FEATURE:
<223> OTHER INFORMATION: Synthetic Polynucleotide

```
<400> SEQUENCE: 70
ugauaauagg cuggagccuc gguggcucca uaaaguagga aacacuacac augcuucuug      60
ccccuugggc ucccccccag ccccuccucc ccuuccugca cccguacccc cguggucuuu     120
gaauaaaguc ugagugggcg gc                                              142

<210> SEQ ID NO 71
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 71
ugauaauagg cuggagccuc gguggccaug cuucuugccc cuugggccuc cauaaaguag      60
gaaacacuac auccccccag ccccuccucc ccuuccugca cccguacccc cguggucuuu    120
gaauaaaguc ugagugggcg gc                                              142

<210> SEQ ID NO 72
<211> LENGTH: 70
<212> TYPE: RNA
<213> ORGANISM: Artificial Sequence
<220> FEATURE:
<223> OTHER INFORMATION: Synthetic Polynucleotide

<400> SEQUENCE: 72
gggaaauaag aguccauaaa guaggaaaca cuacaagaaa agaagaguaa gaagaaauau     60
aagagccacc                                                             70

<210> SEQ ID NO 73
<211> LENGTH: 70
<212> TYPE: RNA
<213> ORGANISM: Artificial Sequence
<220> FEATURE:
<223> OTHER INFORMATION: Synthetic Polynucleotide

<400> SEQUENCE: 73
gggaaauaag agagaaaaga agaguaaucc auaaaguagg aaacacuaca gaagaaauau     60
aagagccacc                                                             70

<210> SEQ ID NO 74
<211> LENGTH: 70
<212> TYPE: RNA
<213> ORGANISM: Artificial Sequence
<220> FEATURE:
<223> OTHER INFORMATION: Synthetic Polynucleotide

<400> SEQUENCE: 74
gggaaauaag agagaaaaga agaguaagaa gaaauauaau ccauaaagua ggaaacacua     60
cagagccacc                                                             70
```